United States Patent
Ellis et al.

(10) Patent No.: US 10,563,220 B2
(45) Date of Patent: Feb. 18, 2020

(54) COMPOSITIONS AND METHODS FOR EFFICIENT TARGETING OF TRANSGENES

(71) Applicant: Monsanto Technology, LLC, St. Louis, MO (US)

(72) Inventors: Christine M. Ellis, Manchester, MO (US); Michael E. Goley, St. Charles, MO (US); Clayton T. Larue, Chesterfield, MO (US); Sherry L. LeClere, Ballwin, MO (US); Qungang Qi, Chesterfield, MO (US); Aihua Shao, St. Charles, MO (US); Kwan Y. Thai, O'Fallon, MO (US)

(73) Assignee: Monsanto Technology LLC, St. Louis, MO (US)

(*) Notice: Subject to any disclaimer, the term of this patent is extended or adjusted under 35 U.S.C. 154(b) by 0 days.

(21) Appl. No.: 15/368,410

(22) Filed: Dec. 2, 2016

(65) Prior Publication Data

US 2017/0175131 A1    Jun. 22, 2017

Related U.S. Application Data

(60) Provisional application No. 62/270,180, filed on Dec. 21, 2015, provisional application No. 62/364,715, filed on Jul. 20, 2016.

(51) Int. Cl.
  *C12N 15/82* (2006.01)
  *C12N 9/02* (2006.01)
  *C12N 15/52* (2006.01)

(52) U.S. Cl.
  CPC ....... *C12N 15/8274* (2013.01); *C12N 9/0069* (2013.01); *C12N 15/52* (2013.01); *C12N 15/8202* (2013.01)

(58) Field of Classification Search
  CPC .................. C12N 15/8274; C12N 15/8221
  See application file for complete search history.

(56) References Cited

U.S. PATENT DOCUMENTS

| | | | |
|---|---|---|---|
| 5,939,602 A * | 8/1999 | Volrath | C12N 5/04 435/320.1 |
| 7,838,729 B2 * | 11/2010 | Feng | C12N 9/0069 800/278 |
| 7,851,670 B2 | 12/2010 | Wan et al. | |
| 7,855,326 B2 | 12/2010 | Feng et al. | |
| 7,884,262 B2 | 2/2011 | Clemente et al. | |
| 7,939,721 B2 | 5/2011 | Arnevik et al. | |
| 8,754,011 B2 | 6/2014 | Bhatti et al. | |
| 2011/0162107 A1 | 6/2011 | Inze et al. | |
| 2013/0198886 A1 | 8/2013 | Feng et al. | |
| 2014/0123340 A1 | 5/2014 | Aponte et al. | |
| 2017/0037427 A1 | 2/2017 | Evdokimov et al. | |
| 2017/0058290 A1 | 3/2017 | Evdokimov et al. | |
| 2018/0044690 A1 | 2/2018 | Larue et al. | |
| 2019/0185873 A1 | 6/2019 | Larue et al. | |

FOREIGN PATENT DOCUMENTS

| | | |
|---|---|---|
| WO | WO 2007/146703 | 12/2007 |
| WO | WO 2008/105890 | 9/2008 |
| WO | WO 2015/022636 | 2/2015 |

OTHER PUBLICATIONS

Myouga, Fumiyoshi, et al. "An *Arabidopsis chloroplast*-targeted Hsp101 homologue, APG6, has an essential role in chloroplast development as well as heat-stress response." The Plant Journal 48.2 (2006): 249-260. (Year: 2006).*
International Search Report and Written Opinion regarding International Application No. PCT/US2016/067531, dated May 16, 2017.
Invitation to Pay Additional Fees regarding International Application No. PCT/US2016/067531, dated Feb. 17, 2017.
UNIPROTKB Accession No. Q9LF37, dated Oct. 1, 2000.
NCBI Accession No. NM_121549, dated May 26, 2011.
Emanuelsson et al., "ChloroP, a neural network-based method for predicting chloroplast transit peptides and their cleavage sites," *Protein Sci* 8(5):978-984; 1999.
Myouga et al., "An *Arabidopsis chloroplast*-targeted Hsp101 homologue, APG6, has an essential role in chloroplast development as well as heat-stress response," *Plant J* 48(2):249-260; 2006.
U.S. Appl. No. 16/218,822, filed Dec. 13, 2018, Larue et al.
USPTO: Non-Final Office Action regarding U.S. Appl. No. 15/224,276, dated Feb. 15, 2019.
Response to Non-Final Office Action regarding U.S. Appl. No. 15/224,276, dated Apr. 5, 2019.
USPTO: Notice of Allowance regarding U.S. Appl. No. 15/224,276, dated May 1, 2019.
USPTO: Notice of Allowance regarding U.S. Appl. No. 15/228,993, dated May 1, 2019.
Partial Supplementary European Search Report regarding Europe Application No. 16879934.4, dated Apr. 8, 2019.
Tabata et al., "Sequence and analysis of chromosome 5 of the plant *Arabidopsis thaliana*," Nature 408 (6814):823-826, 2000.
U.S. Appl. No. 16/452,305, filed Jun. 25, 2019, Evdokimov et al.
U.S. Appl. No. 16/452,327, filed Jun. 25, 2019, Evdokimov et al.
U.S. Appl. No. 16/452,349, filed Jun. 25, 2019, Evdokimov et al.

* cited by examiner

*Primary Examiner* — Weihua Fan
(74) *Attorney, Agent, or Firm* — Dentons US LLP; Pamela Sisson, Esq.

(57) ABSTRACT

The invention provides recombinant DNA molecules and constructs useful for providing efficient transgene sub-cellular localization of proteins in transgenic plants. Recombinant DNA molecules and constructs for conferring herbicide tolerance or resistance to plants are further provided, as well as plants exhibiting herbicide tolerance and methods for producing or utilizing such plants.

26 Claims, 1 Drawing Sheet
Specification includes a Sequence Listing.

APG6 + H_N10        12G088600TP + H_N10

SEQUENCE LISTING

<160> NUMBER OF SEQ ID NOS: 102

<210> SEQ ID NO 1
<211> LENGTH: 68

```
<212> TYPE: PRT
<213> ORGANISM: Arabidopsis thalinana

<400> SEQUENCE: 1

Met Ala Thr Ala Thr Thr Ala Thr Ala Ala Phe Ser Gly Val Val
1               5                   10                  15

Ser Val Gly Thr Glu Thr Arg Arg Ile Tyr Ser Phe Ser His Leu Gln
                20                  25                  30

Pro Ser Ala Ala Phe Pro Ala Lys Pro Ser Ser Phe Lys Ser Leu Lys
            35                  40                  45

Leu Lys Gln Ser Ala Arg Leu Thr Arg Arg Leu Asp His Arg Pro Phe
        50                  55                  60

Val Val Arg Cys
65

<210> SEQ ID NO 2
<211> LENGTH: 68
<212> TYPE: PRT
<213> ORGANISM: Artificial Sequence
<220> FEATURE:
<223> OTHER INFORMATION: Recombinant

<400> SEQUENCE: 2

Met Ala Ser Ser Thr Thr Thr Ala Thr Ala Ala Phe Ser Gly Val Val
1               5                   10                  15

Ser Val Gly Thr Glu Thr Arg Arg Ile Tyr Ser Phe Ser His Leu Gln
                20                  25                  30

Pro Ser Ala Ala Phe Pro Ala Lys Pro Ser Ser Phe Lys Ser Leu Lys
            35                  40                  45

Leu Lys Gln Ser Ala Arg Leu Thr Arg Arg Leu Asp His Arg Pro Phe
        50                  55                  60

Val Val Arg Cys
65

<210> SEQ ID NO 3
<211> LENGTH: 61
<212> TYPE: PRT
<213> ORGANISM: Arabidopsis thalinana

<400> SEQUENCE: 3

Met Ala Pro Ala Leu Ser Arg Ser Leu Tyr Thr Ser Pro Leu Thr Ser
1               5                   10                  15

Val Pro Ile Thr Pro Val Ser Ser Arg Leu Ser His Leu Arg Ser Ser
                20                  25                  30

Phe Leu Pro His Gly Gly Ala Leu Arg Thr Gly Val Ser Cys Ser Trp
            35                  40                  45

Asn Leu Glu Lys Arg Cys Asn Arg Phe Ala Val Lys Cys
        50                  55                  60

<210> SEQ ID NO 4
<211> LENGTH: 72
<212> TYPE: PRT
<213> ORGANISM: Petunia hybrida

<400> SEQUENCE: 4

Met Ala Gln Ile Asn Asn Met Ala Gln Gly Ile Gln Thr Leu Asn Pro
1               5                   10                  15

Asn Ser Asn Phe His Lys Pro Gln Val Pro Lys Ser Ser Ser Phe Leu
                20                  25                  30
```

Val Phe Gly Ser Lys Lys Leu Lys Asn Ser Ala Asn Ser Met Leu Val
            35                  40                  45

Leu Lys Lys Asp Ser Ile Phe Met Gln Lys Phe Cys Ser Phe Arg Ile
 50                  55                  60

Ser Ala Ser Val Ala Thr Ala Cys
 65                  70

<210> SEQ ID NO 5
<211> LENGTH: 57
<212> TYPE: PRT
<213> ORGANISM: Pisum sativum

<400> SEQUENCE: 5

Met Ala Ser Met Ile Ser Ser Ala Val Thr Thr Val Ser Arg Ala
 1               5                  10                  15

Ser Arg Gly Gln Ser Ala Ala Met Ala Pro Phe Gly Gly Leu Lys Ser
                20                  25                  30

Met Thr Gly Phe Pro Val Arg Lys Val Asn Thr Asp Ile Thr Ser Ile
             35                  40                  45

Thr Ser Asn Gly Gly Arg Val Lys Cys
 50                  55

<210> SEQ ID NO 6
<211> LENGTH: 77
<212> TYPE: PRT
<213> ORGANISM: Oryza sativa

<400> SEQUENCE: 6

Met Ala Ala Leu Thr Thr Ser Gln Leu Ala Thr Ser Ala Thr Gly Phe
 1               5                  10                  15

Gly Ile Ala Asp Arg Ser Ala Pro Ser Ser Leu Leu Arg His Gly Phe
                20                  25                  30

Gln Gly Leu Lys Pro Arg Ser Pro Ala Gly Gly Asp Ala Thr Ser Leu
             35                  40                  45

Ser Val Thr Thr Ser Ala Arg Ala Thr Pro Lys Gln Gln Arg Ser Val
 50                  55                  60

Gln Arg Gly Ser Arg Arg Phe Pro Ser Val Val Val Cys
 65                  70                  75

<210> SEQ ID NO 7
<211> LENGTH: 204
<212> TYPE: DNA
<213> ORGANISM: Artificial Sequence
<220> FEATURE:
<223> OTHER INFORMATION: Recombinant

<400> SEQUENCE: 7
atggccaccg ccaccactac cgccaccgct gcgttctccg gcgtggtgag cgtcggcact        60
gagacgcgca ggatctactc cttcagccac ctccagcctt ctgctgcgtt ccccgctaag      120
ccgtcttcgt tcaagagcct gaagctgaaa cagtccgcac gccttacccg cgcgcctggac     180 cataggccat tcgttgtcag gtgc                                              204

<210> SEQ ID NO 8
<211> LENGTH: 204
<212> TYPE: DNA
<213> ORGANISM: Artificial Sequence
<220> FEATURE:
<223> OTHER INFORMATION: Recombinant

<400> SEQUENCE: 8

```
atggcgacgg ctacgacgac tgctacggcg gcgtttagtg gtgtagtcag tgtaggaacg      60
gagactcgaa ggatttattc gttttctcat cttcaacctt ctgcggcttt tccggcgaag     120
cctagttcct tcaaatctct caaattaaag cagagcgcga ggctcacacg gcggcttgat     180
catcggccgt tcgttgtccg atgt                                            204
```

<210> SEQ ID NO 9
<211> LENGTH: 204
<212> TYPE: DNA
<213> ORGANISM: Artificial Sequence
<220> FEATURE:
<223> OTHER INFORMATION: Recombinant

<400> SEQUENCE: 9

```
atggctactg ctactaccac agctaccgct gcattctctg gtgttgtgag tgttggaacc      60
gagacacgta gaatttactc tttctcacac ttgcaaccta gcgcagcctt ccctgccaag     120
ccatcatcct ttaagtcctt gaagctgaaa cagtcggcga ggcttacgag gcgcctcgat     180
catagaccct ttgtggtccg atgc                                            204
```

<210> SEQ ID NO 10
<211> LENGTH: 204
<212> TYPE: DNA
<213> ORGANISM: Artificial Sequence
<220> FEATURE:
<223> OTHER INFORMATION: Recombinant

<400> SEQUENCE: 10

```
atggcaaccg cgactaccac cgcaacggca gctttctccg gggtagtttc agtcgggacg      60
gaaacccgca ggatctattc gttcagccat ttgcaacctt ccgcggcctt ccccgccaaa     120
ccctcgtctt ttaaatcgct gaaactcaaa cagtcagcac ggttgacccg aagattggac     180
caccgcccat ttgtagtgag gtgc                                            204
```

<210> SEQ ID NO 11
<211> LENGTH: 204
<212> TYPE: DNA
<213> ORGANISM: Artificial Sequence
<220> FEATURE:
<223> OTHER INFORMATION: Recombinant

<400> SEQUENCE: 11

```
atggccacgg ccacgaccac ggcaacagcg gccttttcgg gcgttgtatc cgtcgggaca      60
gaaaccagac gcatatatag cttctcacac ctgcaaccta gtgccgcttt ccggccaaa     120 cctagctcgt ttaaatcgct gaagctcaaa cagagcgctc ggttaactag acgactggac     180
cataggccat ttgtcgtccg ctgc                                            204
```

<210> SEQ ID NO 12
<211> LENGTH: 204
<212> TYPE: DNA
<213> ORGANISM: Artificial Sequence
<220> FEATURE:
<223> OTHER INFORMATION: Recombinant

<400> SEQUENCE: 12

```
atggcttcct ccacgacgac tgctacggcg gcgtttagtg gtgtagtcag tgtaggaacg      60
gagactcgaa ggatttattc gttttctcat cttcaacctt ctgcggcttt tccggcgaag     120
cctagttcct tcaaatctct caaattaaag cagagcgcga ggctcacacg gcggcttgat     180
```

```
catcggccgt tcgttgtccg atgt                                              204
```

<210> SEQ ID NO 13
<211> LENGTH: 183
<212> TYPE: DNA
<213> ORGANISM: Artificial Sequence
<220> FEATURE:
<223> OTHER INFORMATION: Recombinant

<400> SEQUENCE: 13

```
atggctcctg ctttgagtag aagtctctac acatctcctt tgacttcagt tccaatcact     60
cctgtctctt ctcgtctctc tcatctgaga agctcgtttc tcccacacgg cggcgcttta    120
agaaccggcg tttcgtgtag ctggaatctc gaaaagagat gtaaccgatt cgccgtgaag    180
tgt                                                                  183
```

<210> SEQ ID NO 14
<211> LENGTH: 183
<212> TYPE: DNA
<213> ORGANISM: Artificial Sequence
<220> FEATURE:
<223> OTHER INFORMATION: Recombinant

<400> SEQUENCE: 14

```
atggctccgg ctctcagccg ctccctctac accagccctc tcacctccgt gcccatcacc     60
ccggtgtcct cccgcctctc ccacctccgc tcctccttcc tccctcacgg cggcgcgctc    120
cgcaccggcg tgtcctgctc ctggaacctg agaagcgct gcaaccgctt cgccgtgaag    180
tgc                                                                  183
```

<210> SEQ ID NO 15
<211> LENGTH: 216
<212> TYPE: DNA
<213> ORGANISM: Artificial Sequence
<220> FEATURE:
<223> OTHER INFORMATION: Recombinant

<400> SEQUENCE: 15

```
atggcccaga tcaacaacat ggcccagggc atccagaccc tgaaccctaa ctctaacttc     60
cacaagccgc aagtgcccaa gtctagctcc ttcctcgtgt tcggctccaa gaagctcaag    120
aatagcgcca attccatgct ggtcctgaag aaagactcga tcttcatgca gaagttctgc    180
tcctttcgca tcagtgcttc ggttgcgact gcctgc                              216
```

<210> SEQ ID NO 16
<211> LENGTH: 171
<212> TYPE: DNA
<213> ORGANISM: Artificial Sequence
<220> FEATURE:
<223> OTHER INFORMATION: Recombinant

<400> SEQUENCE: 16

```
atggcttcta tgatatcctc ttccgctgtg acaacagtca gccgtgcctc taggggcaa      60
tccgccgcaa tggctccatt cggcggcctc aaatccatga ctggattccc agtgaggaag    120
gtcaacactg acattacttc cattacaagc aatggtggaa gagtaaagtg c             171
```

<210> SEQ ID NO 17
<211> LENGTH: 231
<212> TYPE: DNA
<213> ORGANISM: Artificial Sequence
<220> FEATURE:
<223> OTHER INFORMATION: Recombinant

<400> SEQUENCE: 17

```
atggcggctc tcaccacgtc ccagctcgcc acctcggcca ccggcttcgg catcgccgac      60
aggtcggcgc cgtcgtcgct gctccgccac gggttccagg gcctcaagcc ccgcagcccc     120
gccggcggcg acgcgacgtc gctcagcgtg acgaccagcg cgcgcgcgac gcccaagcag     180
cagcggtcgg tgcagcgtgg cagccggagg ttcccctccg tcgtcgtgtg c              231
```

<210> SEQ ID NO 18
<211> LENGTH: 340
<212> TYPE: PRT
<213> ORGANISM: Artificial Sequence
<220> FEATURE:
<223> OTHER INFORMATION: Recombinant

<400> SEQUENCE: 18

```
Met Leu Thr Phe Val Arg Asn Ala Trp Tyr Val Ala Ala Leu Pro Glu
1               5                   10                  15

Glu Leu Ser Glu Lys Pro Leu Gly Arg Thr Ile Leu Asp Thr Pro Leu
            20                  25                  30

Ala Leu Tyr Arg Gln Pro Asp Gly Val Val Ala Ala Leu Leu Asp Ile
        35                  40                  45

Cys Pro His Arg Phe Ala Pro Leu Ser Asp Gly Ile Leu Val Asn Gly
    50                  55                  60

His Leu Gln Cys Pro Tyr His Gly Leu Glu Phe Asp Gly Gly Gly Gln
65                  70                  75                  80

Cys Val His Asn Pro His Gly Asn Gly Ala Arg Pro Ala Ser Leu Asn
                85                  90                  95

Val Arg Ser Phe Pro Val Val Glu Arg Asp Ala Leu Ile Trp Ile Trp
            100                 105                 110

Pro Gly Asp Pro Ala Leu Ala Asp Pro Gly Ala Ile Pro Asp Phe Gly
        115                 120                 125

Cys Arg Val Asp Pro Ala Tyr Arg Thr Val Gly Tyr Gly His Val
    130                 135                 140

Asp Cys Asn Tyr Lys Leu Leu Val Asp Asn Leu Met Asp Leu Gly His
145                 150                 155                 160

Ala Gln Tyr Val His Arg Ala Asn Ala Gln Thr Asp Ala Phe Asp Arg
                165                 170                 175

Leu Glu Arg Glu Val Ile Val Gly Asp Gly Glu Ile Gln Ala Leu Met
            180                 185                 190

Lys Ile Pro Gly Gly Thr Pro Ser Val Leu Met Ala Lys Phe Leu Arg
        195                 200                 205

Gly Ala Asn Thr Pro Val Asp Ala Trp Asn Asp Ile Arg Trp Asn Lys
    210                 215                 220

Val Ser Ala Met Leu Asn Phe Ile Ala Val Ala Pro Glu Gly Thr Pro
225                 230                 235                 240

Lys Glu Gln Ser Ile His Ser Arg Gly Thr His Ile Leu Thr Pro Glu
                245                 250                 255

Thr Glu Ala Ser Cys His Tyr Phe Phe Gly Ser Ser Arg Asn Phe Gly
            260                 265                 270

Ile Asp Asp Pro Glu Met Asp Gly Val Leu Arg Ser Trp Gln Ala Gln
        275                 280                 285

Ala Leu Val Lys Glu Asp Lys Val Val Glu Ala Ile Glu Arg Arg
    290                 295                 300

Arg Ala Tyr Val Glu Ala Asn Gly Ile Arg Pro Ala Met Leu Ser Cys
```

```
                    305                 310                 315                 320
Asp Glu Ala Ala Val Arg Val Ser Arg Glu Ile Glu Lys Leu Glu Gln
                325                 330                 335

Leu Glu Ala Ala
            340

<210> SEQ ID NO 19
<211> LENGTH: 339
<212> TYPE: PRT
<213> ORGANISM: Artificial Sequence
<220> FEATURE:
<223> OTHER INFORMATION: Recombinant

<400> SEQUENCE: 19

Met Thr Phe Val Arg Asn Ala Trp Tyr Val Ala Ala Leu Pro Glu Glu
1               5                   10                  15

Leu Ser Glu Lys Pro Leu Gly Arg Thr Ile Leu Asp Thr Pro Leu Ala
                20                  25                  30

Leu Tyr Arg Gln Pro Asp Gly Val Val Ala Ala Leu Leu Asp Ile Cys
            35                  40                  45

Pro His Arg Phe Ala Pro Leu Ser Asp Gly Ile Leu Val Asn Gly His
        50                  55                  60

Leu Gln Cys Pro Tyr His Gly Leu Glu Phe Asp Gly Gly Gly Gln Cys
65                  70                  75                  80

Val His Asn Pro His Gly Asn Gly Ala Arg Pro Ala Ser Leu Asn Val
                85                  90                  95

Arg Ser Phe Pro Val Val Glu Arg Asp Ala Leu Ile Trp Ile Trp Pro
            100                 105                 110

Gly Asp Pro Ala Leu Ala Asp Pro Gly Ala Ile Pro Asp Phe Gly Cys
        115                 120                 125

Arg Val Asp Pro Ala Tyr Arg Thr Val Gly Tyr Gly His Val Asp
            130                 135                 140

Cys Asn Tyr Lys Leu Leu Val Asp Asn Leu Met Asp Leu Gly His Ala
145                 150                 155                 160

Gln Tyr Val His Arg Ala Asn Ala Gln Thr Asp Ala Phe Asp Arg Leu
                165                 170                 175

Glu Arg Glu Val Ile Val Gly Asp Gly Glu Ile Gln Ala Leu Met Lys
            180                 185                 190

Ile Pro Gly Gly Thr Pro Ser Val Leu Met Ala Lys Phe Leu Arg Gly
        195                 200                 205

Ala Asn Thr Pro Val Asp Ala Trp Asn Asp Ile Arg Trp Asn Lys Val
    210                 215                 220

Ser Ala Met Leu Asn Phe Ile Ala Val Ala Pro Glu Gly Thr Pro Lys
225                 230                 235                 240

Glu Gln Ser Ile His Ser Arg Gly Thr His Ile Leu Thr Pro Glu Thr
                245                 250                 255

Glu Ala Ser Cys His Tyr Phe Phe Gly Ser Ser Arg Asn Phe Gly Ile
            260                 265                 270

Asp Asp Pro Glu Met Asp Gly Val Leu Arg Ser Trp Gln Ala Gln Ala
        275                 280                 285

Leu Val Lys Glu Asp Lys Val Val Glu Ala Ile Glu Arg Arg
    290                 295                 300

Ala Tyr Val Glu Ala Asn Gly Ile Arg Pro Ala Met Leu Ser Cys Asp
305                 310                 315                 320

Glu Ala Ala Val Arg Val Ser Arg Glu Ile Glu Lys Leu Glu Gln Leu
```

Glu Ala Ala

<210> SEQ ID NO 20
<211> LENGTH: 340
<212> TYPE: PRT
<213> ORGANISM: Artificial Sequence
<220> FEATURE:
<223> OTHER INFORMATION: Recombinant

<400> SEQUENCE: 20

Met Leu Thr Phe Val Arg Asn Ala Trp Tyr Val Ala Ala Leu Pro Glu
1               5                   10                  15

Glu Leu Ser Glu Lys Pro Leu Gly Arg Thr Ile Leu Asp Thr Pro Leu
            20                  25                  30

Ala Leu Tyr Arg Gln Pro Asp Gly Val Ala Ala Leu Leu Asp Ile
        35                  40                  45

Cys Pro His Arg Phe Ala Pro Leu Ser Asp Gly Ile Leu Val Asn Gly
50                  55                  60

His Leu Gln Cys Pro Tyr His Gly Leu Glu Phe Asp Gly Gly Gly Gln
65                  70                  75                  80

Cys Val His Asn Pro His Gly Asn Gly Ala Arg Pro Ala Ser Leu Asn
                85                  90                  95

Val Arg Ser Phe Pro Val Val Glu Arg Asp Ala Leu Ile Trp Ile Trp
            100                 105                 110

Pro Gly Asp Pro Ala Leu Ala Asp Pro Gly Ala Ile Pro Asp Phe Gly
        115                 120                 125

Cys Arg Val Asp Pro Ala Tyr Arg Thr Val Gly Gly Tyr Gly His Val
130                 135                 140

Asp Cys Asn Tyr Lys Leu Leu Val Asp Asn Leu Met Asp Leu Gly His
145                 150                 155                 160

Ala Gln Tyr Val His Arg Ala Asn Ala Gln Thr Asp Ala Phe Asp Arg
                165                 170                 175

Leu Glu Arg Glu Val Ile Val Gly Asp Gly Glu Ile Gln Ala Leu Met
            180                 185                 190

Lys Ile Pro Gly Gly Thr Pro Ser Val Leu Met Ala Lys Phe Leu Arg
        195                 200                 205

Gly Ala Asn Thr Pro Val Asp Ala Trp Asn Asp Ile Arg Trp Asn Lys
210                 215                 220

Val Ser Ala Met Leu Asn Phe Ile Ala Val Ala Pro Glu Gly Thr Pro
225                 230                 235                 240

Lys Glu Gln Ser Ile His Ser Arg Gly Thr His Ile Leu Thr Pro Glu
                245                 250                 255

Thr Glu Ala Ser Cys His Tyr Phe Phe Gly Ser Ser Arg Asn Phe Gly
            260                 265                 270

Ile Asp Asp Pro Glu Met Asp Gly Val Leu Arg Ser Trp Gln Ala Gln
        275                 280                 285

Ala Leu Val Lys Glu Asp Lys Val Val Glu Ala Ile Glu Arg Arg
290                 295                 300

Arg Ala Tyr Val Glu Ala Asn Gly Ile Arg Pro Ala Met Leu Ser Cys
305                 310                 315                 320

Asp Glu Ala Ala Val Arg Val Ser Arg Glu Ile Glu Lys Leu Glu Gln
                325                 330                 335

Leu Glu Ala Ala
            340

<210> SEQ ID NO 21
<211> LENGTH: 340
<212> TYPE: PRT
<213> ORGANISM: Artificial Sequence
<220> FEATURE:
<223> OTHER INFORMATION: Recombinant

<400> SEQUENCE: 21

```
Met Ala Thr Phe Val Arg Asn Ala Trp Tyr Ala Ala Leu Pro Glu
 1               5                  10                  15

Glu Leu Ser Glu Lys Pro Leu Gly Arg Thr Ile Leu Asp Thr Pro Leu
                20                  25                  30

Ala Leu Tyr Arg Gln Pro Asp Gly Val Val Ala Ala Leu Leu Asp Ile
                35                  40                  45

Cys Pro His Arg Phe Ala Pro Leu Ser Asp Gly Ile Leu Val Asn Gly
        50                  55                  60

His Leu Gln Cys Pro Tyr His Gly Leu Glu Phe Asp Gly Gly Gln
 65                  70                  75                  80

Cys Val His Asn Pro His Gly Asn Gly Ala Arg Pro Ala Ser Leu Asn
                85                  90                  95

Val Arg Ser Phe Pro Val Val Glu Arg Asp Ala Leu Ile Trp Ile Cys
                100                 105                 110

Pro Gly Asp Pro Ala Leu Ala Asp Pro Gly Ala Ile Pro Asp Phe Gly
                115                 120                 125

Cys Arg Val Asp Pro Ala Tyr Arg Thr Val Gly Gly Tyr Gly His Val
        130                 135                 140

Asp Cys Asn Tyr Lys Leu Leu Val Asp Asn Leu Met Asp Leu Gly His
145                 150                 155                 160

Ala Gln Tyr Val His Arg Ala Asn Ala Gln Thr Asp Ala Phe Asp Arg
                165                 170                 175

Leu Glu Arg Glu Val Ile Val Gly Asp Gly Glu Ile Gln Ala Leu Met
                180                 185                 190

Lys Ile Pro Gly Gly Thr Pro Ser Val Leu Met Ala Lys Phe Leu Arg
                195                 200                 205

Gly Ala Asn Thr Pro Val Asp Ala Trp Asn Asp Ile Arg Trp Asn Lys
        210                 215                 220

Val Ser Ala Met Leu Asn Phe Ile Ala Val Ala Pro Glu Gly Thr Pro
225                 230                 235                 240

Lys Glu Gln Ser Ile His Ser Arg Gly Thr His Ile Leu Thr Pro Glu
                245                 250                 255

Thr Glu Ala Ser Cys His Tyr Phe Phe Gly Ser Ser Arg Asn Phe Gly
                260                 265                 270

Ile Asp Asp Pro Glu Met Asp Gly Val Leu Arg Ser Trp Gln Ala Gln
                275                 280                 285

Ala Leu Val Lys Glu Asp Lys Val Val Glu Ala Ile Glu Arg Arg
        290                 295                 300

Arg Ala Tyr Val Glu Ala Asn Gly Ile Arg Pro Ala Met Leu Ser Cys
305                 310                 315                 320

Asp Glu Ala Ala Val Arg Val Ser Arg Glu Ile Glu Lys Leu Glu Gln
                325                 330                 335

Leu Glu Ala Ala
        340
```

<210> SEQ ID NO 22

```
<211> LENGTH: 340
<212> TYPE: PRT
<213> ORGANISM: Artificial Sequence
<220> FEATURE:
<223> OTHER INFORMATION: Recombinant

<400> SEQUENCE: 22

Met Leu Thr Phe Val Arg Asn Ala Trp Tyr Val Ala Ala Leu Pro Glu
1               5                   10                  15

Glu Leu Ser Glu Lys Pro Leu Gly Arg Thr Ile Leu Asp Thr Pro Leu
            20                  25                  30

Ala Leu Tyr Arg Gln Pro Asp Gly Val Val Ala Ala Leu Leu Asp Ile
        35                  40                  45

Cys Pro His Arg Phe Ala Pro Leu Ser Asp Gly Ile Leu Val Asn Gly
50                  55                  60

His Leu Gln Cys Pro Tyr His Gly Leu Glu Phe Asp Gly Gly Gly Gln
65                  70                  75                  80

Cys Val His Asn Pro His Gly Asn Gly Ala Arg Pro Ala Ser Leu Asn
                85                  90                  95

Val Arg Ser Phe Pro Val Val Glu Arg Asp Ala Leu Ile Trp Ile Cys
            100                 105                 110

Pro Gly Asp Pro Ala Leu Ala Asp Pro Gly Ala Ile Pro Asp Phe Gly
        115                 120                 125

Cys Arg Val Asp Pro Ala Tyr Arg Thr Val Gly Gly Tyr Gly His Val
130                 135                 140

Asp Cys Asn Tyr Lys Leu Leu Val Asp Asn Leu Met Asp Leu Gly His
145                 150                 155                 160

Ala Gln Tyr Val His Arg Ala Asn Ala Gln Thr Asp Ala Phe Asp Arg
                165                 170                 175

Leu Glu Arg Glu Val Ile Val Gly Asp Gly Glu Ile Gln Ala Leu Met
            180                 185                 190

Lys Ile Pro Gly Gly Thr Pro Ser Val Leu Met Ala Lys Phe Leu Arg
        195                 200                 205

Gly Ala Asn Thr Pro Val Asp Ala Trp Asn Asp Ile Arg Trp Asn Lys
210                 215                 220

Val Ser Ala Met Leu Asn Phe Ile Ala Val Ala Pro Glu Gly Thr Pro
225                 230                 235                 240

Lys Glu Gln Ser Ile His Ser Arg Gly Thr His Ile Leu Thr Pro Glu
                245                 250                 255

Thr Glu Ala Ser Cys His Tyr Phe Phe Gly Ser Ser Arg Asn Phe Gly
            260                 265                 270

Ile Asp Asp Pro Glu Met Asp Gly Val Leu Arg Ser Trp Gln Ala Gln
        275                 280                 285

Ala Leu Val Lys Glu Asp Lys Val Val Val Ala Ile Glu Arg Arg
290                 295                 300

Arg Ala Tyr Val Glu Ala Asn Gly Ile Arg Pro Ala Met Leu Ser Cys
305                 310                 315                 320

Asp Glu Ala Ala Val Arg Val Ser Arg Glu Ile Glu Lys Leu Glu Gln
                325                 330                 335

Leu Glu Ala Ala
            340

<210> SEQ ID NO 23
<211> LENGTH: 340
<212> TYPE: PRT
<213> ORGANISM: Artificial Sequence
```

```
<220> FEATURE:
<223> OTHER INFORMATION: Recombinant

<400> SEQUENCE: 23

Met Ala Thr Phe Val Arg Asn Ala Trp Tyr Val Ala Ala Leu Pro Glu
1               5                  10                  15

Glu Leu Ser Glu Lys Pro Leu Gly Arg Thr Ile Leu Asp Thr Pro Leu
            20                  25                  30

Ala Leu Tyr Arg Gln Pro Asp Gly Val Ala Ala Leu Leu Asp Ile
        35                  40                  45

Cys Pro His Arg Phe Ala Pro Leu Ser Asp Gly Ile Leu Val Asn Gly
    50                  55                  60

His Leu Gln Cys Pro Tyr His Gly Leu Glu Phe Asp Gly Gly Gln
65                  70                  75                  80

Cys Val His Asn Pro His Gly Asn Gly Ala Arg Pro Ala Ser Leu Asn
                85                  90                  95

Val Arg Ser Phe Pro Val Val Glu Arg Asp Ala Leu Ile Trp Ile Cys
            100                 105                 110

Pro Gly Asp Pro Ala Leu Ala Asp Pro Gly Ala Ile Pro Asp Phe Gly
        115                 120                 125

Cys Arg Val Asp Pro Ala Tyr Arg Thr Val Gly Tyr Gly His Val
    130                 135                 140

Asp Cys Asn Tyr Lys Leu Leu Val Asp Asn Leu Met Asp Leu Gly His
145                 150                 155                 160

Ala Gln Tyr Val His Arg Ala Asn Ala Gln Thr Asp Ala Phe Asp Arg
                165                 170                 175

Leu Glu Arg Glu Val Ile Val Gly Asp Gly Glu Ile Gln Ala Leu Met
            180                 185                 190

Lys Ile Pro Gly Gly Thr Pro Ser Val Leu Met Ala Lys Phe Leu Arg
        195                 200                 205

Gly Ala Asn Thr Pro Val Asp Ala Trp Asn Asp Ile Arg Trp Asn Lys
    210                 215                 220

Val Ser Ala Met Leu Asn Phe Ile Ala Val Ala Pro Glu Gly Thr Pro
225                 230                 235                 240

Lys Glu Gln Ser Ile His Ser Arg Gly Thr His Ile Leu Thr Pro Glu
                245                 250                 255

Thr Glu Ala Ser Cys His Tyr Phe Phe Gly Ser Ser Arg Asn Phe Gly
            260                 265                 270

Ile Asp Asp Pro Glu Met Asp Gly Val Leu Arg Ser Trp Gln Ala Gln
        275                 280                 285

Ala Leu Val Lys Glu Asp Lys Val Val Glu Ala Ile Glu Arg Arg
    290                 295                 300

Arg Ala Tyr Val Glu Ala Asn Gly Ile Arg Pro Ala Met Leu Ser Cys
305                 310                 315                 320

Asp Glu Ala Ala Val Arg Val Ser Arg Glu Ile Glu Lys Leu Glu Gln
                325                 330                 335

Leu Glu Ala Ala
            340

<210> SEQ ID NO 24
<211> LENGTH: 340
<212> TYPE: PRT
<213> ORGANISM: Artificial Sequence
<220> FEATURE:
<223> OTHER INFORMATION: Recombinant
```

<400> SEQUENCE: 24

```
Met Ala Thr Phe Val Arg Asn Ala Trp Tyr Val Ala Ala Leu Pro Glu
1               5                   10                  15

Glu Leu Ser Glu Lys Pro Leu Gly Arg Thr Ile Leu Asp Thr Pro Leu
            20                  25                  30

Ala Leu Tyr Arg Gln Pro Asp Gly Val Val Ala Ala Leu Leu Asp Ile
        35                  40                  45

Cys Pro His Arg Phe Ala Pro Leu Ser Asp Gly Ile Leu Val Asn Gly
    50                  55                  60

His Leu Gln Cys Pro Tyr His Gly Leu Glu Phe Asp Gly Gly Gly Gln
65                  70                  75                  80

Cys Val His Asn Pro His Gly Asn Gly Ala Arg Pro Ala Ser Leu Asn
                85                  90                  95

Val Arg Ser Phe Pro Val Val Glu Arg Asp Ala Leu Ile Trp Ile Trp
            100                 105                 110

Pro Gly Asp Pro Ala Leu Ala Asp Pro Gly Ala Ile Pro Asp Phe Gly
        115                 120                 125

Cys Arg Val Asp Pro Ala Tyr Arg Thr Val Gly Gly Tyr Gly His Val
    130                 135                 140

Asp Cys Asn Tyr Lys Leu Leu Val Asp Asn Leu Met Asp Leu Gly His
145                 150                 155                 160

Ala Gln Tyr Val His Arg Ala Asn Ala Gln Thr Asp Ala Phe Asp Arg
                165                 170                 175

Leu Glu Arg Glu Val Ile Val Gly Asp Gly Glu Ile Gln Ala Leu Met
            180                 185                 190

Lys Ile Pro Gly Gly Thr Pro Ser Val Leu Met Ala Lys Phe Leu Arg
        195                 200                 205

Gly Ala Asn Thr Pro Val Asp Ala Trp Asn Asp Ile Arg Trp Asn Lys
    210                 215                 220

Val Ser Ala Met Leu Asn Phe Ile Ala Val Ala Pro Glu Gly Thr Pro
225                 230                 235                 240

Lys Glu Gln Ser Ile His Ser Arg Gly Thr His Ile Leu Thr Pro Glu
                245                 250                 255

Thr Glu Ala Ser Cys His Tyr Phe Phe Gly Ser Ser Arg Asn Phe Gly
            260                 265                 270

Ile Asp Asp Pro Glu Met Asp Gly Val Leu Arg Ser Trp Gln Ala Gln
        275                 280                 285

Ala Leu Val Lys Glu Asp Lys Val Val Glu Ala Ile Glu Arg Arg
    290                 295                 300

Arg Ala Tyr Val Glu Ala Asn Gly Ile Arg Pro Ala Met Leu Ser Cys
305                 310                 315                 320

Asp Glu Ala Ala Val Arg Val Ser Arg Glu Ile Glu Lys Leu Glu Gln
                325                 330                 335

Leu Glu Ala Ala
            340
```

<210> SEQ ID NO 25
<211> LENGTH: 340
<212> TYPE: PRT
<213> ORGANISM: Artificial Sequence
<220> FEATURE:
<223> OTHER INFORMATION: Recombinant

<400> SEQUENCE: 25

```
Met Leu Thr Phe Val Arg Asn Ala Trp Tyr Val Ala Ala Leu Pro Glu
```

```
            1               5                   10                  15
        Glu Leu Ser Glu Lys Pro Leu Gly Arg Thr Ile Leu Asp Thr Pro Leu
                        20                  25                  30

Ala Leu Tyr Arg Gln Pro Asp Gly Val Val Ala Ala Leu Leu Asp Ile
                        35                  40                  45

Cys Pro His Arg Phe Ala Pro Leu Ser Asp Gly Ile Leu Val Asn Gly
                        50                  55                  60

His Leu Gln Cys Pro Tyr His Gly Leu Glu Phe Asp Gly Gly Gln
        65                      70                  75                  80

Cys Val His Asn Pro His Gly Asn Gly Ala Arg Pro Ala Ser Leu Asn
                        85                  90                  95

Val Arg Ser Phe Pro Val Val Glu Arg Asp Ala Leu Ile Trp Ile Cys
                        100                 105                 110

Pro Gly Asp Pro Ala Leu Ala Asp Pro Gly Ala Ile Pro Asp Phe Gly
                        115                 120                 125

Cys Arg Val Asp Pro Ala Tyr Arg Thr Val Gly Gly Tyr Gly His Val
                        130                 135                 140

Asp Cys Asn Tyr Lys Leu Leu Val Asp Asn Leu Met Asp Leu Gly His
        145                     150                 155                 160

Ala Gln Tyr Val His Arg Ala Asn Ala Gln Thr Asp Ala Phe Asp Arg
                        165                 170                 175

Leu Glu Arg Glu Val Ile Val Gly Asp Gly Glu Ile Gln Ala Leu Met
                        180                 185                 190

Lys Ile Pro Gly Gly Thr Pro Ser Val Leu Met Ala Lys Phe Leu Arg
                        195                 200                 205

Gly Ala Asn Thr Pro Val Asp Ala Trp Asn Asp Ile Arg Trp Asn Lys
                        210                 215                 220

Val Ser Ala Met Leu Asn Phe Ile Ala Val Ala Pro Glu Gly Thr Pro
        225                     230                 235                 240

Lys Glu Gln Ser Ile His Ser Arg Gly Thr His Ile Leu Thr Pro Glu
                        245                 250                 255

Thr Glu Ala Ser Cys His Tyr Phe Phe Gly Ser Ser Arg Asn Phe Gly
                        260                 265                 270

Ile Asp Asp Pro Glu Met Asp Gly Val Leu Arg Ser Trp Gln Ala Gln
                        275                 280                 285

Ala Leu Val Lys Glu Asp Lys Val Val Val Glu Ala Ile Glu Arg Arg
                        290                 295                 300

Arg Ala Tyr Val Glu Ala Asn Gly Ile Arg Pro Ala Met Leu Ser Cys
        305                     310                 315                 320

Asp Glu Ala Ala Val Arg Val Ser Arg Glu Ile Glu Lys Leu Glu Gln
                        325                 330                 335

Leu Glu Ala Ala
                    340

<210> SEQ ID NO 26
<211> LENGTH: 340
<212> TYPE: PRT
<213> ORGANISM: Artificial Sequence
<220> FEATURE:
<223> OTHER INFORMATION: Recombinant

<400> SEQUENCE: 26

Met Ala Thr Phe Val Arg Asn Ala Trp Tyr Val Ala Ala Leu Pro Glu
        1               5                   10                  15

Glu Leu Ser Glu Lys Pro Leu Gly Arg Thr Ile Leu Asp Thr Pro Leu
```

```
            20                  25                  30
Ala Leu Tyr Arg Gln Pro Asp Gly Val Val Ala Leu Leu Asp Ile
        35                  40                  45

Cys Pro His Arg Phe Ala Pro Leu Ser Asp Gly Ile Leu Val Asn Gly
 50                  55                  60

His Leu Gln Cys Pro Tyr His Gly Leu Glu Phe Asp Gly Gly Gln
 65                  70                  75                  80

Cys Val His Asn Pro His Gly Asn Gly Ala Arg Pro Ala Ser Leu Asn
                 85                  90                  95

Val Arg Ser Phe Pro Val Val Glu Arg Asp Ala Leu Ile Trp Ile Trp
                100                 105                 110

Pro Gly Asp Pro Ala Leu Ala Asp Pro Gly Ala Ile Pro Asp Phe Gly
                115                 120                 125

Cys Arg Val Asp Pro Ala Tyr Arg Thr Val Gly Tyr Gly His Val
                130                 135                 140

Asp Cys Asn Tyr Lys Leu Leu Val Asp Asn Leu Met Asp Leu Gly His
145                 150                 155                 160

Ala Gln Tyr Val His Arg Ala Asn Ala Gln Thr Asp Ala Phe Asp Arg
                165                 170                 175

Leu Glu Arg Glu Val Ile Val Gly Asp Gly Glu Ile Gln Ala Leu Met
                180                 185                 190

Lys Ile Pro Gly Gly Thr Pro Ser Val Leu Met Ala Lys Phe Leu Arg
                195                 200                 205

Gly Ala Asn Thr Pro Val Asp Ala Trp Asn Asp Ile Arg Trp Asn Lys
                210                 215                 220

Val Ser Ala Met Leu Asn Phe Ile Ala Val Ala Pro Glu Gly Thr Pro
225                 230                 235                 240

Lys Glu Gln Ser Ile His Ser Arg Gly Thr His Ile Leu Thr Pro Glu
                245                 250                 255

Thr Glu Ala Ser Cys His Tyr Phe Phe Gly Ser Ser Arg Asn Phe Gly
                260                 265                 270

Ile Asp Asp Pro Glu Met Asp Gly Val Leu Arg Ser Trp Gln Ala Gln
                275                 280                 285

Ala Leu Val Lys Glu Asp Lys Val Val Glu Ala Ile Glu Arg Arg
                290                 295                 300

Arg Ala Tyr Val Glu Ala Asn Gly Ile Arg Pro Ala Met Leu Ser Cys
305                 310                 315                 320

Asp Glu Ala Ala Val Arg Val Ser Arg Glu Ile Glu Lys Leu Glu Gln
                325                 330                 335

Leu Glu Ala Ala
                340

<210> SEQ ID NO 27
<211> LENGTH: 340
<212> TYPE: PRT
<213> ORGANISM: Artificial Sequence
<220> FEATURE:
<223> OTHER INFORMATION: Recombinant

<400> SEQUENCE: 27

Met Leu Thr Phe Val Arg Asn Ala Trp Tyr Val Ala Ala Leu Pro Glu
 1               5                  10                  15

Glu Leu Ser Glu Lys Pro Leu Gly Arg Thr Ile Leu Asp Thr Pro Leu
                20                  25                  30

Ala Leu Tyr Arg Gln Pro Asp Gly Val Val Ala Ala Leu Leu Asp Ile
```

```
            35                  40                  45
Cys Pro His Arg Phe Ala Pro Leu Ser Asp Gly Ile Leu Val Asn Gly
 50                  55                  60
His Leu Gln Cys Pro Tyr His Gly Leu Glu Phe Asp Gly Gly Gly Gln
 65                  70                  75                  80
Cys Val His Asn Pro Leu Gly Asn Gly Ala Arg Pro Ala Ser Leu Asn
                 85                  90                  95
Val Arg Ser Phe Pro Val Val Glu Arg Asp Ala Leu Ile Trp Ile Trp
            100                 105                 110
Pro Gly Asp Pro Ala Leu Ala Asp Pro Gly Ala Ile Pro Asp Phe Gly
            115                 120                 125
Cys Arg Val Asp Pro Ala Tyr Arg Thr Val Gly Tyr Gly His Val
            130                 135                 140
Asp Cys Asn Tyr Lys Leu Leu Val Asp Asn Leu Met Asp Leu Gly His
145                 150                 155                 160
Ala Gln Tyr Val His Arg Ala Asn Ala Gln Thr Asp Ala Phe Asp Arg
                165                 170                 175
Leu Glu Arg Glu Val Ile Lys Gly Asp Gly Glu Ile Gln Ala Leu Met
            180                 185                 190
Lys Ile Pro Gly Gly Thr Pro Ser Val Leu Met Ala Lys Phe Leu Arg
            195                 200                 205
Gly Ala Asn Thr Pro Val Asp Ala Trp Asn Asp Ile Arg Trp Asn Lys
210                 215                 220
Val Ser Ala Met Leu Asn Phe Ile Ala Val Ala Pro Glu Gly Thr Pro
225                 230                 235                 240
Lys Glu Gln Ser Ile His Ser Arg Gly Thr His Ile Leu Thr Pro Glu
                245                 250                 255
Thr Glu Ala Ser Cys His Tyr Phe Phe Gly Ser Ser Arg Asn Phe Gly
            260                 265                 270
Ile Asp Asp Pro Glu Met Asp Gly Val Leu Arg Ser Trp Gln Ala Gln
            275                 280                 285
Ala Leu Val Lys Glu Asp Lys Val Val Glu Ala Ile Glu Arg Arg
            290                 295                 300
Arg Ala Tyr Val Glu Ala Asn Gly Ile Arg Pro Ala Met Leu Ser Cys
305                 310                 315                 320
Asp Glu Ala Ala Val Arg Val Ser Arg Glu Ile Glu Lys Leu Glu Gln
                325                 330                 335
Leu Glu Ala Ala
            340

<210> SEQ ID NO 28
<211> LENGTH: 1023
<212> TYPE: DNA
<213> ORGANISM: Artificial Sequence
<220> FEATURE:
<223> OTHER INFORMATION: Recombinant

<400> SEQUENCE: 28
atgctcactt tcgttagaaa cgcttggtac gttgctgcac ttcctgagga gttgagcgag      60
aagcctctag gaagaactat cctcgatact ccactagctc tctatcgtca acctgacgga     120
gttgtcgctg ccctgcttga tatttgtccg catcgcttcg ctccgttgag tgacggtatt     180
ctagtcaacg gacatctcca gtgtccatat acggtctgg aatttgacgg aggtggccag      240
tgtgtccaca acccgcacgg caacggagcc cgccctgctt ctctgaacgt gcgatcattc     300
```

| | |
|---|---|
| cctgtcgtgg aaagagacgc attgatctgg atctggcctg gagatccagc actcgcagat | 360 |
| cccggtgcta tccctgactt tgggtgtcgt gttgatccag cttaccgtac tgtcggaggt | 420 |
| tacggtcacg tggactgcaa ctacaagctc cttgtggata acctcatgga tcttggacac | 480 |
| gctcagtacg tgcaccgcgc taacgcccaa acagacgcct tcgatagact tgagcgtgag | 540 |
| gtgatcgttg gcgacggcga gatccaggcg ctcatgaaga tccctggtgg cacaccctca | 600 |
| gttctcatgg ctaagttctt gcgtggtgct aacacaccag ttgacgcctg aacgacatc | 660 |
| cggtggaata aggtgtcggc tatgctgaac ttcatcgcgg tcgcgccgga agggacgccg | 720 |
| aaggagcagt caatccactc ccgaggaacc catatcctta ctcctgagac cgaggcaagc | 780 |
| tgccattact tcttcggtag ttcccgcaac ttcggtatag acgatccaga gatggacggt | 840 |
| gttctcagga gctggcaagc tcaagccctg gtgaaggagg acaaagtggt cgttgaagct | 900 |
| atcgaaaggc ggagggctta cgtcgaagcg aacgggatca gacccgccat gttgtcctgc | 960 |
| gacgaggcag ccgtcagggt atccaggag attgagaagc tcgaacaact agaagcggcg | 1020 |
| tga | 1023 |

<210> SEQ ID NO 29
<211> LENGTH: 1020
<212> TYPE: DNA
<213> ORGANISM: Artificial Sequence
<220> FEATURE:
<223> OTHER INFORMATION: Recombinant

<400> SEQUENCE: 29

| | |
|---|---|
| atgaccttcg tccgcaatgc ctggtatgtg gcggcgctgc ccgaggaact gtccgaaaag | 60 |
| ccgctcggcc ggacgattct cgacacaccg ctcgcgctct accgccagcc cgacggtgtg | 120 |
| gtcgcggcgc tgctcgacat ctgtccgcac cgcttcgcgc cgctgagcga cggcatcctc | 180 |
| gtcaacggcc atctccaatg cccctatcac gggctggaat tcgatggcgg cgggcagtgc | 240 |
| gtccataacc cgcacggcaa tggcgcccgc ccggcttcgc tcaacgtccg ctccttcccg | 300 |
| gtggtggagc gcgacgcgct gatctggatc tggcccggcg atccggcgct ggccgatcct | 360 |
| ggggcgatcc ccgacttcgg ctgccgcgtc gatcccgcct atcggaccgt cggcggctat | 420 |
| gggcatgtcg actgcaacta caagctgctg gtcgacaacc tgatggacct cggccacgcc | 480 |
| caatatgtcc atcgcgccaa cgcccagacc gacgccttcg accggctgga gcgcgaggtg | 540 |
| atcgtcggcg acggtgagat acaggcgctg atgaagattc ccggcggcac gccgagcgtg | 600 |
| ctgatggcca gttcctgcg cggcgccaat accccgtcg acgcttggaa cgacatccgc | 660 |
| tggaacaagg tgagcgcgat gctcaacttc atcgcggtgg cgccggaagg caccccgaag | 720 |
| gagcagagca tccactcgcg cggtacccat atcctgaccc ccgagacgga ggcgagctgc | 780 |
| cattatttct tcggctcctc gcgcaatttc ggcatcgacg atccggagat ggacggcgtg | 840 |
| ctgcgcagct ggcaggctca ggcgctggtc aaggaggaca aggtcgtcgt cgaggcgatc | 900 |
| gagcgccgcc gcgcctatgt cgaggcgaat ggcatccgcc cggcgatgct gtcgtgcgac | 960 |
| gaagccgcag tccgtgtcag ccgcgagatc gagaagcttg agcagctcga agccgcctga | 1020 |

<210> SEQ ID NO 30
<211> LENGTH: 1023
<212> TYPE: DNA
<213> ORGANISM: Artificial Sequence
<220> FEATURE:
<223> OTHER INFORMATION: Recombinant

<400> SEQUENCE: 30

```
atgctcacct tcgttaggaa cgcctggtac gtcgccgctc tccctgagga gctgagcgag      60
aagcccttgg gtcgcaccat cctagacact ccgttagccc tttaccgcca gcctgacggc     120
gtagtggcgg ccctgcttga catctgcccg cataggttcg ctccgctcag cgacggcatc     180
ctcgtcaacg ggcatcttca gtgcccgtac cacgggctgg aatttgacgg cggtgggcag     240
tgtgtccaca acccgcacgg caacggcgca cggccagctt ccctcaacgt taggtcgttc     300
cctgttgtcg agcgcgacgc actgatctgg atctggcctg cgacccagc tctgccgat      360 ccaggagcca ttcccgactt cggttgccgc gtggacccag cctatcgac ggtcggcggt      420 tacgggcacg tcgattgtaa ctataagctc cttgtggaca accttatgga tttgggccac     480
gctcagtacg tgcaccgggc taacgctcag actgacgcct ttgaccgtct cgaaagggag     540
gtcatcgtcg cgacggaga gattcaggcg ctgatgaaga tccctggagg cacgccctct      600
gtgctcatgg cgaagtttct cagaggcgcg aacacgcccg tggacgcctg aacgacatc      660 cgctggaata aggtctccgc gatgctgaac ttcatcgccg ttgcgcccga gggcacaccc     720
aaagagcagt caatccacag cagagggacc catattctta caccggaaac cgaggctagt     780
tgccactact tcttcggctc gtcacggaat tcgggatag acgatccgga gatggacggt      840
gttcttcgat cttggcaagc gcaagctctc gtcaaggaag ataaggtggt cgtggaggct     900
atcgagcgta ggcgcgccta cgttgaggcg aacggtatta ggcccgcgat gctgtcctgc     960
gacgaggccg cagttagagt gtcgcgcgag atagaaaagc tggagcagct agaggccgcc    1020
tga                                                                   1023
```

<210> SEQ ID NO 31
<211> LENGTH: 1023
<212> TYPE: DNA
<213> ORGANISM: Artificial Sequence
<220> FEATURE:
<223> OTHER INFORMATION: Recombinant

<400> SEQUENCE: 31

```
atggccactt tcgttagaaa cgcttggtac gttgctgcac ttcctgagga gttgagcgag      60
aagcctctag gaagaactat cctcgatact ccactagctc tctatcgtca acctgacgga     120
gttgtcgctg ccctgcttga tatttgtccg catcgcttcg ctccgttgag tgacggtatt     180
ctagtcaacg gacatctcca gtgtccatat cacggtctgg aatttgacgg aggtggccag     240
tgtgtccaca acccgcacgg caacggagcc cgccctgctt ctctgaacgt gcgatcattc     300
cctgtcgtgg aaagagacgc attgatctgg atctgccctg gagatccagc actcgcagat     360
cccggtgcta tccctgactt tgggtgtcgt gttgatccag cttaccgtac tgtcggaggt     420
tacggtcacg tggactgcaa ctacaagctc cttgtggata acctcatgga tcttggacac     480
gctcagtacg tgcaccgcgc taacgcccaa acagacgcct tcgatagact tgagcgtgag     540
gtgatcgttg cgacggcga gatccaggcg ctcatgaaga tccctggtgg cacaccctca     600
gttctcatgg ctaagttctt gcgtggtgct aacacaccag ttgacgcctg aacgacatc     660 cggtggaata aggtgtcggc tatgctgaac ttcatcgcgg tcgcgccgga agggacgccg     720
aaggagcagt caatccactc ccgaggaacc catatcctta ctcctgagac cgaggcaagc     780
tgccattact tcttcggtag ttcccgcaac ttcggtatag acgatccaga gatggacggt     840
gttctcagga gctggcaagc tcaagccctg gtgaaggagg acaaagtggt cgttgaagct     900
atcgaaaggc ggagggctta cgtcgaagcg aacgggatca gacccgccat gttgtcctgc     960
```

```
gacgaggcag ccgtcagggt atccaggag attgagaagc tcgaacaact agaagcggcg   1020
tga                                                                1023

<210> SEQ ID NO 32
<211> LENGTH: 1023
<212> TYPE: DNA
<213> ORGANISM: Artificial Sequence
<220> FEATURE:
<223> OTHER INFORMATION: Recombinant

<400> SEQUENCE: 32
atgctcactt tcgttagaaa cgcttggtac gttgctgcac ttcctgagga gttgagcgag     60
aagcctctag gaagaactat cctcgatact ccactagctc tctatcgtca acctgacgga    120
gttgtcgctg ccctgcttga tatttgtccg catcgcttcg ctccgttgag tgacggtatt    180
ctagtcaacg gacatctcca gtgtccatat cacggtctgg aatttgacgg aggtggccag    240
tgtgtccaca acccgcacgg caacggagcc cgccctgctt ctctgaacgt gcgatcattc    300
cctgtcgtgg aaagagacgc attgatctgg atctgccctg gagatccagc actcgcagat    360
cccggtgcta tccctgactt tgggtgtcgt gttgatccag cttaccgtac tgtcggaggt    420
tacggtcacg tggactgcaa ctacaagctc cttgtggata acctcatgga tcttggacac    480
gctcagtacg tgcaccgcgc taacgcccaa acagacgcct tcgatagact tgagcgtgag    540
gtgatcgttg gcgacggcga gatccaggcg ctcatgaaga tccctggtgg cacaccctca    600
gttctcatgg ctaagttctt gcgtggtgct aacacaccag ttgacgcctg aacgacatc    660 cggtggaata aggtgtcggc tatgctgaac ttcatcgcgg tcgcgccgga agggacgccg    720
aaggagcagt caatccactc ccgaggaacc catatcctta ctcctgagac cgaggcaagc    780
tgccattact tcttcggtag ttcccgcaac ttcggtatag cgatccaga gatgacggt     840 gttctcagga gctggcaagc tcaagccctg gtgaaggagg acaaagtggt cgttgaagct    900
atcgaaaggc ggagggctta cgtcgaagcg aacgggatca gacccgccat gttgtcctgc    960
gacgaggcag ccgtcagggt atccaggag attgagaagc tcgaacaact agaagcggcg   1020
tga                                                                1023

<210> SEQ ID NO 33
<211> LENGTH: 1023
<212> TYPE: DNA
<213> ORGANISM: Artificial Sequence
<220> FEATURE:
<223> OTHER INFORMATION: Recombinant

<400> SEQUENCE: 33
atggccacct tcgtccgcaa tgcctggtat gtggcggcgc tgcccgagga actgtccgaa     60
aagccgctcg gccggacgat tctcgacaca ccgctcgcgc tctaccgcca gcccgacggt    120
gtggtcgcgg cgctgctcga catctgtccg caccgcttcg cgccgctgag cgacggcatc    180
ctcgtcaacg gccatctcca atgccctat cacgggctgg aattcgatgg cggcgggcag    240
tgcgtccata acccgcacgg caatggcgcc cgcccggctt cgctcaacgt ccgctccttc    300
ccggtggtgg agcgcgacgc gctgatctgg atctgtcccg gcgatccggc gctgccgat    360 cctggggcga tccccgactt cggctgccgc gtcgatcccg cctatcggac cgtcggcggc    420
tatgggcatg tcgactgcaa ctacaagctg ctggtcgaca acctgatgga cctcggccac    480
gcccaatatg tccatcgcgc caacgcccag accgacgcct tcgaccgct ggagcgcgag    540 gtgatcgtcg gcgacggtga gatacaggcg ctgatgaaga ttcccggcgg cacgccgagc    600
```

```
gtgctgatgg ccaagttcct gcgcggcgcc aatacccccg tcgacgcttg aacgacatc      660 cgctggaaca aggtgagcgc gatgctcaac ttcatcgcgg tggcgccgga aggcaccccg      720
aaggagcaga gcatccactc gcgcggtacc catatcctga cccccgagac ggaggcgagc      780
tgccattatt tcttcggctc ctcgcgcaat tcggcatcg acgatccgga gatggacggc       840
gtgctgcgca gctggcaggc tcaggcgctg gtcaaggagg acaaggtcgt cgtcgaggcg      900
atcgagcgcc gccgcgccta tgtcgaggcg aatggcatcc gcccggcgat gctgtcgtgc     960
gacgaagccg cagtccgtgt cagccgcgag atcgagaagc ttgagcagct cgaagccgcc     1020
tga                                                                    1023

<210> SEQ ID NO 34
<211> LENGTH: 1023
<212> TYPE: DNA
<213> ORGANISM: Artificial Sequence
<220> FEATURE:
<223> OTHER INFORMATION: Recombinant

<400> SEQUENCE: 34
atggccactt tcgttagaaa cgcttggtac gttgctgcac ttcctgagga gttgagcgag      60
aagcctctag gaagaactat cctcgatact ccactagctc tctatcgtca acctgacgga     120
gttgtcgctg ccctgcttga tatttgtccg catcgcttcg ctccgttgag tgacggtatt     180
ctagtcaacg gacatctcca gtgtccatat cacggtctgg aatttgacgg aggtggccag     240
tgtgtccaca acccgcacgg caacggagcc cgccctgctt ctctgaacgt gcgatcattc     300
cctgtcgtgg aaagagacgc attgatctgg atctggcctg gagatccagc actcgcagat    360
cccggtgcta tccctgactt tgggtgtcgt gttgatccag cttaccgtac tgtcggaggt     420
tacggtcacg tggactgcaa ctacaagctc cttgtggata acctcatgga tcttggacac    480
gctcagtacg tgcaccgcgc taacgcccaa acagacgcct tcgatagact tgagcgtgag    540
gtgatcgttg gcgacggcga gatccaggcg ctcatgaaga tccctggtgg cacaccctca    600
gttctcatgg ctaagttctt gcgtggtgct aacacaccag ttgacgcctg gaacgacatc    660
cggtggaata aggtgtcggc tatgctgaac ttcatcgcgg tcgcgccgga agggacgccg    720
aaggagcagt caatccactc ccgaggaacc catatcctta ctcctgagac cgaggcaagc    780
tgccattact tcttcggtag ttcccgcaac ttcggtatag acgatccaga gatggacggt    840
gttctcagga gctggcaagc tcaagccctg gtgaaggagg acaaagtggt cgttgaagct   900
atcgaaaggc ggagggctta cgtcgaagcg aacgggatca gacccgccat gttgtcctgc   960
gacgaggcag ccgtcagggt atccaggag attgagaagc tcgaacaact agaagcggcg   1020
tga                                                                1023

<210> SEQ ID NO 35
<211> LENGTH: 1023
<212> TYPE: DNA
<213> ORGANISM: Artificial Sequence
<220> FEATURE:
<223> OTHER INFORMATION: Recombinant

<400> SEQUENCE: 35
atgctcacct tcgtccgcaa tgcctggtat gtggcggcgc tgcccgagga actgtccgaa      60
aagccgctcg gccggacgat tctcgacaca ccgctcgcgc tctaccgcca gcccgacggt    120
gtggtcgcgg cgctgctcga catctgtccg caccgcttcg cgccgctgag cgacggcatc    180
```

-continued

```
ctcgtcaacg gccatctcca atgccctat cacgggctgg aattcgatgg cggcgggcag      240
tgcgtccata acccgcacgg caatggcgcc cgcccggctt cgctcaacgt ccgctccttc      300
ccggtggtgg agcgcgacgc gctgatctgg atctgtcccg gcgatccggc gctggccgat      360
cctggggcga tccccgactt cggctgccgc gtcgatcccg cctatcggac cgtcggcggc      420
tatgggcatg tcgactgcaa ctacaagctg ctggtcgaca acctgatgga cctcggccac      480
gcccaatatg tccatcgcgc caacgcccag accgacgcct tcgaccggct ggagcgcgag      540
gtgatcgtcg gcgacggtga gatacaggcg ctgatgaaga ttcccggcgg cacgccgagc      600
gtgctgatgg ccaagttcct gcgcggcgcc aatacccccg tcgacgcttg aacgacatc       660
cgctggaaca aggtgagcgc gatgctcaac ttcatcgcgg tggcgccgga aggcaccccg      720
aaggagcaga gcatccactc gcgcggtacc catatcctga cccccgagac ggaggcgagc      780
tgccattatt tcttcggctc ctcgcgcaat ttcggcatcg acgatccgga gatggacggc      840
gtgctgcgca gctggcaggc tcaggcgctg gtcaaggagg acaaggtcgt cgtcgaggcg      900
atcgagcgcc gccgcgccta tgtcgaggcg aatggcatcc gcccggcgat gctgtcgtgc      960
gacgaagccg cagtccgtgt cagccgcgag atcgagaagc ttgagcagct cgaagccgcc     1020
tga                                                                   1023
```

<210> SEQ ID NO 36
<211> LENGTH: 1023
<212> TYPE: DNA
<213> ORGANISM: Artificial Sequence
<220> FEATURE:
<223> OTHER INFORMATION: Recombinant

<400> SEQUENCE: 36

```
atggccacct tcgttaggaa cgcctggtac gtcgccgctc tccctgagga gctgagcgag       60
aagcccttgg gtcgcaccat cctagacact ccgttagccc tttaccgcca gcctgacggc      120
gtagtggcgg ccctgcttga catctgcccg cataggttcg ctccgctcag cgacggcatc      180
ctcgtcaacg ggcatcttca gtgcccgtac cacgggctgg aatttgacgg cggtgggcag      240
tgtgtccaca acccgcacgg caacggcgca cggccagctt ccctcaacgt taggtcgttc      300
cctgttgtcg agcgcgacgc actgatctgg atctggcctg gcgacccagc tctggccgat      360
ccaggagcca ttcccgactt cggttgccgc gtggacccag cctatcggac ggtcggcggt      420
tacgggcacg tcgattgtaa ctataagctc cttgtggaca accttatgga tttgggccac      480
gctcagtacg tgcaccgggc taacgctcag actgacgcct tgaccgtct cgaaagggag       540
gtcatcgtcg gcgacggaga gattcaggcg ctgatgaaga tccctggagg cacgccctct      600
gtgctcatgg cgaagtttct cagaggcgcg aacacgcccg tggacgcctg aacgacatc       660
cgctggaata aggtctccgc gatgctgaac ttcatcgccg ttgcgcccga gggcacaccc      720
aaagagcagt caatccacag cagagggacc catattctta caccggaaac cgaggctagt      780
tgccactact tcttcggctc gtcacggaat ttcgggatag cgatccgga gatggacggt        840
gttcttcgat cttggcaagc gcaagctctc gtcaaggaag ataaggtggt cgtggaggct      900
atcgagcgta ggcgcgccta cgttgaggcg aacggtatta gcccgcgat gctgtcctgc       960
gacgaggccg cagttagagt gtcgcgcgag atagaaaagc tggagcagct agaggccgcc     1020
tga                                                                   1023
```

<210> SEQ ID NO 37
<211> LENGTH: 1020

<210> SEQ ID NO 37
<211> LENGTH: 1020
<212> TYPE: DNA
<213> ORGANISM: Artificial Sequence
<220> FEATURE:
<223> OTHER INFORMATION: Recombinant

<400> SEQUENCE: 37

```
atgctcactt tcgttagaaa cgcttggtac gttgctgcac ttcctgagga gttgagcgag      60
aagcctctag gaagaactat cctcgatact ccactagctc tctatcgtca acctgacgga     120
gttgtcgctg ccctgcttga tatttgtccg catcgcttcg ctccgttgag tgacggtatt     180
ctagtcaacg acatctcca gtgtccatat cacggtctgg aatttgacgg aggtggccag     240
tgtgtccaca acccgctcgg caacggagcc cgccctgctt ctctgaacgt gcgatcattc     300
cctgtcgtgg aaagagacgc attgatctgg atctggcctg agatccagc actcgcagat      360
cccggtgcta tccctgactt tgggtgtcgt gttgatccag cttaccgtac tgtcggaggt     420
tacggtcacg tggactgcaa ctacaagctc cttgtggata acctcatgga tcttggacac     480
gctcagtacg tgcaccgcgc taacgcccaa acagacgcct tcgatagact tgagcgtgag     540
gtgatcaaag gcgacggcga gatccaggcg ctcatgaaga tccctggtgg cacaccctca     600
gttctcatgg ctaagttctt tgcgtggtgct aacacaccag ttgacgcctg gaacgacatc     660
cggtggaata aggtgtcggc tatgctgaac ttcatcgcgg tcgcgccgga agggacgccg     720
aaggagcagt caatccactc ccgaggaacc catatcctta ctcctgagac cgaggcaagc     780
tgccattact tcttcggtag ttcccgcaac ttcggtatag acgatccaga gatggacggt     840
gttctcagga gctggcaagc tcaagccctg gtgaaggagg acaaagtggt cgttgaagct     900
atcgaaaggc ggagggctta cgtcgaagcg aacgggatca gacccgccat gttgtcctgc     960
gacgaggcag ccgtcagggt atccaggag attgagaagc tcgaacaact agaagcggcg    1020
```

<210> SEQ ID NO 38
<211> LENGTH: 35
<212> TYPE: PRT
<213> ORGANISM: Gossypium raimondii

<400> SEQUENCE: 38

Met Leu Asn Ile Ala Pro Ser Cys Val Leu Ala Ser Gly Ile Ser Lys
1               5                   10                  15

Pro Val Thr Lys Met Ala Ser Thr Glu Asn Lys Asp Asp His Ser Ser
            20                  25                  30

Ala Lys Arg
        35

<210> SEQ ID NO 39
<211> LENGTH: 105
<212> TYPE: DNA
<213> ORGANISM: Artificial Sequence
<220> FEATURE:
<223> OTHER INFORMATION: Recombinant

<400> SEQUENCE: 39

```
atgcttaaca ttgcgccgag ttgtgttttg ccagcgggga tctctaagcc cgtgaccaag      60
atggctagca cggagaacaa ggacgaccac agcagcgcca agagg                     105
```

<210> SEQ ID NO 40
<211> LENGTH: 179
<212> TYPE: PRT
<213> ORGANISM: Enterobacter cloacae

<400> SEQUENCE: 40

Met Lys Ala Leu Val Leu Tyr Ser Thr Arg Asp Gly Gln Thr His Ala
1               5                   10                  15

Ile Ala Ser Tyr Ile Ala Ser Cys Met Lys Glu Lys Ala Glu Cys Asp
                20                  25                  30

Val Ile Asp Leu Thr His Gly Glu His Val Asn Leu Thr Gln Tyr Asp
            35                  40                  45

Gln Val Leu Ile Gly Ala Ser Ile Arg Tyr Gly His Phe Asn Ala Val
        50                  55                  60

Leu Asp Lys Phe Ile Lys Arg Asn Val Asp Gln Leu Asn Asn Met Pro
65                  70                  75                  80

Ser Ala Phe Phe Cys Val Asn Leu Thr Ala Arg Lys Pro Glu Lys Arg
                85                  90                  95

Thr Pro Gln Thr Asn Pro Tyr Val Arg Lys Phe Leu Leu Ala Thr Pro
            100                 105                 110

Trp Gln Pro Ala Leu Cys Gly Val Phe Ala Gly Ala Leu Arg Tyr Pro
        115                 120                 125

Arg Tyr Arg Trp Ile Asp Lys Val Met Ile Gln Leu Ile Met Arg Met
        130                 135                 140

Thr Gly Gly Glu Thr Asp Thr Ser Lys Glu Val Glu Tyr Thr Asp Trp
145                 150                 155                 160

Glu Gln Val Lys Lys Phe Ala Glu Asp Phe Ala Lys Leu Ser Tyr Lys
                165                 170                 175

Lys Ala Leu

<210> SEQ ID NO 41
<211> LENGTH: 178
<212> TYPE: PRT
<213> ORGANISM: Pantoea ananatis

<400> SEQUENCE: 41

Met Lys Ala Leu Ile Leu Phe Ser Thr Arg Asp Gly Gln Thr Gln Lys
1               5                   10                  15

Ile Ala Ser Ala Ile Ala Asp Glu Ile Lys Gly Gln Gln Ser Cys Asp
                20                  25                  30

Val Ile Asn Ile Gln Asp Ala Lys Thr Leu Asp Trp Gln Gln Tyr Asp
            35                  40                  45

Arg Val Leu Ile Gly Ala Ser Ile Arg Tyr Gly His Phe Gln Pro Val
        50                  55                  60

Val Asn Glu Phe Val Lys His Asn Leu Leu Ala Leu Gln Gln Arg Val
65                  70                  75                  80

Ser Gly Phe Phe Ser Val Asn Leu Thr Ala Arg Lys Pro Glu Lys Arg
                85                  90                  95

Ser Pro Glu Thr Asn Ala Tyr Thr Val Lys Phe Leu Ala Gln Ser Pro
            100                 105                 110

Trp Gln Pro Asp Cys Cys Ala Val Phe Ala Gly Ala Leu Tyr Tyr Pro
        115                 120                 125

Arg Tyr Arg Trp Phe Asp Arg Val Met Ile Gln Phe Ile Met Arg Met
        130                 135                 140

Thr Gly Gly Glu Thr Asp Ala Ser Lys Glu Val Glu Tyr Thr Asp Trp
145                 150                 155                 160

Gln Gln Val Gln Arg Phe Ala Arg Asp Phe Ala Gln Leu Pro Gly Lys
                165                 170                 175

Ser Tyr

<210> SEQ ID NO 42
<211> LENGTH: 177
<212> TYPE: PRT
<213> ORGANISM: Pantoea stewardii

<400> SEQUENCE: 42

```
Met Lys Ala Leu Ile Leu Tyr Ser Thr Arg Asp Gly Gln Thr Arg Lys
1               5                   10                  15

Ile Ala Ser Ser Ile Ala Asp Val Ile Arg Gln Gln Gln Cys Asp
            20                  25                  30

Val Leu Asn Ile Lys Asp Ala Ser Leu Pro Asp Trp Ala Gln Tyr Asp
        35                  40                  45

Arg Val Leu Ile Gly Ala Ser Ile Arg Tyr Gly His Phe Gln Pro Val
    50                  55                  60

Val Asp Lys Phe Val Lys Gln His Leu His Glu Leu Gln Gln Arg Thr
65                  70                  75                  80

Ser Gly Phe Phe Ser Val Asn Leu Thr Ala Arg Lys Pro Glu Lys Arg
                85                  90                  95

Ser Pro Glu Thr Asn Ala Tyr Thr Gln Lys Phe Leu Ala His Ser Pro
            100                 105                 110

Trp Gln Pro Asp Cys Cys Ala Val Phe Ala Gly Ala Leu Tyr Tyr Pro
        115                 120                 125

Arg Tyr Arg Trp Phe Asp Arg Val Met Ile Gln Leu Ile Met Arg Met
    130                 135                 140

Thr Gly Gly Glu Thr Asp Ser Thr Lys Glu Val Glu Tyr Thr Asp Trp
145                 150                 155                 160

Gln Gln Val Ser Thr Phe Ala Asn Asp Phe Ala Gln Leu Pro Gly Lys
                165                 170                 175

Ser
```

<210> SEQ ID NO 43
<211> LENGTH: 181
<212> TYPE: PRT
<213> ORGANISM: Escherichia coli

<400> SEQUENCE: 43

```
Met Lys Thr Leu Ile Leu Phe Ser Thr Arg Asp Gly Gln Thr Arg Glu
1               5                   10                  15

Ile Ala Ser Tyr Leu Ala Ser Glu Leu Lys Glu Leu Gly Ile Gln Ala
            20                  25                  30

Asp Val Ala Asn Val His Arg Ile Glu Glu Pro Gln Trp Glu Asn Tyr
        35                  40                  45

Asp Arg Val Val Ile Gly Ala Ser Ile Arg Tyr Gly His Tyr His Ser
    50                  55                  60

Ala Phe Gln Glu Phe Val Lys Lys His Ala Thr Arg Leu Asn Ser Met
65                  70                  75                  80

Pro Ser Ala Phe Tyr Ser Val Asn Leu Val Ala Arg Lys Pro Glu Lys
                85                  90                  95

Arg Thr Pro Gln Thr Asn Ser Tyr Ala Arg Lys Phe Leu Met Asn Ser
            100                 105                 110

Gln Trp Arg Pro Asp Arg Cys Ala Val Ile Ala Gly Ala Leu Arg Tyr
        115                 120                 125

Pro Arg Tyr Arg Trp Tyr Asp Arg Phe Met Ile Lys Leu Ile Met Lys
    130                 135                 140

Met Ser Gly Gly Glu Thr Asp Thr Arg Lys Glu Val Val Tyr Thr Asp
```

```
                145                 150                 155                 160
Trp Glu Gln Val Ala Asn Phe Ala Arg Glu Ile Ala His Leu Thr Asp
                    165                 170                 175
Lys Pro Thr Leu Lys
            180

<210> SEQ ID NO 44
<211> LENGTH: 178
<212> TYPE: PRT
<213> ORGANISM: Erwinia toletana

<400> SEQUENCE: 44

Met Lys Ala Leu Ile Leu Phe Ser Ser Arg Glu Gly Gln Thr Arg Glu
1               5                   10                  15

Ile Ala Ser Tyr Ile Ala Asn Ser Ile Lys Glu Glu Met Glu Cys Asp
                20                  25                  30

Val Phe Asn Ile Leu Arg Val Glu Gln Ile Asp Trp Ser Gln Tyr Asp
            35                  40                  45

Arg Val Leu Ile Gly Gly Ser Ile His Tyr Gly His Phe His Pro Ala
        50                  55                  60

Val Ala Lys Phe Val Lys Arg His Leu His Glu Leu Gln Gln Arg Ser
65                  70                  75                  80

Ser Gly Phe Phe Cys Val Asn Leu Thr Ala Arg Lys Ala Asp Lys Arg
                85                  90                  95

Thr Pro Gln Thr Asn Ala Tyr Met Arg Lys Phe Leu Leu Gln Ser Pro
            100                 105                 110

Trp Gln Pro Asp Cys Cys Ala Val Phe Ala Gly Ala Leu Arg Tyr Thr
        115                 120                 125

Arg Tyr Arg Trp Phe Asp Arg Val Met Ile Gln Leu Ile Met Arg Met
    130                 135                 140

Thr Gly Gly Glu Thr Asp Thr Ser Lys Glu Val Glu Tyr Thr Asp Trp
145                 150                 155                 160

Thr Gln Val Ala Arg Phe Ala Gln Glu Phe Ala His Leu Pro Gly Lys
                165                 170                 175

Thr Gln

<210> SEQ ID NO 45
<211> LENGTH: 179
<212> TYPE: PRT
<213> ORGANISM: Pectobacterium carotovorum

<400> SEQUENCE: 45

Met Lys Ala Leu Ile Val Phe Ser Ser Arg Asp Gly Gln Thr Arg Ala
1               5                   10                  15

Ile Ala Ser Tyr Ile Ala Asn Thr Leu Lys Gly Thr Leu Glu Cys Asp
                20                  25                  30

Val Val Asn Val Leu Asn Ala Asn Asp Ile Asp Leu Ser Gln Tyr Asp
            35                  40                  45

Arg Val Ala Ile Gly Ala Ser Ile Arg Tyr Gly Arg Phe His Pro Ala
        50                  55                  60

Val Asn Gln Phe Ile Arg Lys His Leu Thr Ser Leu Gln Gln Leu Pro
65                  70                  75                  80

Ser Ala Phe Phe Ser Val Asn Leu Thr Ala Arg Lys Pro Glu Lys Arg
                85                  90                  95

Thr Ile Gln Thr Asn Ala Tyr Thr Arg Lys Phe Leu Leu Asn Ser Pro
            100                 105                 110
```

```
Trp Gln Pro Asp Leu Cys Cys Val Phe Ala Gly Ala Leu Arg Tyr Pro
            115                 120                 125

Arg Tyr Arg Trp Phe Asp Arg Val Met Ile Gln Leu Ile Met Arg Ile
        130                 135                 140

Thr Gly Gly Glu Thr Asp Ser Thr Lys Glu Ile Glu Tyr Thr Asp Trp
145                 150                 155                 160

Gln Gln Val Ala Arg Phe Ala Gln Asp Phe Ala Gln Leu Ala Ala Lys
                165                 170                 175

Asn Pro Ala

<210> SEQ ID NO 46
<211> LENGTH: 179
<212> TYPE: PRT
<213> ORGANISM: Shimwellia blattae

<400> SEQUENCE: 46

Met Lys Thr Leu Ile Leu Phe Ser Thr Arg Asp Gly Gln Thr His Lys
1               5                   10                  15

Ile Ala Arg His Ile Ala Gly Val Leu Glu Glu Gln Gly Lys Ala Cys
            20                  25                  30

Glu Leu Val Asp Leu Leu Gln Pro Gly Glu Pro Asp Trp Ser Thr Val
        35                  40                  45

Glu Cys Val Val Leu Gly Ala Ser Ile Arg Tyr Gly His Phe His Lys
    50                  55                  60

Ser Phe Ile Arg Phe Val Asn Thr His Ala Gln Arg Leu Asn Asn Met
65                  70                  75                  80

Pro Gly Ala Leu Phe Thr Val Asn Leu Val Ala Arg Lys Pro Glu Lys
                85                  90                  95

Gln Ser Pro Gln Thr Asn Ser Tyr Thr Arg Lys Phe Leu Ala Ala Ser
            100                 105                 110

Pro Trp Gln Pro Gln Arg Cys Gln Val Phe Ala Gly Ala Leu Arg Tyr
        115                 120                 125

Pro Arg Tyr Ser Trp Tyr Asp Arg Met Met Ile Arg Leu Ile Met Lys
    130                 135                 140

Met Ala Gly Gly Glu Thr Asp Thr Arg Lys Glu Val Glu Tyr Thr Asp
145                 150                 155                 160

Trp Gln Ser Val Thr Arg Phe Ala Arg Glu Ile Ala Gln Leu Pro Gly
                165                 170                 175

Glu Thr Arg

<210> SEQ ID NO 47
<211> LENGTH: 178
<212> TYPE: PRT
<213> ORGANISM: Pantoea stewardii

<400> SEQUENCE: 47

Met Lys Ala Leu Ile Leu Phe Ser Ser Arg Asp Gly Gln Thr Gln Leu
1               5                   10                  15

Ile Ala Ser Ser Ile Ala Lys Glu Leu Glu Gly Lys Gln Ala Cys Asp
            20                  25                  30

Val Leu Asn Ile Leu Asp Thr Thr Asn Val Glu Trp Thr Gln Tyr Asp
        35                  40                  45

Arg Val Leu Ile Gly Ala Ser Ile Arg Tyr Gly His Phe His Pro Ala
    50                  55                  60

Val Ala Glu Phe Val Lys Arg His Gln Arg Glu Leu Gln Gln Arg Ser
```

```
                65                  70                  75                  80
Ser Gly Phe Phe Ser Val Asn Leu Thr Ala Arg Lys Pro Glu Lys Arg
                    85                  90                  95

Ser Pro Glu Thr Asn Ala Tyr Thr Ala Lys Phe Leu Asn Gln Ser Pro
                100                 105                 110

Trp Gln Pro Asp Cys Cys Ala Val Phe Ala Gly Ala Leu Arg Tyr Pro
            115                 120                 125

Arg Tyr Arg Trp Phe Asp Arg Ile Met Ile Gln Leu Ile Met Arg Met
        130                 135                 140

Thr Gly Gly Glu Thr Asp Ser Ser Lys Glu Val Glu Tyr Thr Asp Trp
145                 150                 155                 160

Gln Gln Val Thr Arg Phe Ala Gln Glu Phe Ala Arg Leu Pro Gly Lys
                165                 170                 175

Thr Ser

<210> SEQ ID NO 48
<211> LENGTH: 180
<212> TYPE: PRT
<213> ORGANISM: Enterobacter cloacae

<400> SEQUENCE: 48

Met Lys Thr Leu Ile Leu Phe Ser Thr Arg Asp Gly Gln Thr Arg Glu
1               5                   10                  15

Ile Ala Ala Phe Leu Ala Ser Glu Leu Lys Glu Gln Gly Ile Tyr Ala
                20                  25                  30

Asp Val Ile Asn Leu Asn Arg Thr Glu Glu Ile Ala Trp Gln Glu Tyr
            35                  40                  45

Asp Arg Val Val Ile Gly Ala Ser Ile Arg Tyr Gly His Phe His Pro
        50                  55                  60

Ala Val Asp Arg Phe Val Lys Lys His Thr Glu Thr Leu Asn Ser Leu
65                  70                  75                  80

Pro Gly Ala Phe Phe Ser Val Asn Leu Val Ala Arg Lys Ala Glu Lys
                85                  90                  95

Arg Thr Pro Gln Thr Asn Ser Tyr Thr Arg Lys Phe Leu Leu Asn Ser
                100                 105                 110

Pro Trp Lys Pro Ala Ala Cys Ala Val Phe Ala Gly Ala Leu Arg Tyr
            115                 120                 125

Pro Arg Tyr Arg Trp Tyr Asp Arg Phe Met Ile Arg Leu Ile Met Lys
        130                 135                 140

Met Thr Gly Gly Glu Thr Asp Thr Arg Lys Glu Val Val Tyr Thr Asp
145                 150                 155                 160

Trp Ser Gln Val Ala Ser Phe Ala Arg Glu Ile Val Gln Leu Thr Arg
                165                 170                 175

Ser Ser Arg Leu
            180

<210> SEQ ID NO 49
<211> LENGTH: 177
<212> TYPE: PRT
<213> ORGANISM: Enterobacter mori

<400> SEQUENCE: 49

Met Lys Ile Leu Ile Leu Phe Ser Thr Arg Asp Gly Gln Thr Arg Glu
1               5                   10                  15

Ile Ala Ala Ser Leu Ala Ser Glu Leu Lys Glu Gln Ala Phe Asp Val
                20                  25                  30
```

```
Asp Val Val Asn Leu His Arg Ala Glu Asn Ile Ala Trp Glu Glu Tyr
        35                  40                  45

Asp Gly Val Val Ile Gly Ala Ser Ile Arg Tyr Gly His Phe His Ser
    50                  55                  60

Thr Leu Asn Ser Phe Val Lys His Gln Gln Ala Leu Lys Lys Leu
65                  70                  75                  80

Pro Gly Ala Phe Tyr Ser Val Asn Leu Val Ala Arg Lys Pro Glu Lys
                85                  90                  95

Arg Thr Pro Gln Thr Asn Ser Tyr Thr Arg Lys Phe Leu Leu Asp Ser
                100                 105                 110

Pro Trp Gln Pro Asp Leu Ser Ala Val Phe Ala Gly Ala Leu Arg Tyr
                115                 120                 125

Pro Arg Tyr Asn Trp Tyr Asp Arg Ile Met Ile Arg Leu Ile Met Lys
            130                 135                 140

Ile Thr Gly Gly Glu Thr Asp Thr Arg Lys Glu Val Val Tyr Thr Asp
145                 150                 155                 160

Trp Gln Gln Val Thr His Phe Ala His Glu Ile Val Gln Leu Val Arg
                165                 170                 175

Lys

<210> SEQ ID NO 50
<211> LENGTH: 178
<212> TYPE: PRT
<213> ORGANISM: Enterobacter cloacae

<400> SEQUENCE: 50

Lys Ala Leu Val Leu Tyr Ser Thr Arg Asp Gly Gln Thr His Ala Ile
1               5                   10                  15

Ala Ser Tyr Ile Ala Ser Cys Met Lys Glu Lys Ala Glu Cys Asp Val
                20                  25                  30

Ile Asp Leu Thr His Gly Glu His Val Asn Leu Thr Gln Tyr Asp Gln
            35                  40                  45

Val Leu Ile Gly Ala Ser Ile Arg Tyr Gly His Phe Asn Ala Val Leu
    50                  55                  60

Asp Lys Phe Ile Lys Arg Asn Val Asp Gln Leu Asn Asn Met Pro Ser
65                  70                  75                  80

Ala Phe Phe Cys Val Asn Leu Thr Ala Arg Lys Pro Glu Lys Arg Thr
                85                  90                  95

Pro Gln Thr Asn Pro Tyr Val Arg Lys Phe Leu Leu Ala Thr Pro Trp
                100                 105                 110

Gln Pro Ala Leu Cys Gly Val Phe Ala Gly Ala Leu Arg Tyr Pro Arg
                115                 120                 125

Tyr Arg Trp Ile Asp Lys Val Met Ile Gln Leu Ile Met Arg Met Thr
            130                 135                 140

Gly Gly Glu Thr Asp Thr Ser Lys Glu Val Glu Tyr Thr Asp Trp Glu
145                 150                 155                 160

Gln Val Lys Lys Phe Ala Glu Asp Phe Ala Lys Leu Ser Tyr Lys Lys
                165                 170                 175

Ala Leu

<210> SEQ ID NO 51
<211> LENGTH: 177
<212> TYPE: PRT
<213> ORGANISM: Pantoea ananatis
```

<400> SEQUENCE: 51

```
Lys Ala Leu Ile Leu Phe Ser Thr Arg Asp Gly Gln Thr Gln Lys Ile
1               5                   10                  15

Ala Ser Ala Ile Ala Asp Glu Ile Lys Gly Gln Gln Ser Cys Asp Val
            20                  25                  30

Ile Asn Ile Gln Asp Ala Lys Thr Leu Asp Trp Gln Gln Tyr Asp Arg
        35                  40                  45

Val Leu Ile Gly Ala Ser Ile Arg Tyr Gly His Phe Gln Pro Val Val
    50                  55                  60

Asn Glu Phe Val Lys His Asn Leu Leu Ala Leu Gln Gln Arg Val Ser
65                  70                  75                  80

Gly Phe Phe Ser Val Asn Leu Thr Ala Arg Lys Pro Glu Lys Arg Ser
                85                  90                  95

Pro Glu Thr Asn Ala Tyr Thr Val Lys Phe Leu Ala Gln Ser Pro Trp
            100                 105                 110

Gln Pro Asp Cys Cys Ala Val Phe Ala Gly Ala Leu Tyr Tyr Pro Arg
        115                 120                 125

Tyr Arg Trp Phe Asp Arg Val Met Ile Gln Phe Ile Met Arg Met Thr
    130                 135                 140

Gly Gly Glu Thr Asp Ala Ser Lys Glu Val Glu Tyr Thr Asp Trp Gln
145                 150                 155                 160

Gln Val Gln Arg Phe Ala Arg Asp Phe Ala Gln Leu Pro Gly Lys Ser
                165                 170                 175

Tyr
```

<210> SEQ ID NO 52
<211> LENGTH: 180
<212> TYPE: PRT
<213> ORGANISM: Escherichia coli

<400> SEQUENCE: 52

```
Lys Thr Leu Ile Leu Phe Ser Thr Arg Asp Gly Gln Thr Arg Glu Ile
1               5                   10                  15

Ala Ser Tyr Leu Ala Ser Glu Leu Lys Glu Leu Gly Ile Gln Ala Asp
            20                  25                  30

Val Ala Asn Val His Arg Ile Glu Glu Pro Gln Trp Glu Asn Tyr Asp
        35                  40                  45

Arg Val Val Ile Gly Ala Ser Ile Arg Tyr Gly His Tyr His Ser Ala
    50                  55                  60

Phe Gln Glu Phe Val Lys Lys His Ala Thr Arg Leu Asn Ser Met Pro
65                  70                  75                  80

Ser Ala Phe Tyr Ser Val Asn Leu Val Ala Arg Lys Pro Glu Lys Arg
                85                  90                  95

Thr Pro Gln Thr Asn Ser Tyr Ala Arg Lys Phe Leu Met Asn Ser Gln
            100                 105                 110

Trp Arg Pro Asp Arg Cys Ala Val Ile Ala Gly Ala Leu Arg Tyr Pro
        115                 120                 125

Arg Tyr Arg Trp Tyr Asp Arg Phe Met Ile Lys Leu Ile Met Lys Met
    130                 135                 140

Ser Gly Gly Glu Thr Asp Thr Arg Lys Glu Val Val Tyr Thr Asp Trp
145                 150                 155                 160

Glu Gln Val Ala Asn Phe Ala Arg Glu Ile Ala His Leu Thr Asp Lys
                165                 170                 175

Pro Thr Leu Lys
```

180

<210> SEQ ID NO 53
<211> LENGTH: 177
<212> TYPE: PRT
<213> ORGANISM: Erwinia toletana

<400> SEQUENCE: 53

Lys Ala Leu Ile Leu Phe Ser Ser Arg Glu Gly Gln Thr Arg Glu Ile
1               5                   10                  15

Ala Ser Tyr Ile Ala Asn Ser Ile Lys Glu Glu Met Glu Cys Asp Val
            20                  25                  30

Phe Asn Ile Leu Arg Val Glu Gln Ile Asp Trp Ser Gln Tyr Asp Arg
        35                  40                  45

Val Leu Ile Gly Gly Ser Ile His Tyr Gly His Phe His Pro Ala Val
    50                  55                  60

Ala Lys Phe Val Lys Arg His Leu His Glu Leu Gln Gln Arg Ser Ser
65                  70                  75                  80

Gly Phe Phe Cys Val Asn Leu Thr Ala Arg Lys Ala Asp Lys Arg Thr
                85                  90                  95

Pro Gln Thr Asn Ala Tyr Met Arg Lys Phe Leu Leu Ser Pro Trp
            100                 105                 110

Gln Pro Asp Cys Cys Ala Val Phe Ala Gly Ala Leu Arg Tyr Thr Arg
        115                 120                 125

Tyr Arg Trp Phe Asp Arg Val Met Ile Gln Leu Ile Met Arg Met Thr
    130                 135                 140

Gly Gly Glu Thr Asp Thr Ser Lys Glu Val Glu Tyr Thr Asp Trp Thr
145                 150                 155                 160

Gln Val Ala Arg Phe Ala Gln Glu Phe Ala His Leu Pro Gly Lys Thr
                165                 170                 175

Gln

<210> SEQ ID NO 54
<211> LENGTH: 178
<212> TYPE: PRT
<213> ORGANISM: Pectobacterium carotovorum

<400> SEQUENCE: 54

Lys Ala Leu Ile Val Phe Ser Ser Arg Asp Gly Gln Thr Arg Ala Ile
1               5                   10                  15

Ala Ser Tyr Ile Ala Asn Thr Leu Lys Gly Thr Leu Glu Cys Asp Val
            20                  25                  30

Val Asn Val Leu Asn Ala Asn Asp Ile Asp Leu Ser Gln Tyr Asp Arg
        35                  40                  45

Val Ala Ile Gly Ala Ser Ile Arg Tyr Gly Arg Phe His Pro Ala Val
    50                  55                  60

Asn Gln Phe Ile Arg Lys His Leu Thr Ser Leu Gln Gln Leu Pro Ser
65                  70                  75                  80

Ala Phe Phe Ser Val Asn Leu Thr Ala Arg Lys Pro Glu Lys Arg Thr
                85                  90                  95

Ile Gln Thr Asn Ala Tyr Thr Arg Lys Phe Leu Leu Asn Ser Pro Trp
            100                 105                 110

Gln Pro Asp Leu Cys Cys Val Phe Ala Gly Ala Leu Arg Tyr Pro Arg
        115                 120                 125

Tyr Arg Trp Phe Asp Arg Val Met Ile Gln Leu Ile Met Arg Ile Thr
    130                 135                 140

```
Gly Gly Glu Thr Asp Ser Thr Lys Glu Ile Glu Tyr Thr Asp Trp Gln
145                 150                 155                 160

Gln Val Ala Arg Phe Ala Gln Asp Phe Ala Gln Leu Ala Ala Lys Asn
                165                 170                 175

Pro Ala

<210> SEQ ID NO 55
<211> LENGTH: 178
<212> TYPE: PRT
<213> ORGANISM: Shimwellia blattae

<400> SEQUENCE: 55

Lys Thr Leu Ile Leu Phe Ser Thr Arg Asp Gly Gln Thr His Lys Ile
1               5                   10                  15

Ala Arg His Ile Ala Gly Val Leu Glu Glu Gly Lys Ala Cys Glu
                20                  25                  30

Leu Val Asp Leu Leu Gln Pro Gly Glu Pro Asp Trp Ser Thr Val Glu
            35                  40                  45

Cys Val Val Leu Gly Ala Ser Ile Arg Tyr Gly His Phe His Lys Ser
        50                  55                  60

Phe Ile Arg Phe Val Asn Thr His Ala Gln Arg Leu Asn Asn Met Pro
65                  70                  75                  80

Gly Ala Leu Phe Thr Val Asn Leu Val Ala Arg Lys Pro Glu Lys Gln
                85                  90                  95

Ser Pro Gln Thr Asn Ser Tyr Thr Arg Lys Phe Leu Ala Ala Ser Pro
                100                 105                 110

Trp Gln Pro Gln Arg Cys Gln Val Phe Ala Gly Ala Leu Arg Tyr Pro
            115                 120                 125

Arg Tyr Ser Trp Tyr Asp Arg Met Met Ile Arg Leu Ile Met Lys Met
        130                 135                 140

Ala Gly Gly Glu Thr Asp Thr Arg Lys Glu Val Glu Tyr Thr Asp Trp
145                 150                 155                 160

Gln Ser Val Thr Arg Phe Ala Arg Glu Ile Ala Gln Leu Pro Gly Glu
                165                 170                 175

Thr Arg

<210> SEQ ID NO 56
<211> LENGTH: 179
<212> TYPE: PRT
<213> ORGANISM: Enterobacter cloacae

<400> SEQUENCE: 56

Lys Thr Leu Ile Leu Phe Ser Thr Arg Asp Gly Gln Thr Arg Glu Ile
1               5                   10                  15

Ala Ala Phe Leu Ala Ser Glu Leu Lys Glu Gln Gly Ile Tyr Ala Asp
                20                  25                  30

Val Ile Asn Leu Asn Arg Thr Glu Glu Ile Ala Trp Gln Glu Tyr Asp
            35                  40                  45

Arg Val Val Ile Gly Ala Ser Ile Arg Tyr Gly His Phe His Pro Ala
        50                  55                  60

Val Asp Arg Phe Val Lys Lys His Thr Glu Thr Leu Asn Ser Leu Pro
65                  70                  75                  80

Gly Ala Phe Phe Ser Val Asn Leu Val Ala Arg Lys Ala Glu Lys Arg
                85                  90                  95

Thr Pro Gln Thr Asn Ser Tyr Thr Arg Lys Phe Leu Leu Asn Ser Pro
```

```
              100                 105                 110
Trp Lys Pro Ala Ala Cys Ala Val Phe Ala Gly Ala Leu Arg Tyr Pro
            115                 120                 125

Arg Tyr Arg Trp Tyr Asp Arg Phe Met Ile Arg Leu Ile Met Lys Met
        130                 135                 140

Thr Gly Gly Glu Thr Asp Thr Arg Lys Glu Val Val Tyr Thr Asp Trp
145                 150                 155                 160

Ser Gln Val Ala Ser Phe Ala Arg Glu Ile Val Gln Leu Thr Arg Ser
                165                 170                 175

Ser Arg Leu

<210> SEQ ID NO 57
<211> LENGTH: 178
<212> TYPE: PRT
<213> ORGANISM: Artificial Sequence
<220> FEATURE:
<223> OTHER INFORMATION: Recombinant

<400> SEQUENCE: 57

Lys Ala Leu Val Leu Tyr Ser Thr Arg Asp Gly Gln Thr His Ala Ile
1               5                   10                  15

Ala Ser Tyr Ile Ala Ser Cys Met Lys Glu Lys Ala Glu Cys Asp Val
                20                  25                  30

Ile Asp Leu Thr His Gly Glu His Val Asn Leu Thr Gln Tyr Asp Gln
            35                  40                  45

Val Leu Ile Gly Ala Asn Ile Arg Tyr Gly His Phe Asn Ala Val Leu
        50                  55                  60

Asp Lys Phe Ile Lys Arg Asn Val Asp Gln Leu Asn Asn Met Pro Ser
65                  70                  75                  80

Ala Phe Phe Cys Val Asn Leu Thr Ala Arg Lys Pro Glu Lys Arg Thr
                85                  90                  95

Pro Gln Thr Asn Pro Tyr Val Arg Lys Phe Leu Leu Ala Thr Pro Trp
            100                 105                 110

Gln Pro Ala Leu Cys Gly Val Phe Ala Gly Ala Leu Arg Tyr Pro Arg
        115                 120                 125

Tyr Arg Trp Ile Asp Lys Val Met Ile Gln Leu Ile Met Arg Met Thr
130                 135                 140

Gly Gly Glu Thr Asp Thr Ser Lys Glu Val Glu Tyr Thr Asp Trp Glu
145                 150                 155                 160

Gln Val Lys Lys Phe Ala Glu Asp Phe Ala Lys Leu Ser Tyr Lys Lys
                165                 170                 175

Ala Leu

<210> SEQ ID NO 58
<211> LENGTH: 172
<212> TYPE: PRT
<213> ORGANISM: Artificial Sequence
<220> FEATURE:
<223> OTHER INFORMATION: Recombinant

<400> SEQUENCE: 58

Lys Ala Leu Val Leu Tyr Ser Thr Arg Asp Gly Gln Thr His Ala Ile
1               5                   10                  15

Ala Ser Tyr Ile Ala Ser Cys Met Lys Glu Lys Ala Glu Cys Asp Val
                20                  25                  30

Ile Asp Leu Thr His Gly Glu His Val Asn Leu Thr Gln Tyr Asp Gln
            35                  40                  45
```

```
Val Leu Ile Gly Ala Ser Ile Arg Tyr Gly His Phe Asn Ala Val Leu
    50                  55                  60

Asp Lys Phe Ile Lys Arg Asn Val Asp Gln Leu Asn Asn Met Pro Ser
65                  70                  75                  80

Ala Phe Phe Cys Val Asn Leu Thr Ala Arg Lys Pro Glu Lys Arg Thr
                85                  90                  95

Pro Gln Thr Asn Pro Tyr Val Arg Lys Phe Leu Leu Ala Thr Pro Trp
                100                 105                 110

Gln Pro Ala Leu Cys Gly Val Phe Ala Gly Ala Leu Arg Tyr Pro Arg
                115                 120                 125

Tyr Arg Trp Ile Asp Lys Val Met Ile Gln Leu Ile Met Arg Met Thr
        130                 135                 140

Gly Gly Glu Thr Asp Thr Ser Lys Glu Val Glu Tyr Thr Asp Trp Glu
145                 150                 155                 160

Gln Val Lys Lys Phe Ala Glu Asp Phe Ala Lys Leu
                165                 170
```

<210> SEQ ID NO 59
<211> LENGTH: 179
<212> TYPE: PRT
<213> ORGANISM: Artificial Sequence
<220> FEATURE:
<223> OTHER INFORMATION: Recombinant

<400> SEQUENCE: 59

```
Lys Thr Leu Ile Leu Phe Ser Thr Arg Asp Gly Gln Thr Arg Glu Ile
1               5                   10                  15

Ala Ala Phe Leu Ala Ser Glu Leu Lys Glu Gln Gly Ile Tyr Ala Asp
                20                  25                  30

Val Ile Asn Leu Asn Arg Thr Glu Glu Ile Ala Trp Gln Glu Tyr Asp
            35                  40                  45

Arg Val Val Ile Gly Ala Ser Ile Arg Tyr Gly His Phe His Pro Ala
    50                  55                  60

Val Asp Arg Phe Val Lys Lys His Thr Glu Thr Leu Asn Ser Leu Pro
65                  70                  75                  80

Gly Ala Phe Phe Ser Val Asn Leu Val Ala Arg Lys Ala Glu Lys Arg
                85                  90                  95

Thr Pro Gln Thr Asn Ser Tyr Thr Arg Lys Phe Leu Leu Asn Ser Pro
                100                 105                 110

Trp Lys Pro Ala Ala Cys Ala Val Phe Ala Gly Ala Leu Arg Tyr Pro
                115                 120                 125

Arg Tyr Arg Trp Tyr Asp Arg Phe Met Ile Arg Leu Ile Met Lys Met
        130                 135                 140

Thr Gly Gly Glu Thr Asp Thr Arg Lys Glu Val Val Tyr Thr Asp Trp
145                 150                 155                 160

Ser Gln Ile Ala Ser Phe Ala Arg Glu Ile Val Gln Leu Thr Arg Ser
                165                 170                 175

Ser Arg Leu
```

<210> SEQ ID NO 60
<211> LENGTH: 504
<212> TYPE: PRT
<213> ORGANISM: Amaranthus tuberculatus

<400> SEQUENCE: 60

```
Met Gly Asn Ile Ser Glu Arg Glu Glu Pro Thr Ser Ala Lys Arg Val
```

-continued

```
1               5                    10                   15
Ala Val Val Gly Ala Gly Val Ser Gly Leu Ala Ala Tyr Lys Leu
            20                   25                   30
Lys Ser His Gly Leu Ser Val Thr Leu Phe Glu Ala Asp Ser Arg Ala
            35                   40                   45
Gly Gly Lys Leu Lys Thr Val Lys Lys Asp Gly Phe Ile Trp Asp Glu
            50                   55                   60
Gly Ala Asn Thr Met Thr Glu Ser Glu Ala Glu Val Ser Ser Leu Ile
65                   70                   75                   80
Asp Asp Leu Gly Leu Arg Glu Lys Gln Gln Leu Pro Ile Ser Gln Asn
                    85                   90                   95
Lys Arg Tyr Ile Ala Arg Asp Gly Leu Pro Val Leu Leu Pro Ser Asn
                    100                  105                  110
Pro Ala Ala Leu Leu Thr Ser Asn Ile Leu Ser Ala Lys Ser Lys Leu
                    115                  120                  125
Gln Ile Met Leu Glu Pro Phe Leu Trp Arg Lys His Asn Ala Thr Glu
            130                  135                  140
Leu Ser Asp Glu His Val Gln Glu Ser Val Gly Glu Phe Phe Glu Arg
145                  150                  155                  160
His Phe Gly Lys Glu Phe Val Asp Tyr Val Ile Asp Pro Phe Val Ala
                    165                  170                  175
Gly Thr Cys Gly Gly Asp Pro Gln Ser Leu Ser Met His His Thr Phe
                    180                  185                  190
Pro Glu Val Trp Asn Ile Glu Lys Arg Phe Gly Ser Val Phe Ala Gly
                    195                  200                  205
Leu Ile Gln Ser Thr Leu Leu Ser Lys Glu Lys Gly Gly Glu Asn
210                  215                  220
Ala Ser Ile Lys Lys Pro Arg Val Arg Gly Ser Phe Ser Phe Gln Gly
225                  230                  235                  240
Gly Met Gln Thr Leu Val Asp Thr Met Cys Lys Gln Leu Gly Glu Asp
                    245                  250                  255
Glu Leu Lys Leu Gln Cys Glu Val Leu Ser Leu Ser Tyr Asn Gln Lys
                    260                  265                  270
Gly Ile Pro Ser Leu Gly Asn Trp Ser Val Ser Ser Met Ser Asn Asn
                    275                  280                  285
Thr Ser Glu Asp Gln Ser Tyr Asp Ala Val Val Thr Ala Pro Ile
            290                  295                  300
Arg Asn Val Lys Glu Met Lys Ile Met Lys Phe Gly Asn Pro Phe Ser
305                  310                  315                  320
Leu Asp Phe Ile Pro Glu Val Thr Tyr Val Pro Leu Ser Val Met Ile
                    325                  330                  335
Thr Ala Phe Lys Lys Asp Lys Val Lys Arg Pro Leu Glu Gly Phe Gly
            340                  345                  350
Val Leu Ile Pro Ser Lys Glu Gln His Asn Gly Leu Lys Thr Leu Gly
            355                  360                  365
Thr Leu Phe Ser Ser Met Met Phe Pro Asp Arg Ala Pro Ser Asp Met
            370                  375                  380
Cys Leu Phe Thr Thr Phe Val Gly Gly Ser Arg Asn Arg Lys Leu Ala
385                  390                  395                  400
Asn Ala Ser Thr Asp Glu Leu Lys Gln Ile Val Ser Ser Asp Leu Gln
                    405                  410                  415
Gln Leu Leu Gly Thr Glu Asp Glu Pro Ser Phe Val Asn His Leu Phe
            420                  425                  430
```

```
Trp Ser Asn Ala Phe Pro Leu Tyr Gly His Asn Tyr Asp Ser Val Leu
            435                 440                 445

Arg Ala Ile Asp Lys Met Glu Lys Asp Leu Pro Gly Phe Phe Tyr Ala
    450                 455                 460

Gly Asn His Lys Gly Gly Leu Ser Val Gly Lys Ala Met Ala Ser Gly
465                 470                 475                 480

Cys Lys Ala Ala Glu Leu Val Ile Ser Tyr Leu Asp Ser His Ile Tyr
                485                 490                 495

Val Lys Met Asp Glu Lys Thr Ala
            500

<210> SEQ ID NO 61
<211> LENGTH: 537
<212> TYPE: DNA
<213> ORGANISM: Artificial Sequence
<220> FEATURE:
<223> OTHER INFORMATION: Recombinant

<400> SEQUENCE: 61
atgaaagcgc tggtgctgta tagcacccgc gatggccaga cccatgcgat tgcgagctat      60
attgcgagct gcatgaaaga aaaagcggaa tgcgatgtga ttgatctgac ccatggcgaa     120
catgtgaacc tgacccagta tgatcaggtg ctgattggcg cgagcattcg ctatggccat     180
tttaacgcgg tgctggataa atttattaaa cgcaacgtgg atcagctgaa caacatgccg     240
agcgcgtttt tttgcgtgaa cctgaccgcg cgcaaaccgg aaaaacgcac cccgcagacc     300
aacccgtatg tgcgcaaatt tctgctggcg accccgtggc agccggcgct gtgcggcgtg     360
tttgcgggcg cgctgcgcta tccgcgctat cgctggattg ataaagtgat gattcagctg     420
attatgcgca tgaccggcgg cgaaaccgat accagcaaag aagtggaata taccgattgg     480
gaacaggtga aaaatttgc ggaagatttt gcgaaactga gctataaaaa agcgctg        537

<210> SEQ ID NO 62
<211> LENGTH: 534
<212> TYPE: DNA
<213> ORGANISM: Artificial Sequence
<220> FEATURE:
<223> OTHER INFORMATION: Recombinant

<400> SEQUENCE: 62
atgaaagcgc tgattctgtt tagcacccgc gatggccaga cccagaaaat tgcgagcgcg      60
attgcggatg aaattaaagg ccagcagagc tgcgatgtga ttaacattca ggatgcgaaa     120
accctggatt ggcagcagta tgatcgcgtg ctgattggcg cgagcattcg ctatggccat     180
tttcagccgg tggtgaacga atttgtgaaa cataacctgc tggcgctgca gcagcgcgtg     240
agcggctttt ttagcgtgaa cctgaccgcg cgcaaaccgg aaaaacgcag cccggaaacc     300
aacgcgtata ccgtgaaatt tctggcgcag agcccgtggc agccggattg ctgcgcggtg     360
tttgcgggcg cgctgtatta tccgcgctat cgctggtttg atcgcgtgat gattcagttt     420
attatgcgca tgaccggcgg cgaaaccgat gcgagcaaag aagtggaata taccgattgg     480
cagcaggtgc agcgctttgc gcgcgatttt gcgcagctgc gggcaaaag ctat           534

<210> SEQ ID NO 63
<211> LENGTH: 531
<212> TYPE: DNA
<213> ORGANISM: Artificial Sequence
<220> FEATURE:
<223> OTHER INFORMATION: Recombinant
```

<400> SEQUENCE: 63

```
atgaaagcgc tgattctgta tagcacccgc gatggccaga cccgcaaaat tgcgagcagc      60
attgcggatg tgattcgcca gcagcagcag tgcgatgtgc tgaacattaa agatgcgagc     120
ctgccggatt gggcgcagta tgatcgcgtg ctgattggcg cgagcattcg ctatggccat     180
tttcagccgg tggtggataa atttgtgaaa cagcatctgc atgaactgca gcagcgcacc     240
agcggctttt ttagcgtgaa cctgaccgcg cgcaaaccgg aaaaacgcag cccggaaacc     300
aacgcgtata cccagaaatt tctggcgcat agcccgtggc agccggattg ctgcgcggtg     360
tttgcgggcg cgctgtatta tccgcgctat cgctggtttg atcgcgtgat gattcagctg     420
attatgcgca tgaccggcgg cgaaaccgat agcaccaaag aagtggaata taccgattgg     480
cagcaggtga gcacctttgc gaacgatttt gcgcagctgc gggcaaaag c               531
```

<210> SEQ ID NO 64
<211> LENGTH: 546
<212> TYPE: DNA
<213> ORGANISM: Escherichia coli

<400> SEQUENCE: 64

```
gtgaaaacat taattctttt ctcaacaagg gacggacaaa cgcgcgagat tgcctcctac      60
ctggcttcgg aactgaaaga actggggatc caggcggatg tcgccaatgt gcaccgcatt     120
gaagaaccac agtgggaaaa ctatgaccgt gtggtcattg gtgcttctat cgctatggt      180
cactaccatt cagcgttcca ggaatttgtc aaaaaacatg cgacgcggct gaattcgatg     240
ccgagcgcct tttactccgt gaatctggtg gcgcgcaaac cggagaagcg tactccacag     300
accaacagct acgcgcgcaa gtttctgatg aactcgcaat ggcgtcccga tcgctgcgcg     360
gtcattgccg gggcgctgcg ttacccacgt tatcgctggt acgaccgttt tatgatcaag     420
ctgattatga agatgtcagg cggtgaaacg gatacgcgca aagaagttgt ctataccgat     480
tgggagcagg tggcgaattt cgcccgagaa atcgcccatt taaccgacaa accgacgctg     540
aaataa                                                                546
```

<210> SEQ ID NO 65
<211> LENGTH: 534
<212> TYPE: DNA
<213> ORGANISM: Artificial Sequence
<220> FEATURE:
<223> OTHER INFORMATION: Recombinant

<400> SEQUENCE: 65

```
atgaaagcgc tgattctgtt tagcagccgc gaaggccaga cccgcgaaat tgcgagctat      60
attgcgaaca gcattaaaga gaaaatggaa tgcgatgtgt taacattct gcgcgtggaa     120
cagattgatt ggagccagta tgatcgcgtg ctgattggcg cagcattca ttatggccat      180
tttcatccgg cggtggcgaa atttgtgaaa cgccatctgc atgaactgca gcagcgcagc     240
agcggctttt tttgcgtgaa cctgaccgcg cgcaaagcgg ataaacgcac cccgcagacc     300
aacgcgtata tgcgcaaatt tctgctgcag agcccgtggc agccggattg ctgcgcggtg     360
tttgcgggcg cgctgcgcta tcccgcgtat cgctggtttg atcgcgtgat gattcagctg     420
attatgcgca tgaccggcgg cgaaaccgat accagcaaag aagtggaata taccgattgg     480
acccaggtgg cgcgctttgc gcaggaattt gcgcatctgc gggcaaaaac ccag           534
```

<210> SEQ ID NO 66

<211> LENGTH: 537
<212> TYPE: DNA
<213> ORGANISM: Artificial Sequence
<220> FEATURE:
<223> OTHER INFORMATION: Recombinant

<400> SEQUENCE: 66

```
atgaaagcgc tgattgtgtt tagcagccgc gatggccaga cccgcgcgat tgcgagctat     60
attgcgaaca ccctgaaagg caccctggaa tgcgatgtgg tgaacgtgct gaacgcgaac    120
gatattgatc tgagccagta tgatcgcgtg gcgattggcg cgagcattcg ctatggccgc    180
tttcatccgg cggtgaacca gtttattcgc aaacatctga ccagcctgca gcagctgccg    240
agcgcgtttt ttagcgtgaa cctgaccgcg cgcaaaccgg aaaaacgcac cattcagacc    300
aacgcgtata cccgcaaatt tctgctgaac agcccgtggc agccggatct gtgctgcgtg    360
tttgcgggcg cgctgcgcta ccgcgctat cgctggtttg atcgcgtgat gattcagctg    420
attatgcgca ttaccggcgg cgaaaccgat agcaccaaag aaattgaata taccgattgg    480
cagcaggtgg cgcgctttgc gcaggatttt gcgcagctgg cggcgaaaaa cccggcg      537
```

<210> SEQ ID NO 67
<211> LENGTH: 537
<212> TYPE: DNA
<213> ORGANISM: Artificial Sequence
<220> FEATURE:
<223> OTHER INFORMATION: Recombinant

<400> SEQUENCE: 67

```
atgaagacct tgatcctatt ctccaccagg gacggccaaa cacacaagat cgcaaggcac     60
atcgcaggag tcctcgaaga gcaggggaag gcctgcgagt tggtcgatct gttacagccc    120
ggcgaaccag actggagtac cgttgaatgc gtcgttctag ggccagcat tagatatggt    180
cacttccata agtctttcat caggttcgta aacactcacg cgcagcgctt gaataatatg    240
ccaggcgccc ttttcacagt taacttagtc gcccgaaagc ccgagaagca gagtccacag    300
acgaactctt acacccgcaa gtttctcgcc gcctcccctt ggcagccaca gcgatgccaa    360
gttttcgcgg gcgctttgag gtaccctagg tactcgtggt acgacagaat gatgatacgt    420
ttgataatga agatggccgg gggcgagact gacacaagga aggaggttga gtacactgac    480
tggcagtcgg tgactcggtt cgcgagggag atcgctcagc tgccgggaga gacgcgg       537
```

<210> SEQ ID NO 68
<211> LENGTH: 534
<212> TYPE: DNA
<213> ORGANISM: Artificial Sequence
<220> FEATURE:
<223> OTHER INFORMATION: Recombinant

<400> SEQUENCE: 68

```
atgaaagcgc tgattctgtt tagcagccgc gatggccaga cccagctgat tgcgagcagc     60
attgcgaaag aactggaagg caaacaggcg tgcgatgtgc tgaacattct ggataccacc    120
aacgtggaat ggacccagta tgatcgcgtg ctgattggcg cgagcattcg ctatggccat    180
tttcatccgg cggtggcgga atttgtgaaa cgccatcagc gcgaactgca gcagcgcagc    240
agcggctttt ttagcgtgaa cctgaccgcg cgcaaaccgg aaaaacgcag cccggaaacc    300
aacgcgtata ccgcgaaatt tctgaaccag agcccgtggc agccggattg ctgcgcggtg    360
tttgcgggcg cgctgcgcta ccgcgctat cgctggtttg atcgcattat gattcagctg    420
attatgcgca tgaccggcgg cgaaaccgat agcagcaaag aagtggaata taccgattgg    480
```
cagcaggtga cccgctttgc gcaggaattt gcgcgcctgc cgggcaaaac cagc      534

<210> SEQ ID NO 69
<211> LENGTH: 540
<212> TYPE: DNA
<213> ORGANISM: Artificial Sequence
<220> FEATURE:
<223> OTHER INFORMATION: Recombinant

<400> SEQUENCE: 69
atgaaaaccc tgattctgtt tagcacccgc gatggccaga cccgcgaaat tgcggcgttt      60
ctggcgagcg aactgaaaga cagggcatt tatgcggatg tgattaacct gaaccgcacc      120
gaagaaattg cgtggcagga atatgatcgc gtggtgattg gcgcgagcat tcgctatggc      180
cattttcatc cggcggtgga tcgctttgtg aaaaaacata ccgaaaccct gaacagcctg      240
ccgggcgcgt tttttagcgt gaacctggtg gcgcgcaaag cggaaaaacg caccccgcag      300
accaacagct atacccgcaa atttctgctg aacagcccgt ggaaaccggc ggcgtgcgcg      360
gtgtttgcgg gcgcgctgcg ctatccgcgc tatcgctggt atgatcgctt tatgattcgc      420
ctgattatga aaatgaccgg cggcgaaacc gataccgca aagaagtggt gtataccgat      480
tggagccagg tggcgagctt tgcgcgcgaa attgtgcagc tgacccgcag cagccgcctg      540

<210> SEQ ID NO 70
<211> LENGTH: 531
<212> TYPE: DNA
<213> ORGANISM: Artificial Sequence
<220> FEATURE:
<223> OTHER INFORMATION: Recombinant

<400> SEQUENCE: 70
atgaaaattc tgattctgtt tagcacccgc gatggccaga cccgcgaaat tgcggcgagc      60
ctggcgagcg aactgaaaga cagggctttt gatgtggatg tggtgaacct gcatcgcgcg      120
gaaaacattg cgtgggaaga atatgatggc gtggtgattg gcgcgagcat tcgctatggc      180
cattttcata gcacccctgaa cagctttgtg aaaaaacatc agcaggcgct gaaaaaactg      240
ccgggcgcgt tttatagcgt gaacctggtg gcgcgcaaac cggaaaaacg caccccgcag      300
accaacagct atacccgcaa atttctgctg gatagcccgt ggcagccgga tctgagcgcg      360
gtgtttgcgg gcgcgctgcg ctatccgcgc tataactggt atgatcgcat tatgattcgc      420
ctgattatga aaattaccgg cggcgaaacc gataccgca aagaagtggt gtataccgat      480
tggcagcagg tgacccattt tgcgcatgaa attgtgcagc tggtgcgcaa a            531

<210> SEQ ID NO 71
<211> LENGTH: 540
<212> TYPE: DNA
<213> ORGANISM: Artificial Sequence
<220> FEATURE:
<223> OTHER INFORMATION: Recombinant

<400> SEQUENCE: 71
atgaaggcct tggtactgta ctcgacgcgg gacggccaga cccacgcaat tgcttcatac      60
atcgcctcct gcatgaagga gaaggccgaa tgcgacgtga tcgacctcac ccacggggag      120
cacgtgaacc tcacccaata cgatcaggtg ctaatcggtg cgagtattcg ttacggccac      180
ttcaacgccg tgcttgacaa gttcatcaag agaaacgtgg atcagctgaa caacatgcca      240
agcgcgttct tctgcgtaaa cctcacagca aggaagcccg agaagcgtac tccccagaca      300

```
aacccttatg tccgaaaatt cttgcttgct accccctggc agcccgcgtt gtgcggagtg    360
ttcgcagggg cccttcggta cccgcgatac cggtggatcg acaaggtgat gatccagcta    420
ataatgcgga tgactggggg agagacagac acgagcaagg aggtcgagta cacggattgg    480
gagcaggtta agaagttcgc ggaggatttt gcaaagctat cgtacaagaa ggccctctag    540
```

<210> SEQ ID NO 72
<211> LENGTH: 537
<212> TYPE: DNA
<213> ORGANISM: Artificial Sequence
<220> FEATURE:
<223> OTHER INFORMATION: Recombinant

<400> SEQUENCE: 72

```
atgaaggcct tgatcctgtt ctctacacgc gacggacaga cacagaagat cgcatctgcc     60
atcgctgatg agataaaggg gcagcaatcg tgcgacgtga ttaacataca ggatgccaaa    120
accctcgact ggcagcagta cgaccgggta ctcatcggcg cctccattcg ttacgggcat    180
ttccagcccg ttgtgaatga gtttgtcaag cacaacctct ggccctaca gcagagagtt    240 tccggattct ctccgtgaa cttgacagcc cgaaagccag agaagcggag ccccgagact    300
aacgcttata cagtcaaatt cttggcgcag tcaccctggc aaccggactg ctgcgctgtt    360
tttgcggggg ccctgtacta cccacggtac cggtggttcg ataggtgat gatacagttc    420 ataatgcgaa tgacgggggg agagaccgac gcatcgaaag aggtggagta cactgactgg    480
cagcaggtgc agcggttcgc gcgagacttc gcgcagttac cgggtaagtc ctactga      537
```

<210> SEQ ID NO 73
<211> LENGTH: 534
<212> TYPE: DNA
<213> ORGANISM: Artificial Sequence
<220> FEATURE:
<223> OTHER INFORMATION: Recombinant

<400> SEQUENCE: 73

```
atgaaggcgc tgatcttgta ctcaaccagg gacggtcaga ctcgcaagat tgcaagtagc     60
attgcggacg tcatcaggca gcagcagcag tgcgacgtct taaacattaa agacgcatca    120
cttcctgact gggcccaata tgaccgagtg ctcatcggag ctagcatccg ttacgggcat    180
ttccagcccg ttgtagacaa gttcgtgaag cagcacttgc acgagcttca gcagcggacc    240
tccggcttct ctccgtgaa cctgacggcg aggaagcctg aaaaaaggag ccctgagacc    300
aatgcctaca cccagaaatt cttggcgcac tccccttggc agcccgattg ctgtgccgtt    360
ttcgcggggg ccctttacta ccccaggtac cgttggttcg accgggtgat gatccagttg    420
attatgcgca tgactggtgg agagaccgac tctaccaagg aagtggagta cactgactgg    480
cagcaggtga gtaccttcgc caacgatttt gcccagcttc aggcaagag ctaa           534
```

<210> SEQ ID NO 74
<211> LENGTH: 546
<212> TYPE: DNA
<213> ORGANISM: Artificial Sequence
<220> FEATURE:
<223> OTHER INFORMATION: Recombinant

<400> SEQUENCE: 74

```
atgaagacct tgattctatt ctccacaagg gacggccaga ctagggagat cgcttcctac     60
ctggccagcg agctaaagga gcttggcatt caggcagacg tggctaacgt gcaccgaatt    120
gaggagccgc agtgggagaa ctacgatcgg gtcgtgatcg gcgccagcat ccggtatgga    180
```

```
cactaccaca gcgcgttcca ggagttcgtg aaaaagcacg cgacccgtct gaatagcatg    240
ccatcagcgt tctactcggt caacctcgtg gctcgtaagc ccgagaagcg gacacccag     300 accaactcgt atgccaggaa gttccttatg aactcgcagt ggcgaccgga ccgctgcgcg    360
gtgatcgccg gtgcgctcag gtaccctcgt tataggtggt acgacaggtt tatgattaaa    420
cttataatga aaatgagcgg cggagagacc gacaccagaa aagaggtggt ttacacagac    480
tgggagcagg tagcaaactt cgctagggag attgctcacc tcaccgacaa gccgaccttg    540
aagtaa                                                               546

<210> SEQ ID NO 75
<211> LENGTH: 537
<212> TYPE: DNA
<213> ORGANISM: Artificial Sequence
<220> FEATURE:
<223> OTHER INFORMATION: Recombinant

<400> SEQUENCE: 75
atgaaggccc ttatactgtt cagttccaga gaaggccaga cgagggagat agcgagttac    60
attgccaact cgataaagga ggaaatggaa tgcgacgtgt tcaacatcct tcgtgtggag    120
cagatcgact ggtctcaata cgaccgcgtc ctgatcgggg gctcgataca ctacggccat    180
ttccacccag cggtggcaaa atttgtcaag aggcacctcc atgagttgca acagaggtct    240
tccggctttt tctgcgtcaa cctgacggcc aggaaggccg acaagcggac tccccagacc    300
aatgcctaca tgagaaagtt cttgttgcag tccccatggc aacccgattg ctgcgccgtg    360
tttgcggggg cccttaggta cacccgttac aggtggttcg acgggtaat gattcagctg     420 atcatgagga tgacgggcgg agagactgac acatcgaagg aggtggagta cacagactgg    480
acgcaggtcg cccgcttcgc gcaggagttc gcccatttgc ccggcaaaac tcagtga       537

<210> SEQ ID NO 76
<211> LENGTH: 540
<212> TYPE: DNA
<213> ORGANISM: Artificial Sequence
<220> FEATURE:
<223> OTHER INFORMATION: Recombinant

<400> SEQUENCE: 76
atgaaggctc ttatcgtatt ctcttcgagg gatggccaaa cccgagcgat cgcgtcttat    60
attgctaata ccctcaaagg gaccctagag tgcgacgtcg tcaacgtcct caatgctaac    120
gacattgatt tgagccagta cgaccgtgtg gccattggcg cctccattcg ctacggggag    180
ttccacccag ctgttaacca gtttatccgg aagcaccttta cgagcctcca gcagctacca    240
tctgcgttct ctccgtgaa cctcacagct cggaagcccg agaagaggac tatacaaacc    300
aacgcgtaca ctaggaagtt tctactgaac tcgccgtggc agccggacct gtgctgcgtg    360
ttcgcgggag cccttcgcta tccccgttac aggtggtttg accgagtgat gattcaactc    420
ataatgcgca taacgggggg cgagacagac tccaccaagg agatcgagta caccgactgg    480
cagcaggtcg cgcgattcgc ccaggatttt gcacagcttg ccgcaaagaa cccggcatga   540

<210> SEQ ID NO 77
<211> LENGTH: 540
<212> TYPE: DNA
<213> ORGANISM: Artificial Sequence
<220> FEATURE:
<223> OTHER INFORMATION: Recombinant
```

<400> SEQUENCE: 77

```
atgaagacct tgatcctatt ctccaccagg gacggccaaa cacacaagat cgcaaggcac    60
atcgcaggag tcctcgaaga gcaggggaag gcctgcgagt tggtcgatct gttacagccc   120
ggcgaaccag actggagtac cgttgaatgc gtcgttctag ggccagcat tagatatggt   180
cacttccata agtctttcat caggttcgta aacactcacg cgcagcgctt gaataatatg   240
ccaggcgccc ttttcacagt taacttagtc gcccgaaagc ccgagaagca gagtccacag   300
acgaactctt acacccgcaa gtttctcgcc gcctcccctt ggcagccaca gcgatgccaa   360
gttttcgcgg gcgctttgag gtaccctagg tactcgtggt acgacagaat gatgatacgt   420
ttgataatga agatggccgg gggcgagact gacacaagga aggaggttga gtacactgac   480
tggcagtcgg tgactcggtt cgcgagggag atcgctcagc tgccgggaga gacgcggtag   540
```

<210> SEQ ID NO 78
<211> LENGTH: 537
<212> TYPE: DNA
<213> ORGANISM: Artificial Sequence
<220> FEATURE:
<223> OTHER INFORMATION: Recombinant

<400> SEQUENCE: 78

```
atgaaggccc taattttatt cagtagtagg gacggccaga cccagcttat agcatcgtct    60
atcgccaagg agctcgaagg gaagcaggcg tgcgacgtgt tgaatatcct cgacacgact   120
aatgtggagt ggacccagta cgaccgcgtg ctgattggag catccatccg gtacgggcac   180
tttcaccctg cggtcgccga gttcgtaaag cgtcaccagc gagagctaca gcagagaagt   240
agtggctttt tctctgtgaa cttgacggcc cgtaagccgg aaaagaggtc ccccgagact   300
aacgcctata ccgccaagtt ccttaaccaa agtccatggc agcctgactg ttgcgctgtg   360
ttcgctgggg ctttgcgata ccctcggtac cgctggttcg acagaattat gatccagcta   420
atcatgcgga tgactggggg tgagacagat tcttcaaagg aggtcgagta caccgactgg   480
cagcaggtga cccgcttcgc gcaagagttc gccaggcttc cgggaaagac cagttga       537
```

<210> SEQ ID NO 79
<211> LENGTH: 543
<212> TYPE: DNA
<213> ORGANISM: Artificial Sequence
<220> FEATURE:
<223> OTHER INFORMATION: Recombinant

<400> SEQUENCE: 79

```
atgaagaccc taatactgtt ctctacccgc gacgggcaga caagggagat cgccgcgttc    60
cttgcctcgg agctgaagga gcaggggatt tacgctgacg tcataaacct taaccggacg   120
gaggagatag cttggcagga gtatgataga gtcgtaatcg gggcgtcgat ccgatacggg   180
catttccacc ctgctgtcga ccgcttcgtg aagaagcaca cagagacact caactcactg   240
cccggcgcct ttttctctgt aaaccttgtt gcccggaaag ccgagaagag aacgccgcag   300
acgaactcat acaccaggaa gttcctatta aacagcccgt ggaagccagc ggcctgcgcg   360
gtctttgctg ggccctccg ctaccctaga taccgctggt acgacaggtt catgatacga   420
ctgattatga aaatgacagg cggggagacg gataccgaaa aggaggtagt ctacactgac   480
tggtcgcagg tcgcgtcgtt tgccagagag atagtccagt tgaccaggtc atcgcgcttg   540
tga                                                                 543
```

```
<210> SEQ ID NO 80
<211> LENGTH: 534
<212> TYPE: DNA
<213> ORGANISM: Artificial Sequence
<220> FEATURE:
<223> OTHER INFORMATION: Recombinant

<400> SEQUENCE: 80
atgaagatat taatccttt ctccacccgt gacggccaaa cccgtgagat tgcggcgtcc      60
ttggcgtccg aactcaagga gcaggcattc gacgtggacg tcgtcaacct tcaccgggcc    120
gagaacatcg catgggagga gtacgacggt gttgtcatcg gagcgtccat caggtacggc    180
cactttcata gtaccctgaa ctcatttgtc aagaagcatc agcaggctct taagaagctt    240
cccgggcttt tctacagcgt gaacctcgtc gcccggaagc tgagaagcg cacaccgcag     300
accaatagct acaccgcaa gttcctcttg gattccccgt ggcagcccga cctttcagcc     360
gtgttcgccg gggcactcag gtaccctcgg tacaattggt acgaccgtat catgattaga    420
cttatcatga agattacagg cggcgagact gataccagga aggaagtagt ctacacagac    480
tggcagcagg tcactcactt tgctcacgag atcgtccagc tcgtgcggaa gtag           534

<210> SEQ ID NO 81
<211> LENGTH: 537
<212> TYPE: DNA
<213> ORGANISM: Artificial Sequence
<220> FEATURE:
<223> OTHER INFORMATION: Recombinant

<400> SEQUENCE: 81
aaggccttgg tactgtactc gacgcgggac ggccagaccc acgcaattgc ttcatacatc     60
gcctcctgca tgaaggagaa ggccgaatgc gacgtgatcg acctcaccca cggggagcac    120
gtgaacctca cccaatacga tcaggtgcta atcggtgcga gtattcgtta cggccacttc    180
aacgccgtgc ttgacaagtt catcaagaga acgtggatc agctgaacaa catgccaagc     240
gcgttcttct gcgtaaacct cacagcaagg aagcccgaga gcgtactcc ccagacaaac      300
ccttatgtcc gaaaattctt gcttgctacc cctggcagc ccgcgttgtg cggagtgttc       360
gcaggggccc ttcggtaccc gcgataccgg tggatcgaca aggtgatgat ccagctaata    420
atgcggatga ctgggggaga gacagacacg agcaaggagg tcgagtacac ggattgggag    480
caggttaaga agttcgcgga ggattttgca agctatcgt acaagaaggc cctctag          537

<210> SEQ ID NO 82
<211> LENGTH: 534
<212> TYPE: DNA
<213> ORGANISM: Artificial Sequence
<220> FEATURE:
<223> OTHER INFORMATION: Recombinant

<400> SEQUENCE: 82
aaggccttga tcctgttctc tacacgcgac ggacagacac agaagatcgc atctgccatc     60
gctgatgaga taaaggggca gcaatcgtgc gacgtgatta acatacagga tgccaaaacc    120
ctcgactggc agcagtacga ccgggtacta atcggcgcct ccattcgtta cggcatttc     180
cagcccgttg tgaatgagtt tgtcaagcac aacctcttgg ccctacagca gagagtttcc    240
ggattcttct ccgtgaactt gacagcccga aagccagaga agcggagccc cgagactaac    300
gcttatacag tcaaattctt ggcgcagtca ccctggcaac cggactgctg cgctgttttt    360
gcgggggccc tgtactaccc acggtaccgg tggttcgata gggtgatgat acagttcata    420
```

```
atgcgaatga cgggggggaga gaccgacgca tcgaaagagg tggagtacac tgactggcag    480
caggtgcagc ggttcgcgcg agacttcgcg cagttaccgg gtaagtccta ctga           534
```

<210> SEQ ID NO 83
<211> LENGTH: 543
<212> TYPE: DNA
<213> ORGANISM: Artificial Sequence
<220> FEATURE:
<223> OTHER INFORMATION: Recombinant

<400> SEQUENCE: 83

```
aagaccttga ttctattctc cacaagggac ggccagacta gggagatcgc ttcctacctg     60
gccagcgagc taaaggagct tggcattcag gcagacgtgg ctaacgtgca ccgaattgag    120
gagccgcagt gggagaacta cgatcgggtc gtgatcggcg ccagcatccg gtatggacac    180
taccacagcg cgttccagga gttcgtgaaa aagcacgcga cccgtctgaa tagcatgcca    240
tcagcgttct actcggtcaa cctcgtggct cgtaagcccg agaagcggac accccagacc    300
aactcgtatg ccaggaagtt ccttatgaac tcgcagtggc gaccggaccg ctgcgcggtg    360
atcgccggtg cgctcaggta ccctcgttat aggtggtacg acaggtttat gattaaactt    420
ataatgaaaa tgagcggcgg agagaccgac accagaaaag aggtggttta cacagactgg    480
gagcaggtag caaacttcgc tagggagatt gctcacctca ccgacaagcc gaccttgaag    540
taa                                                                  543
```

<210> SEQ ID NO 84
<211> LENGTH: 534
<212> TYPE: DNA
<213> ORGANISM: Artificial Sequence
<220> FEATURE:
<223> OTHER INFORMATION: Recombinant

<400> SEQUENCE: 84

```
aaggccctta tactgttcag ttccagagaa ggccagacga gggagatagc gagttacatt     60
gccaactcga taaaggagga atggaatgc gacgtgttca acatccttcg tgtggagcag     120
atcgactggt ctcaatacga ccgcgtcctg atcgggggct cgatacacta cggccatttc    180
cacccagcgg tggcaaaatt tgtcaagagg cacctccatg agttgcaaca gaggtcttcc    240 ggcttttttct gcgtcaacct gacggccagg aaggccgaca gcggactcc ccagaccaat    300 gcctacatga gaaagttctt gttgcagtcc ccatggcaac ccgattgctg cgccgtgttt    360 gcggggggccc ttaggtacac ccgttacagg tggttcgaca gggtaatgat tcagctgatc    420
atgaggatga cgggcggaga gactgacaca tcgaaggagg tggagtacac agactggacg    480
caggtcgccc gcttcgcgca ggagttcgcc catttgcccg gcaaaactca gtga           534
```

<210> SEQ ID NO 85
<211> LENGTH: 537
<212> TYPE: DNA
<213> ORGANISM: Artificial Sequence
<220> FEATURE:
<223> OTHER INFORMATION: Recombinant

<400> SEQUENCE: 85

```
aaggctctta tcgtattctc ttcgagggat ggccaaaccc gagcgatcgc gtcttatatt     60 gctaatccc tcaaagggac cctagagtgc gacgtcgtca acgtcctcaa tgctaacgac     120
attgatttga gccagtacga ccgtgtgcc attggcgcct ccattcgcta cgggaggttc    180
cacccagctg ttaaccagtt tatccggaag caccttacga gcctccagca gctaccatct    240
```

```
gcgttcttct ccgtgaacct cacagctcgg aagcccgaga agaggactat acaaaccaac    300
gcgtacacta ggaagtttct actgaactcg ccgtggcagc cggacctgtg ctgcgtgttc    360
gcgggagccc ttcgctatcc ccgttacagg tggtttgacc gagtgatgat tcaactcata    420
atgcgcataa cgggggggcga gacagactcc accaaggaga tcgagtacac cgactggcag    480
caggtcgcgc gattcgccca ggattttgca cagcttgccg caaagaaccc ggcatga       537
```

<210> SEQ ID NO 86
<211> LENGTH: 537
<212> TYPE: DNA
<213> ORGANISM: Artificial Sequence
<220> FEATURE:
<223> OTHER INFORMATION: Recombinant

<400> SEQUENCE: 86

```
aagaccttga tcctattctc caccagggac ggccaaacac acaagatcgc aaggcacatc    60
gcaggagtcc tcgaagagca ggggaaggcc tgcgagttgg tcgatctgtt acagcccggc    120
gaaccagact ggagtaccgt tgaatgcgtc gttctagggg ccagcattag atatggtcac    180
ttccataagt cttccatcag gttcgtaaac actcacgcgc agcgcttgaa taatatgcca    240
ggcgcccttt tcacagttaa cttagtcgcc cgaaagcccg agaagcagag tccacagacg    300
aactcttaca cccgcaagtt tctcgccgcc tcccccttggc agccacagcg atgccaagtt    360
ttcgcgggcg ctttgaggta ccctaggtac tcgtggtacg acagaatgat gatacgtttg    420
ataatgaaga tggccggggg cgagactgac acaaggaagg aggttgagta cactgactgg    480
cagtcggtga ctcggttcgc gagggagatc gctcagctgc cgggagagac gcggtag      537
```

<210> SEQ ID NO 87
<211> LENGTH: 540
<212> TYPE: DNA
<213> ORGANISM: Artificial Sequence
<220> FEATURE:
<223> OTHER INFORMATION: Recombinant

<400> SEQUENCE: 87

```
aagaccctaa tactgttctc tacccgcgac gggcagacaa gggagatcgc cgcgttcctt    60
gcctcggagc tgaaggagca ggggatttac gctgacgtca taaaccttaa ccggacggag    120
gagatagctt ggcaggagta tgatagagtc gtaatcgggg cgtcgatccg atacgggcat    180
ttccaccctg ctgtcgaccg cttcgtgaag aagcacacag agacactcaa ctcactgccc    240
ggcgcctttt tctctgtaaa ccttgttgcc cggaaagccg agaagagaac gccgcagacg    300
aactcataca ccaggaagtt cctattaaac agcccgtgga agccagcggc ctgcgcggtc    360
tttgctgggg ccctccgcta ccctagatac cgctggtacg acaggttcat gatacgactg    420
attatgaaaa tgacaggcgg ggagacggat acccgaaagg aggtagtcta cactgactgg    480
tcgcaggtcg cgtcgtttgc cagagagata gtccagttga ccaggtcatc gcgcttgtga    540
```

<210> SEQ ID NO 88
<211> LENGTH: 537
<212> TYPE: DNA
<213> ORGANISM: Artificial Sequence
<220> FEATURE:
<223> OTHER INFORMATION: Recombinant

<400> SEQUENCE: 88

```
aaggccttgg tactgtactc gacgcgggac ggccagaccc acgcaattgc ttcatacatc    60
```

```
gcctcctgca tgaaggagaa ggccgaatgc gacgtgatcg acctcaccca cggggagcac    120
gtgaacctca cccaatacga tcaggtgcta atcggtgcga gtattcgtta cggccacttc    180
aacgccgtgc ttgacaagtt catcaagaga aacgtggatc agctgaacaa catgccaagc    240
gcgttcttct gcgtaaacct cacggcaagg aagcccgaga agcgtactcc ccagacaaac    300
ccttatgtcc gaaaattctt gcttgctacc ccctggcagc ccgcgttgtg cggagtgttc    360 gcagggccc  ttcggtaccc gcgataccgg tggatcgaca aggtgatgat ccagctaata    420
atgcggatga ctgggggaga gacagacacg agcaaggagg tcgagtacac ggattgggag    480
caggttaaga agttcgcgga ggattttgca aagctatcgt acaagaaggc cctctag      537
```

<210> SEQ ID NO 89
<211> LENGTH: 537
<212> TYPE: DNA
<213> ORGANISM: Artificial Sequence
<220> FEATURE:
<223> OTHER INFORMATION: Recombinant

<400> SEQUENCE: 89

```
aaggccttgg tactgtactc gacgcgggac ggccagaccc acgcaattgc ttcatacatc     60
gcctcctgca tgaaggagaa ggccgaatgc gacgtgatcg acctcaccca cggggagcac    120
gtgaacctca cccaatacga tcaggtgcta atcggtgcga atattcgtta cggccacttc    180
aacgccgtgc ttgacaagtt catcaagaga aacgtggatc agctgaacaa catgccaagc    240
gcgttcttct gcgtaaacct cacagcaagg aagcccgaga agcgtactcc ccagacaaac    300
ccttatgtcc gaaaattctt gcttgctacc ccctggcagc ccgcgttgtg cggagtgttc    360 gcagggccc  ttcggtaccc gcgataccgg tggatcgaca aggtgatgat ccagctaata    420
atgcggatga ctgggggaga gacagacacg agcaaggagg tcgagtacac ggattgggag    480
caggttaaga agttcgcgga ggattttgca aagctatcgt acaagaaggc cctctag      537
```

<210> SEQ ID NO 90
<211> LENGTH: 537
<212> TYPE: DNA
<213> ORGANISM: Artificial Sequence
<220> FEATURE:
<223> OTHER INFORMATION: Recombinant

<400> SEQUENCE: 90

```
aaggccttgg tactgtactc gacgcgggac ggccagaccc acgcaattgc ttcatacatc     60
gcctcctgca tgaaggagaa ggccgaatgc gacgtgatcg acctcaccca cggggagcac    120
gtgaacctca cccaatacga tcaggtgcta atcggtgcga gtattcgtta cggccacttc    180
aacgccgtgc ttgacaagtt catcaagaga aacgtggatc agctgaacaa catgccaagc    240
gcgttcttct gcgtaaacct cacagcaagg aagcccgaga agcgtactcc ccagacaaac    300
ccttatgtcc gaaaattctt gcttgctacc ccctggcagc ccgcgttgtg cggagtgttc    360 gcagggccc  ttcggtaccc gcgataccgg tggatcgaca aggtgatgat ccagctaata    420
atgcggatga ctgggggaga gacagacacg agcaaggagg tcgagtacac ggattgggag    480
caggttaaga agttcgcgga ggattttgca aagctatagt acaagaaggc cctctag      537
```

<210> SEQ ID NO 91
<211> LENGTH: 534
<212> TYPE: DNA
<213> ORGANISM: Artificial Sequence
<220> FEATURE:
<223> OTHER INFORMATION: Recombinant

<400> SEQUENCE: 91

```
aaggccttga tcctgttctc tacacgcgac ggacagacac agaagatcgc atctgccatc    60
gctgatgaga taaaggggca gcaatcgtgc gacgtgatta acatacagga tgccaaaacc   120
ctcgactggc agcagtacga ccgggtactc atcggcgcct ccattcgtta cgggcatttc   180
cagcccgttg tgaatgagtt tgtcaagcac aacctcttgg ccctacagca gagagtttcc   240
ggattcttct ccgtgaactt gacagcccga agccagaga agcggagccc cgagactaac   300
gcttatacag tcaaattctt ggcgcagtca ccctggcaac cggactgctg cgctgttttt   360
gcgggggccc tgtactaccc acggtaccgg tggttcgata gggtgatgat acagttcata   420
atgcgaatga cgggggggga gaccgacgca tcgaaagagg tggagtacac tgactggcag   480
caggtgcagc ggttcgcgcg agacttcgcg cagttaccgg gtaagtccta ctga          534
```

<210> SEQ ID NO 92
<211> LENGTH: 540
<212> TYPE: DNA
<213> ORGANISM: Artificial Sequence
<220> FEATURE:
<223> OTHER INFORMATION: Recombinant

<400> SEQUENCE: 92

```
aagaccctaa tactgttctc tacccgcgac gggcagacaa gggagatcgc cgcgttcctt    60
gcctcggagc tgaaggagca ggggatttac gctgacgtca taaaccttaa ccggacggag   120
gagatagctt ggcaggagta tgatagagtc gtaatcgggg cgtcgatccg atacgggcat   180
ttccacccctg ctgtcgaccg cttcgtgaag aagcacacag agacactcaa ctcactgccc   240
ggcgcctttt tctctgtaaa ccttgttgcc cggaaagccg agaagagaac gccgcagacg   300
aactcataca ccaggaagtt cctattaaac agcccgtgga agccagcggc ctgcgcggtc   360
tttgctgggg ccctccgcta ccctagatac cgctggtacg acaggttcat gatacgactg   420
attatgaaaa tgacaggcgg ggagacggat acccgaaagg aggtagtcta cactgactgg   480
tcgcagatcg cgtcgtttgc cagagagata gtccagttga ccaggtcatc gcgcttgtga   540
```

<210> SEQ ID NO 93
<211> LENGTH: 540
<212> TYPE: DNA
<213> ORGANISM: Artificial Sequence
<220> FEATURE:
<223> OTHER INFORMATION: Recombinant

<400> SEQUENCE: 93

```
atgaaggcgc tcgtgctcta cagcacacgc gacggccaga ctcatgcgat cgcctcttac    60
atcgcgtcct gtatgaagga gaaggccgag tgcgacgtca tcgatctcac gcacggggag   120
cacgtgaatc ttacgcagta cgaccaagtg ctgataggcg cctctatccg ttacggccat   180
tttaacgccg tcctcgacaa attcatcaag cgcaatgtag accagctgaa caacatgccc   240
tccgcgttct tttgcgtgaa cctgacggct cggaagcctg agaagcgaac acctcagacc   300
aacccatacg tgcggaaatt cctactcgca acgccatggc agcccgccct gtgcggggtt   360
ttcgcagggg cgctacgcta tccgcgttac cgctggatcg ataaggtgat gatccagcta   420
ataatgcgca tgaccggcgg cgagacagac acatcgaagg aagtcgaata cacagactgg   480
gaacaggtga agaagtttgc agaggatttc gccaagctct catacaaaaa ggcattgtga   540
```

<210> SEQ ID NO 94

```
<211> LENGTH: 537
<212> TYPE: DNA
<213> ORGANISM: Artificial Sequence
<220> FEATURE:
<223> OTHER INFORMATION: Recombinant

<400> SEQUENCE: 94
atgaaggcgc ttatactgtt ctcgacacgc gacggtcaga cgcagaaaat cgcctcagcc     60
atcgccgacg agatcaaggg ccagcagagc tgcgatgtga tcaatattca ggacgccaaa    120
actctcgact ggcagcagta tgaccgcgtg ctcattggcg catcaatccg ctacgggcat    180
ttccagccag tcgtcaatga gtttgtgaaa cataacctct ggcattgca gcagcgggtg     240
tctggcttct tctccgtgaa ccttacagct agaaaaccag agaagcggtc gcccgagact    300
aacgcctaca ccgttaagtt ccttgcgcag tcaccgtggc agcctgattg ctgcgcggtc    360
ttcgccgggg cactgtacta ccctcgatac cggtggtttg atagggtaat gatccagttc    420
ataatgcgca tgaccggtgg ggagaccgac gcaagtaaag aagttgagta cacggattgg    480
cagcaggtgc aaaggttcgc acgcgacttc gcgcagctcc cgggcaagtc ttactga      537

<210> SEQ ID NO 95
<211> LENGTH: 534
<212> TYPE: DNA
<213> ORGANISM: Artificial Sequence
<220> FEATURE:
<223> OTHER INFORMATION: Recombinant

<400> SEQUENCE: 95
atgaaagccc tgatcctcta ttccaccagg gacggccaga cccgcaagat agcctcctcc     60
atcgctgatg tcatccgcca gcagcagcag tgcgacgttt aaacattaa ggacgcttca    120
ctgcctgatt gggcccagta tgaccgcgtc ctgatcggcg cgtcgattcg gtacggccac    180
ttccagcctg tggttgacaa gttcgtcaag cagcacctgc atgagctgca gcagcgaact    240
agcgggttct tcagtgtgaa cctgacagct agaaagcccg aaaagagatc cccagaaacc    300
aacgcctata cgcagaaatt ccttgctcac tcaccctggc agcctgactg ttgtgccgtc    360
ttcgcgggcg ccttgtacta tccccgctac cgctggttcg atagggtgat gatccagctg    420
attatgagaa tgacgggagg ggagaccgat tcgaccaagg aggtagagta cactgactgg    480
caacaggtgt caactttcgc aaacgacttc gcacaactac ccggtaagtc ttga         534

<210> SEQ ID NO 96
<211> LENGTH: 546
<212> TYPE: DNA
<213> ORGANISM: Artificial Sequence
<220> FEATURE:
<223> OTHER INFORMATION: Recombinant

<400> SEQUENCE: 96
atgaaaaccc taatactgtt ctcgacccgc gacggccaga cgcgtgagat tgcgagctac     60
ctggcctccg agctcaagga gctggggatc caagccgatg tcgcgaacgt gcaccgcatt    120
gaggagccgc agtgggagaa ttacgatcgc gttgtgatag gggccagcat ccgctatggc    180
cactaccact cggcctttca ggagtttgta aagaaacacg ccacaagatt aaactccatg    240
cctagcgcct tctactccgt caaccttgtc gcgcgcaagc cggagaagcg gacacctcag    300
acgaactcct acgcgcggaa gttcctgatg aacagccagt ggcggccgga cagatgtgct    360
gttattgcgg gagccctgag ataccggagg taccggtggt acgataggtt tatgattaaa    420
cttattatga agatgtctgg tggggagact gacaccagga aggaggtggt atatacagac    480
```

```
tgggagcagg tcgccaattt cgctcgggaa atcgcgcatc tgacagacaa gcctacactg    540
aagtag                                                              546

<210> SEQ ID NO 97
<211> LENGTH: 537
<212> TYPE: DNA
<213> ORGANISM: Artificial Sequence
<220> FEATURE:
<223> OTHER INFORMATION: Recombinant

<400> SEQUENCE: 97
atgaaggccc tgatcctctt tagctctagg gagggccaga cccgcgagat cgcgtcatat     60
atcgcgaatt ccataaagga ggagatggag tgcgatgtgt ttaacatcct tagggtggag    120
caaatagact ggtctcagta tgaccgtgtg ctcataggg ggagcatcca ctacggccac     180
tttcacccgg ccgtggcgaa attcgtcaag cgacacctcc acgagcttca gcagcgctcc    240
tcagggttct tctgcgtcaa cctgacagca agaaaggcag ataaacgcac cccgcagacg    300
aacgcctaca tgaggaagtt ccttctgcag tctccttggc agcccgattg ctgcgcggtg    360
ttcgccggtg cactgcgcta tacgcgctat agatggtttg atagagtcat gattcagctc    420
atcatgcgga tgaccggcgg ggaaacggat actagtaagg aggtggagta cacggactgg    480
acccaggtgg cacgtttcgc ccaggagttt gcacatcttc ctgggaagac ccaatga      537

<210> SEQ ID NO 98
<211> LENGTH: 540
<212> TYPE: DNA
<213> ORGANISM: Artificial Sequence
<220> FEATURE:
<223> OTHER INFORMATION: Recombinant

<400> SEQUENCE: 98
atgaaggcgc taattgtgtt cagctccagg gatggccaga cgagggctat agcatcctat     60
atcgccaata ccttgaaagg aacgctcgag tgtgacgtgg tcaacgtctt gaacgccaat    120
gacattgacc tttcccagta cgaccgagtt gccataggcg cgtcgatccg ctacgggcga    180
tttcaccctg cagtcaacca gtttatacgg aagcatttga cctcgctgca gcagctcccg    240
tcagccttct tctctgtgaa tttaaccgcg cggaagcctg agaaacggac gatccaaaca    300
aacgcctata cccgaaagtt cctcctgaac agcccatggc agccagacct gtgctgtgtc    360
ttcgccggcg cgttgcggta tccccgctac aggtggttcg atagagtgat gatccagctc    420
atcatgagga tcaccggggg agagaccgat agtaccaagg agatcgagta cacggactgg    480
cagcaggtgg ctcgcttcgc ccaggacttc gctcagttgg ccgcaaagaa tccagcataa    540

<210> SEQ ID NO 99
<211> LENGTH: 540
<212> TYPE: DNA
<213> ORGANISM: Artificial Sequence
<220> FEATURE:
<223> OTHER INFORMATION: Recombinant

<400> SEQUENCE: 99
atgaagacac tgatcctgtt ctcgactcga gatggccaga ctcataaaat tgcgcgccac     60
attgcggggg tcctggagga gcagggcaaa gcgtgcgagc tcgtggactt actccagccc    120
ggggagccgg actggagcac ggtggagtgc gtcgttctgg gcgcttccat acgttacggg    180
catttccaca aaagtttcat ccggttcgtc aacacccacg ctcaacggct gaacaacatg    240
```

```
cctggcgcgc tattcactgt taacttagtg gctcgtaagc ccgagaagca gtctccgcag      300
actaactcct acacaaggaa atttctagca gcaagcccat ggcaaccgca gcggtgccag      360
gtgttcgctg gagctctgcg ctatcctagg tacagttggt acgacagaat gatgatacgg      420
ttgattatga agatggcagg cggggagacg gacaccagga aagaggtcga atacactgac      480
tggcaatcag tcactcggtt tgctagagag atcgcgcaat taccaggtga gacgcggtaa      540
```

<210> SEQ ID NO 100
<211> LENGTH: 537
<212> TYPE: DNA
<213> ORGANISM: Artificial Sequence
<220> FEATURE:
<223> OTHER INFORMATION: Recombinant

<400> SEQUENCE: 100

```
atgaaggctc tcatactgtt cagctcgaga gacgggcaga cccagctgat cgcctcctcc       60
atagcaaagg agctagaggg caagcaagcc tgcgacgtgc tcaatattct cgacacaacc      120
aacgtggagt ggactcagta cgacagagtc ctaatcggcg cgtccatcag atacggccac      180
ttccatcccg ccgtcgctga attcgtgaaa cgccaccagc gtgagctcca gcagcgcagc      240
agcggcttct tcagcgtgaa tcttactgcg agaaagccgg aaaagcggag tcccgagact      300
aacgcttata cggcaaagtt cctcaaccaa tctccctggc aaccagactg ctgtgccgtg      360
ttcgctgggg cactgaggta tccgcgctat cggtggttcg atagaatcat gatacagctg      420
ataatgcgta tgactggtgg ggagacggat tccagtaaag aggtagagta tactgattgg      480
cagcaggtca ctaggttcgc gcaggagttt gctaggctgc cgggcaagac atcctga       537
```

<210> SEQ ID NO 101
<211> LENGTH: 543
<212> TYPE: DNA
<213> ORGANISM: Artificial Sequence
<220> FEATURE:
<223> OTHER INFORMATION: Recombinant

<400> SEQUENCE: 101

```
atgaaaacct taatcttgtt cagcacccgc gacggccaga cgcgtgaaat cgcagcgttc       60
ctcgcttcgg agctcaagga acagggaatt tacgccgacg tcattaacct aaaccgtacc      120
gaagagattg cgtggcagga gtatgaccgc gtggtgattg gcgcttctat ccgctatggc      180
cacttccacc cggctgttga ccggttcgtg aagaagcaca cggagacctt gaactcactg      240 ccggggggcat tctttagcgt aaatctggtg gcgcgcaagg ccgagaagcg cacccccccag      300 acgaacagct acacccgcaa atttttactt aactccccat ggaaacctgc ggcctgcgca      360
gtgttcgcag gagctctccg ctatcctcgc tatcgatggt acgatcggtt catgattcgg      420
ctgattatga aaatgacggg cggcgagacg gatacgcgaa aggaagttgt ctacactgac      480
tggtcccagg tggcctcgtt tgcaagggag atcgtacagc tcactcgatc tagtaggctc      540
tga                                                                   543
```

<210> SEQ ID NO 102
<211> LENGTH: 534
<212> TYPE: DNA
<213> ORGANISM: Artificial Sequence
<220> FEATURE:
<223> OTHER INFORMATION: Recombinant

<400> SEQUENCE: 102

```
atgaagattc tcatcttatt ttccaccccga gacggccaaa cccgcgagat tgcggcgtcc       60
```

-continued

```
ctcgcctccg agttgaagga gcaggcgttt gatgtggatg tggtcaacct ccaccgcgca      120
gaaaacatag cgtgggagga gtacgatggg gtcgtcatcg gagcgtcaat ccgctacgga      180
catttccact caacgctgaa ttcatttgtg aagaagcacc aacaagcgct caagaagctg      240
cccggagcat tctacagcgt caacctcgtg gctcggaagc cggaaaagcg caccccgcaa      300
acaaacagct acacacgcaa gtttctgctc gactcgccct ggcaacccga cctgagtgcc      360
gttttcgccg gggcactgcg ctatccccgt tacaactggt acgatcgcat aatgattcga      420
ctgatcatga agattacagg cggggaaacc gatactcgga aggaggtggt gtatacagac      480
tggcagcagg ttacccactt cgcccacgag atcgtccagc tcgttcgtaa gtga           534
```

US 10,563,220 B2

COMPOSITIONS AND METHODS FOR EFFICIENT TARGETING OF TRANSGENES

CROSS REFERENCE TO RELATED APPLICATIONS

This application claims the benefit of U.S. Provisional Application No. 62/270,180, filed on Dec. 21, 2015, and U.S. Provisional Application No. 62/364,715, filed on Jul. 20, 2016, herein incorporated by reference in its entirety.

FIELD OF THE INVENTION

The invention relates generally to the fields of agriculture, plant biotechnology, and molecular biology. More specifically, the invention relates to compositions and methods for producing transgenic plants exhibiting herbicide tolerance or resistance.

INCORPORATION OF SEQUENCE LISTING

A computer readable form of a sequence listing is filed with this application by electronic submission and is incorporated into this application by reference in its entirety. The sequence listing is contained in the file named MONS389US_sequence_listing.txt, which is 125,128 kilobytes in size (measured in operating system MS Windows) and created on Nov. 22, 2016.

DESCRIPTION OF RELATED ART

The production of novel transgenic plants offers the potential for significantly improved crop plants exhibiting beneficial traits, such as improved herbicide tolerance to allow for enhanced weed control strategies. However, while proteins useful for producing beneficial traits in crops are known, effective sub-cellular localization (known as targeting) and processing of these recombinant proteins in transgenic plant cells remains a significant obstacle. A need therefore exists for novel transit peptides capable of effectively localizing recombinant proteins within plant cells.

SUMMARY

One aspect of the invention relates to a recombinant DNA molecule comprising a DNA sequence encoding a chloroplast transit peptide (CTP) operably linked to a DNA sequence encoding a dicamba monooxygenase (DMO) or a protoporphyrinogen oxidase (PPO), wherein the CTP comprises a sequence selected from the group consisting of SEQ ID NOs:1-3. In certain embodiments, the DNA sequence encoding a CTP comprises a sequence selected from the group consisting of SEQ ID NOs:7-14. In further embodiments, the DMO or PPO comprises a polypeptide selected from the group consisting of SEQ ID NOs:18-27 and 40-59. In one embodiment, the DNA sequence a DMO or PPO comprises a sequence selected from the group consisting of SEQ ID NOs:28-37 and 61-102. In specific embodiments, the DMO or PPO is defined as a herbicide tolerance protein that is capable of conferring herbicide tolerance when expressed in a plant cell. In particular embodiments, the herbicide tolerance protein is a DMO protein, and the CTP comprises a sequence selected from the group consisting of SEQ ID NOs:1-3, or the herbicide tolerance protein is a PPO protein, and the CTP comprises a sequence selected from the group consisting of SEQ ID NOs:1 and 2.

In another aspect, the invention provides a DNA construct comprising the a recombinant DNA molecule as described herein operably linked to a heterologous promoter functional in a plant cell.

In yet another aspect, the invention provides a transgenic plant, plant cell, plant part, or seed transformed with a recombinant DNA molecule of the invention. In specific embodiments, the plant is a monocot plant. Monocot plants that may be used with the invention include, but are not limited to, maize or wheat plants. In another embodiment, the plant is a dicot plant. Dicot plants that may be used with the invention include, but are not limited to, a soybean, cotton, or *Brassica* plant.

In still yet another aspect, a recombinant DNA molecule of the invention is provided that is present within a nonliving plant material. In one example, plant cells are within the scope of the invention when these contain a recombinant DNA molecule of the present invention. In one embodiment, such plant cells may be regenerable plant cells or may be non-regenerable plant cells not capable of being regenerated into a plant.

In still yet another aspect, the invention provides methods of producing commodity products that comprise a detectable amount of a recombinant DNA molecule of the invention, including the products produced thereby. In certain embodiments, commodity products provided by the invention include nonviable seeds or parts thereof, dehydrated plant tissue, frozen plant tissue, processed plant tissue, meal, flour, flakes, bran, and fiber. Commodity products may be viable or nonviable. Nonviable commodity products include but are not limited to nonviable seeds and grains; processed seeds, seed parts, and plant parts; dehydrated plant tissue, frozen plant tissue, and processed plant tissue. Commodity products of the invention contain a detectable amount of a recombinant DNA molecule as described herein. Methods for detecting a recombinant DNA molecule of the invention are well known in the art.

In a further aspect, the invention provides a method for producing an herbicide tolerant plant comprising the steps of a) transforming a plant cell with a DNA construct of the invention, and b) regenerating a plant from the transformed plant cell that comprises the DNA construct. In one embodiment of the method, the regenerated plant is tolerant to an herbicide selected from the group consisting of dicamba and a PPO inhibitor.

In yet another aspect, the invention provides a method of producing an herbicide tolerant plant comprising the steps of: a) crossing a parent plant comprising a recombinant DNA molecule of the invention with itself or with a second plant to produce one or more progeny plants; and b) selecting a progeny plant comprising said DNA molecule. In one embodiment of the method, the progeny plant is tolerant to an herbicide selected from the group consisting of dicamba and a PPO inhibitor.

In still another aspect, the invention provides a method for expressing an PPO or DMO in a plant cell comprising introducing a recombinant DNA molecule of the invention into a plant cell. In one embodiment of the invention, the introducing a recombinant DNA molecule comprises transforming the plant cell.

In another aspect, the invention provides a method for controlling weed growth in a crop growing environment comprising the steps of: a) planting a plant or seed of the invention in a crop growing environment; and b) applying to the crop growing environment an amount of dicamba or a PPO inhibitor herbicide effective to control weed growth. In specific embodiments, the herbicide application is made preor post-emergent. In one embodiment, the amount of herbicide does not damage the plant or seed. In certain embodiments of the method, the plant or seed is a monocot plant or seed, such as a maize or wheat plant or seed. In other embodiments, the plant or seed is a dicot plant or seed, such as a soybean, cotton, or *Brassica* plant. In further embodiments, the herbicide is dicamba or a PPO inhibitor.

BRIEF DESCRIPTION OF THE FIGURES

FIG. 1. Transgenic F1 maize plants expressing H_N10 (SEQ ID NO:43) operably linked to APG6 (SEQ ID NO:1) or 12G088600TP (SEQ ID NO:38) after herbicide application treatment of 0.036 lbs ai/acre S-3100 applied at V2 followed by V4 followed by V8.

BRIEF DESCRIPTION OF THE SEQUENCES

SEQ ID NO:1 is the amino acid sequence of the *Arabidopsis thaliana* albino and pale green (APG6) CTP.

SEQ ID NO:2 is the amino acid sequence of an aminoterminal optimized variant of the APG6 CTP of SEQ ID NO:1.

SEQ ID NO:3 is the amino acid sequence of the *Arabidopsis thaliana* 90 kDa heat shock protein (CR88) CTP.

SEQ ID NO:4 is the amino acid sequence of the Ph.ShkG-CTP4 CTP.

SEQ ID NO:5 is the amino acid sequence of the Ps.RbcS-3C CTP.

SEQ ID NO:6 is the amino acid sequence of the Os.Waxy CTP.

SEQ ID NO:7-11 are nucleic acid sequences encoding APG6 CTP of SEQ ID NO:1 optimized for monocot or dicot expression.

SEQ ID NO:12 is the nucleic acid sequence encoding APG6 CTP of SEQ ID NO:2.

SEQ ID NO:13 and 14 are nucleic acid sequences encoding At.CR88 CTP optimized for dicot or monocot expression, respectively.

SEQ ID NO:15-17 are nucleic acid sequences encoding SEQ ID NO:4-6, respectively.

SEQ ID NO:18-27 are amino acid sequences encoding dicamba monooxygenase (DMO) variants.

SEQ ID NO:28-37 are nucleic acid sequences encoding DMO variants of SEQ ID NO:18-27, respectively.

SEQ ID NO:38 is the amino acid sequence of the cotton 12G088600TP chloroplast transit peptide optimized for dicot expression.

SEQ ID NO:39 is nucleic acid sequences encoding SEQ ID NO:38.

SEQ ID NO:40 is the amino acid sequence of H_N90.
SEQ ID NO:41 is the amino acid sequence of H_N20.
SEQ ID NO:42 is the amino acid sequence of H_N60.
SEQ ID NO:43 is the amino acid sequence of H_N10.
SEQ ID NO:44 is the amino acid sequence of H_N30.
SEQ ID NO:45 is the amino acid sequence of H_N40.
SEQ ID NO:46 is the amino acid sequence of H_N50.
SEQ ID NO:47 is the amino acid sequence of H_N70.
SEQ ID NO:48 is the amino acid sequence of H_N100.
SEQ ID NO:49 is the amino acid sequence of H_N110.
SEQ ID NO:50-56 are amino acid sequences lacking the start methionine corresponding to SEQ ID NOs:40, 41, 43, 44, 45, 46, and 48, respectively.

SEQ ID NO:57-58 are amino acid variants of SEQ ID NO:50.

SEQ ID NO:59 is an amino acid variant of SEQ ID NO:56.

SEQ ID NO:60 is the amino acid sequence of the protoporphyrinogen oxidase from *Amaranthus tuberculatus* (waterhemp) (WH_PPO).

SEQ ID NO:61-70 are nucleotide sequences encoding SEQ ID NO:40-49, respectively, codon optimized for *E. coli* expression.

SEQ ID NO:71-80 are the nucleotide sequences encoding SEQ ID NO:40-49, respectively, codon optimized for dicot expression.

SEQ ID NO:81-87 are the nucleotide sequences encoding SEQ ID NO:50-56, respectively, codon optimized for dicot expression.

SEQ ID NO:88 and 91 are nucleotide variants of SEQ ID NO:50 and 51, respectively.

SEQ ID NOs:89, 90, and 92 are nucleotide sequences encoding SEQ ID NOs:57-59, respectively.

SEQ ID NO:93-102 are the nucleotide sequences encoding SEQ ID NO:40-49, respectively, codon optimized for monocot expression.

DETAILED DESCRIPTION

Chloroplast transit peptides (CTPs) for localizing herbicide tolerance proteins within cells are known in the art, but the degree of effective sub-cellular localization and processing for any CTP and herbicide tolerance protein combination is difficult to predict. Localization and processing determines the expression level and function of an herbicide tolerance protein and thus affects the herbicide tolerance phenotype of a transgenic cell, plant, or seed comprising the protein. Various CTPs have been tested with useful herbicide tolerance proteins including dicamba monooxygenases (DMO) and protoporphyrinogen oxidases (PPO) in transgenic plants. However, poor or incomplete processing and localization of the protein is often seen.

The invention overcomes these obstacles by providing novel recombinant DNA molecules capable of providing improved chloroplast localization and processing, as well as compositions and methods for using these. Recombinant DNA molecules of the invention comprise a DNA sequence encoding a CTP operably linked to DMO or PPO. The recombinant DNA molecules of the invention provide for chloroplast localization of DMO or PPO and improved tolerance to dicamba or PPO herbicide in plants comprising the recombinant DNA molecules.

In certain embodiments, the invention provides recombinant DNA molecules comprising a DNA sequence encoding a CTP comprising a sequence selected from the group consisting of SEQ ID NOs:1-3 operably linked to a DNA sequence encoding an herbicide tolerance protein. In some embodiments, the invention provides recombinant DNA molecules comprising DNA sequences encoding CTPs, such as a CTP having a sequence selected from the group consisting of SEQ ID NOs:1-3, operably linked to a DNA sequence encoding a DMO protein, for example a DMO protein having a sequence selected from the group consisting of SEQ ID NOs:18-27. In further embodiments, the invention provides recombinant DNA molecules comprising DNA sequences encoding CTPs, such as a CTP having a sequence selected from the group consisting of SEQ ID NOs:1-3, operably linked to a DNA sequence encoding a PPO protein, such as a PPO protein having a sequence selected from the group consisting of SEQ ID NOs:40-60.

Recombinant DNA Molecules

As used herein, the term "recombinant" refers to a non-natural DNA, polypeptide, protein, cell, seed, or plant that is the result of genetic engineering and as such would not normally be found in nature and was created by human intervention. A "recombinant DNA molecule" is a DNA molecule comprising a DNA sequence that does not naturally occur and that is the result of human intervention, such as a DNA molecule comprised of a combination of at least two DNA molecules heterologous to each other. An example of a recombinant DNA molecule is a DNA molecule encoding a CTP comprising a sequence selected from the group consisting of SEQ ID NOs:1-3 operably linked to a DNA sequence encoding a DMO protein comprising a sequence selected from the group consisting of SEQ ID NOs:18-27. Examples of DMO proteins are provided in Table 1 below.

TABLE 1

Dicamba Monooxygenases (DMO)

| PRT SEQ ID NO | DNA SEQ ID NO | PRT length | Predicted position 2 | Predicted position 3 | Predicted position 112 | Codon Usage |
|---|---|---|---|---|---|---|
| 18 | 28 | 340 | Leu | Thr | Trp | dicot |
| 19 | 29 | 339 | Thr | Phe | Trp (at 111) | dicot |
| 20 | 30 | 340 | Leu | Thr | Trp | monocot |
| 21 | 31 | 340 | Ala | Thr | Cys | dicot |
| 11 | 32 | 340 | Leu | Thr | Cys | dicot |
| 23 | 33 | 340 | Ala | Thr | Cys | bacterial |
| 24 | 34 | 340 | Ala | Thr | Trp | dicot |
| 25 | 35 | 340 | Ala | Thr | Trp | monocot |
| 26 | 36 | 340 | Leu | Thr | Cys | dicot |
| 27 | 37 | 340 | Leu | Thr | Trp | dicot |

Another example of a recombinant DNA molecule is a DNA molecule encoding a CTP comprising a sequence selected from the group consisting of SEQ ID NOs:1-3 operably linked to DNA sequence encoding a PPO protein comprising a sequence selected from the group consisting of SEQ ID NOs:40-60. A recombinant cell, seed, or plant is a cell, seed, or plant comprising transgenic DNA, for example a transgenic cell, seed, plant, or plant part comprising a recombinant DNA molecule of the invention. Examples of PPO proteins are provided in Table 2 below.

TABLE 2

Protoporphyrinogen oxidases (PPO)

| PPO | Protein SEQ ID NO | Bacterial DNA SEQ ID NO | Dicot optimized DNA SEQ ID NO | Monocot optimized DNA SEQ ID NO |
|---|---|---|---|---|
| H_N10 | 43, 52 | 64 | 74, 83 | 96 |
| H_N20 | 41, 51 | 62 | 72, 82, 91 | 94 |
| H_N30 | 44, 53 | 65 | 75, 84 | 97 |
| H_N40 | 45, 54 | 66 | 76, 85 | 98 |
| H_N50 | 46, 55 | 67 | 77, 86 | 99 |
| H_N60 | 42 | 63 | 73 | 95 |
| H_N70 | 47 | 68 | 78 | 100 |
| H_N90 | 40, 50, 57, 58 | 61 | 71, 81, 88, 89, 90 | 93 |
| H_N100 | 48, 56, 59 | 69 | 79, 87, 92 | 101 |
| H_N110 | 49 | 70 | 80 | 102 |
| WH_PPO | 60 | n/a | n/a | n/a |

Examples of CTP sequences that may be used in accordance with the invention are provided in Table 3 below.

TABLE 3

Chloroplast Transit Peptides (CTP)

| CTP | PRT SEQ ID NO | DNA SEQ ID NO | Codon Usage |
|---|---|---|---|
| APG6 | 1 | 7, 10, 11 | monocot |
|  |  | 8, 9 | dicot |
| N-opt APG6 | 2 | 12 | dicot |
| At.CR88 | 3 | 13 | dicot |
|  |  | 14 | monocot |
| Ph.ShkG-CTP4 | 4 | 15 | monocot |
| Ps.RbcS-3C | 5 | 16 | dicot |
| Os.waxy | 6 | 17 | monocot |
| 12G088600TP | 38 | 39 | dicot |

As used herein, the term "isolated DNA molecule" means that a DNA molecule is present alone or in combination with other compositions but is not within its natural environment. For example, a recombinant DNA molecule comprising a protein-coding sequence and heterologous CTP sequence is an isolated DNA molecule when present in the genome of a transgenic plant, cell, or seed since the components of that recombinant DNA molecule are not in their natural environment (that is, the genome of the organism in which each component was first observed). A recombinant DNA molecule present in a transgenic plant genome is an isolated DNA molecule so long as the recombinant DNA molecule was not naturally found in that plant genome and thus is isolated from its natural environment.

As used herein, the term "genetic engineering" refers to the creation by human intervention of a DNA, protein, or organism that would not normally be found in nature. Genetic engineering can be used to produce a DNA, polypeptide, protein, cell, seed, or plant that was conceived of and created in the laboratory using one or more of the techniques of biotechnology such as molecular biology, protein biochemistry, bacterial transformation, and plant transformation. For example, genetic engineering can be used to create a chimeric gene comprising a DNA molecule encoding a CTP comprising a sequence selected from the group consisting of SEQ ID NOs:1-3, operably linked to a DMO protein comprising a sequence selected from the group consisting of SEQ ID NOs:18-27, and optionally may further comprise a heterologous promoter functional in a plant cell. In another example, genetic engineering can be used to create a chimeric gene comprising a DNA molecule encoding a CTP comprising a sequence selected from the group consisting of SEQ ID NO:1-3, operably linked to a PPO protein comprising a sequence selected from the group consisting of SEQ ID NOs:40-60, and optionally may further comprise a heterologous promoter functional in a plant cell. Such a chimeric gene may be produced using one or more of the techniques of molecular biology, such as gene cloning, DNA ligation, and DNA synthesis.

The term "transgene" refers to a DNA molecule artificially incorporated into an organism's genome as a result of human intervention, such as by plant transformation methods. As used herein, the term "transgenic" means comprising a transgene, for example a "transgenic plant" refers to a plant comprising a transgene in its genome and a "transgenic trait" refers to a characteristic or phenotype conveyed or conferred by the presence of a transgene incorporated into the plant genome. As a result of such genomic alteration, the transgenic plant is something distinctly different from the related wild-type plant and the transgenic trait is a trait not naturally found in the wild-type plant. Transgenic plants of the invention comprise the recombinant DNA molecules provided by the invention.

As used herein, the term "heterologous" refers to the relationship between two or more materials derived from different sources and thus not normally associated in nature. For example, a DMO protein is heterologous with respect to an operably linked CTP if such combination is not normally found in nature. In another example, a recombinant DNA molecule encoding a CTP operably linked to a DMO protein is heterologous with respect to an operably linked promoter that is functional in a plant cell if such combination is not normally found in nature. A particular recombinant DNA molecule also may be heterologous with respect to a cell, seed, or organism into which it is inserted when it would not naturally occur in that particular cell, seed, or organism.

As used herein, the term "protein-coding DNA molecule" or "polypeptide-coding DNA molecule" refers to a DNA molecule comprising a DNA sequence that encodes a protein or polypeptide, such as a protein or polypeptide for conferring herbicide tolerance or insect control. A "protein-coding sequence" or "polypeptide-coding sequence" means a DNA sequence that encodes a protein or polypeptide. A "sequence" means a sequential arrangement of nucleotides or amino acids. The boundaries of a protein-coding sequence or polypeptide-coding sequence are usually determined by a translation start codon at the 5'-terminus and a translation stop codon at the 3'-terminus. A protein-coding molecule or polypeptide-coding molecule may comprise a DNA sequence encoding a protein or polypeptide sequence. As used herein, "transgene expression", "expressing a transgene", "protein expression", "polypeptide expression", "expressing a protein", and "expressing a polypeptide" mean the production of a protein or polypeptide through the process of transcribing a DNA molecule into messenger RNA (mRNA) and translating the mRNA into polypeptide chains, which may be ultimately folded into proteins. A protein-coding DNA molecule or polypeptide-coding DNA molecule may be operably linked to a heterologous promoter in a DNA construct for use in expressing the protein or polypeptide in a cell transformed with the recombinant DNA molecule. As used herein, "operably linked" means two DNA molecules linked in manner so that one may affect the function of the other. Operably-linked DNA molecules may be part of a single contiguous molecule and may or may not be adjacent. For example, a promoter is operably linked with a protein-coding DNA molecule or polypeptide-coding DNA molecule in a DNA construct where the two DNA molecules are so arranged that the promoter may affect the expression of the transgene.

The recombinant DNA molecules of the invention include a DNA sequence encoding a DMO operably linked to a CTP sequence. As used herein, "dicamba monooxygenase" or "DMO" means an oxygenase capable of enzymatically catalyzing the degradation of dicamba (3,6-dichloro-o-anisic acid) to 3,6-dichlorosalicylic acid (3,6-DCSA), such as the dicamba monooxygenase encoded by the demethylase (dmo) gene from Stenotrophomonas maltophilia. Dicamba monooxygenases are known in the art and include the protein sequences provided as SEQ ID NOs:18-27 and identified in Table 1.

The recombinant DNA molecules of the invention include a DNA sequence encoding a PPO operably linked to a CTP sequence. As used herein, "protoporphyrinogen oxidase" or "PPO" means an oxidase capable of enzymatically converting protoporphyrinogen IX to protoporphyrin IX. Protoporphyrinogen oxidases are known in the art and include the protein sequences provided as SEQ ID NOs:40-60 and identified in Table 2.

The recombinant DNA molecules of the invention include a DNA sequence encoding a CTP sequence operably linked to the protein-coding DNA molecules provided by the invention, whereby the CTP facilitates localizing the recombinant protein molecule within the cell. CTPs are also known in the art as signal sequences, targeting sequences, targeting peptides, and localization sequences. Chloroplasts are also known in the art as plastids. By facilitating protein localization within the cell, the CTP ensures localization of a protein to the chloroplast for optimal enzyme activity and may increase the accumulation of recombinant protein and protect the protein from proteolytic degradation. Upon translocation into the chloroplast, the CTP is typically cleaved from the protein, also referred to as processing. CTP processing may be complete (meaning that the complete CTP is cleaved from the amino-terminal end of the protein), incomplete (meaning that one or more amino acids of the CTP remain on amino-terminal end of the protein), or result in removal one or more amino acids from the amino-terminal end of the protein. Complete processing of the CTP from a DMO protein increases the level of protein accumulation, thereby increasing dicamba tolerance and reducing levels of injury in the transgenic cell, seed, or organism after herbicide application. CTPs are provided as SEQ ID NOs:1-6 and 38, and identified in Table 3. The DNA sequence encoding each CTP, optimized for expression in dicots and monocots, is provided as SEQ ID NOs:7-17 and 39.

Recombinant DNA molecules of this disclosure may be synthesized and modified by methods known in the art, either completely or in part, especially where it is desirable to provide sequences useful for DNA manipulation (such as restriction enzyme recognition sites or recombination-based cloning sites), plant-preferred sequences (such as plant-codon usage or Kozak consensus sequences), or sequences useful for DNA construct design (such as spacer or linker sequences). Recombinant DNA molecules of this disclosure include degenerated DNA sequences encoding the same amino acid sequence as a DNA sequence provided herein. Degenerated DNA sequences can be made using methods known in the art and the DNA codon table. This invention includes recombinant DNA molecules and proteins having at least 85% sequence identity, at least 90% sequence identity, at least 95% sequence identity, at least 96% sequence identity, at least 97% sequence identity, at least 98% sequence identity, and at least 99% sequence identity to any of the recombinant DNA molecule or polypeptide sequences provided herein. For example, a recombinant DNA molecule of the invention may comprise a DNA sequence having at least 85%, at least 90%, at least 95%, at least 96%, at least 97%, at least 98%, at least 99%, or 100% sequence identity to a sequence selected from the group consisting of SEQ ID NOs:7-14 or to a sequence selected from the group consisting of SEQ ID NOs:28-37 and 61-102. A recombinant DNA molecule of the invention may encode a protein sequence having at least 85%, at least 90%, at least 95%, at least 96%, at least 97%, at least 98%, at least 99%, or 100% sequence identity to a sequence selected from the group consisting of SEQ ID NOs:1-3; or to a sequence selected from the group consisting of SEQ ID NOs:18-27 and 40-59.

As used herein, the term "percent sequence identity" or "% sequence identity" refers to the percentage of identical nucleotides or amino acids in a linear polynucleotide or polypeptide sequence of a reference ("query") sequence (or its complementary strand) as compared to a test ("subject")

sequence (or its complementary strand) when the two sequences are optimally aligned (with appropriate nucleotide or amino acid insertions, deletions, or gaps totaling less than 20 percent of the reference sequence over the window of comparison). Optimal alignment of sequences for aligning a comparison window are well known to those skilled in the art and may be conducted by tools such as the local homology algorithm of Smith and Waterman, the homology alignment algorithm of Needleman and Wunsch, the search for similarity method of Pearson and Lipman, and by computerized implementations of these algorithms such as GAP, BESTFIT, FASTA, and TFASTA available as part of the Sequence Analysis software package of the GCG® Wisconsin Package® (Accelrys Inc., San Diego, Calif.), MEGAlign (DNAStar Inc., 1228 S. Park St., Madison, Wis. 53715), and MUSCLE (version 3.6) (Edgar, Nucleic Acids Research 32(5):1792-7, 2004) with default parameters. An "identity fraction" for aligned segments of a test sequence and a reference sequence is the number of identical components which are shared by the two aligned sequences divided by the total number of components in the reference sequence segment, that is, the entire reference sequence or a smaller defined part of the reference sequence. Percent sequence identity is represented as the identity fraction multiplied by 100. The comparison of one or more sequences may be to a full-length sequence or a portion thereof, or to a longer sequence.

As used herein, a "DNA construct" is a recombinant DNA molecule comprising two or more heterologous DNA sequences. DNA constructs are useful for transgene expression and may be comprised in vectors and plasmids. DNA constructs may be used in vectors for the purpose of transformation, that is the introduction of heterologous DNA into a host cell, in order to produce transgenic plants and cells, and as such may also be contained in the plastid DNA or genomic DNA of a transgenic plant, seed, cell, or plant part. As used herein, a "vector" means any recombinant DNA molecule that may be used for the purpose of plant transformation. Recombinant DNA molecules as set forth in the sequence listing, can, for example, be inserted into a vector as part of a construct having the recombinant DNA molecule operably linked to a gene expression element that functions in a plant to affect expression of the protein encoded by the recombinant DNA molecule. Methods for constructing DNA constructs and vectors are well known in the art. The components for a DNA construct, or a vector comprising a DNA construct, generally include one or more gene expression elements operably linked to a transcribable DNA sequence, such as the following: a promoter for the expression of an operably linked DNA, an operably linked protein-coding DNA molecule, and a 3' untranslated region. Gene expression elements useful in practicing the invention include, but are not limited to, one or more of the following type of elements: promoter, 5' untranslated region, enhancer, leader, cis-acting element, intron, 3' untranslated region, and one or more selectable marker transgenes.

The DNA constructs of the invention may include a promoter operably linked to a protein-coding DNA molecule provided by the invention, whereby the promoter drives expression of the recombinant protein molecule. Promoters useful in practicing the invention include those that function in a cell for expression of an operably linked polynucleotide, such as a bacterial or plant promoter. Plant promoters are varied and well known in the art and include those that are inducible, viral, synthetic, constitutive, temporally regulated, spatially regulated, and/or spatio-temporally regulated.

As used herein, "negative control" and "positive control" mean an experimental control designed for comparison purposes. For example, a negative control or positive control in a transgenic plant analysis may be a plant of the same type as the experimental plant (that its, the plant to be tested) but does not contain the transgenic insert, recombinant DNA molecule, or DNA construct of the experimental plant. An example of a plant useful for comparison with transgenic maize plants is non-transgenic LH244 maize (U.S. Pat. No. 6,252,148), or non-transgenic 01DKD2 maize (U.S. Pat. No. 7,166,779), for comparison with transgenic soybean plants is non-transgenic A3555 soybean (U.S. Pat. No. 7,700,846), or non-transgenic A3244 soybean (U.S. Pat. No. 5,659,114, PVP 9600246), for comparison with transgenic canola or *Brassica napus* plants is non-transgenic *Brassica napus* variety 65037 Restorer line, for comparison with transgenic wheat plants is non-transgenic wheat variety Samson germplasm (PVP 1994), and for comparison with transgenic cotton plants is non-transgenic DP393 (U.S. Pat. No. 6,930, 228 PVP 200400266).

Transgenic Plants

An aspect of the invention includes transgenic plant cells, transgenic plant tissues, transgenic plants, and transgenic seeds that comprise the recombinant DNA molecules provided by the invention. These cells, tissues, plants, and seeds comprising the recombinant DNA molecules exhibit tolerance to herbicides.

Inserting transgenic DNA (known as a "transgene") into the genome of a plant may be accomplished by the act of plant transformation and results in the creation of a new transgenic genomic molecular sequence, known as an "event". Each event is unique and the DNA sequence of the event is specific for the event. Suitable methods for transformation of host plant cells for use with the current invention include virtually any method by which DNA can be introduced into a cell (for example, where a recombinant DNA construct is stably integrated into a plant chromosome) and are well known in the art. A recombinant DNA construct inserted into Exemplary methods for introducing a recombinant DNA construct into plants include the *Agrobacterium* transformation system and DNA particle-bombardment, both of which are well known to those of skill in the art. Another exemplary method for introducing a recombinant DNA construct into plants is insertion of a recombinant DNA construct into a plant genome at a pre-determined site by methods of site-directed integration. Site-directed integration may be accomplished by any method known in the art, for example, by use of zinc-finger nucleases, engineered or native meganucleases, TALE-endonucleases, or an RNA-guided endonuclease (for example a CRISPR/Cas9 system). Transgenic plants then can be regenerated from a transformed plant cell by the methods of plant cell culture. A transgenic plant homozygous with respect to a transgene (that is, two allelic copies of the transgene) can be obtained by self-pollinating (selfing) a transgenic plant that contains a single transgene allele with itself, for example an R0 plant, to produce R1 seed. One fourth of the R1 seed produced will be homozygous with respect to the transgene. Plants grown from germinating R1 seed can be tested for zygosity, typically using a SNP assay, DNA sequencing, or a thermal amplification assay that allows for the distinction between heterozygotes and homozygotes, referred to as a zygosity assay.

Plants, seeds, plant parts, plant tissues, and cells provided by the invention may exhibit herbicide tolerance to dicamba. Dicamba may be applied to a plant growth area comprising the plants and seeds provided by the invention as a method for controlling weeds, including preventing weed growth. Plants and seeds provided by the invention comprise an herbicide tolerance trait and as such are tolerant to the application of dicamba. The herbicide application may be the recommended commercial rate (1×) or any fraction or multiple thereof, such as twice the recommended commercial rate (2×). Dicamba application rates may be expressed as acid equivalent per pound per acre (lb ae/acre) or acid equivalent per gram per hectare (g ae/ha). The plant growth area may or may not comprise weed plants at the time of herbicide application. An herbicidally effective dose of dicamba for use in an area for controlling weeds should consist of a range from about 0.1× to about 30× label rate(s) over a growing season. The 1× label rate for dicamba is 0.5 lb ae/acre. Herbicide rates can be converted between English and metric as: (lb ai/ac)*1.12=(kg ai/ha) and (kg ai/ha)*0.89=(lb ai/ac).

Plants, seed, plant parts, plant tissues, and cells may exhibit tolerance to one or more PPO inhibitors, referred to as PPO herbicides. One or more PPO herbicides may be applied to a plant growth area comprising the plants and seeds provided by the invention as a method for controlling weeds, including preventing weed growth. Plants and seeds provided by the invention comprise an herbicide tolerance trait and as such are tolerant to the application of one or more PPO herbicides. The herbicide application may be the recommended commercial rate (1×) or any fraction or multiple thereof, such as twice the recommended commercial rate (2×). The plant growth area may or may not comprise weed plants at the time of herbicide application. An herbicidally effective dose of a PPO herbicide for use in an area for controlling weeds should consist of a range from about 0.1× to about 30× label rate(s) over a growing season. PPO herbicides are well-known in the art and commercially available. Examples of PPO herbicides include, but are not limited to, diphenylethers (such as acifluorfen, its salts and esters, aclonifen, bifenox, its salts and esters, ethoxyfen, its salts and esters, fluoronitrofen, furyloxyfen, halosafen, chlomethoxyfen, fluoroglycofen, its salts and esters, lactofen, its salts and esters, oxyfluorfen, and fomesafen, its salts and esters); thiadiazoles (such as fluthiacet-methyl and thidiazimin); pyrimidinediones or phenyluracils (such as benzfendizone, butafenacil, ethyl [3-2-chloro-4-fluoro-5-(1-methyl-6-trifluoromethyl-2,4-dioxo-1,2,3,4-tetrahydropyrimidin-3-yl)phenoxy]-2-pyridyloxyl acetate (CAS Registry Number 353292-31-6 and referred to herein as S-3100), flupropacil, saflufenacil, and tiafenacil); phenylpyrazoles (such as fluazolate, pyraflufen and pyraflufen-ethyl); oxadiazoles (such as oxadiargyl and oxadiazon); triazolinones (such as azafenidin, bencarbazone, carfentrazone, its salts and esters, and sulfentrazone); oxazolidinediones (such as pentoxazone); N-phenylphthalimides (such as cinidon-ethyl, flumiclorac, flumiclorac-pentyl, and flumioxazin); benzoxazinone derivatives (such as 1,5-dimethyl-6-thioxo-3-(2,2,7-trifluoro-3,4-dihydro-3-oxo-4-prop-2-ynyl-2H-1,4-benzoxazin-6-yl)-1,3,5-triazinane-2,4-dione); flufenpyr and flufenpyr-ethyl; pyraclonil; and profluazol.

Herbicide applications may be sequentially or tank mixed with one, two, or a combination of several herbicides or any other compatible herbicide. Multiple applications of one herbicide or of two or more herbicides, in combination or alone, may be used over a growing season to areas comprising transgenic plants of the invention for the control of a broad spectrum of dicot weeds, monocot weeds, or both, for example, two applications (such as a pre-planting application and a post-emergence application or a pre-emergence application and a post-emergence application) or three applications (such as a pre-planting application, a pre-emergence application, and a post-emergence application or a pre-emergence application and two post-emergence applications).

As used herein, "tolerance" or "herbicide tolerance" means the ability of a plant, seed, or cell to resist the toxic effects of an herbicide when applied. The herbicide tolerance of a plant, seed, plant tissue, plant part, or cell may be measured by comparing the plant, seed, plant tissue, plant part, or cell to a suitable experimental control. For example, the herbicide tolerance may be measured or assessed by applying an herbicide to a plant comprising a recombinant DNA molecule encoding a protein capable of conferring herbicide tolerance (the test plant) and a plant of the same species not comprising the recombinant DNA molecule encoding the protein capable of conferring herbicide tolerance (the negative control plant) and then comparing the plant injury of the two plants, where herbicide tolerance of the test plant is indicated by a decreased injury rate as compared to the injury rate of the negative control plant. An herbicide tolerant plant, seed, plant tissue, plant part, or cells exhibits a decreased response to the toxic effects of an herbicide when compared to a negative control plant, seed, plant tissue, plant part, or cell. As used herein, an "herbicide tolerance trait" is a transgenic trait imparting improved herbicide tolerance to a plant as compared to a negative control plant.

The transgenic plants, progeny, seeds, plant cells, and plant parts of the invention may also contain one or more additional transgenic traits. Additional transgenic traits may be introduced by crossing a plant containing a transgene comprising the recombinant DNA molecules provided by the invention with another plant containing an additional transgenic trait(s). As used herein, "crossing" means breeding two individual plants to produce a progeny plant. Two transgenic plants may thus be crossed to produce progeny that contain the transgenic traits. As used herein "progeny" means the offspring of any generation of a parent plant, and transgenic progeny comprise a DNA construct provided by the invention and inherited from at least one parent plant. Alternatively, additional transgenic trait(s) may be introduced by co-transforming a DNA construct for that additional transgenic trait(s) with a DNA construct comprising the recombinant DNA molecules provided by the invention (for example, with all the DNA constructs present as part of the same vector used for plant transformation) or by inserting the additional trait(s) into a transgenic plant comprising a DNA construct provided by the invention or vice versa (for example, by using any of the methods of plant transformation on a transgenic plant or plant cell). Such additional transgenic traits include, but are not limited to, increased insect resistance, increased water use efficiency, increased yield performance, increased drought resistance, increased seed quality, improved nutritional quality, hybrid seed production, and herbicide tolerance, in which the trait is measured with respect to a wild-type plant. Such additional transgenic traits are known to one of skill in the art; for example, a list of such traits is provided the United States Department of Agriculture's (USDA) Animal and Plant Health Inspection Service (APHIS).

Transgenic plants and progeny that contain a transgenic trait provided by the invention may be used with any breeding methods that are commonly known in the art. In plant lines comprising two or more transgenic traits, the transgenic traits may be independently segregating, linked, or a combination of both in plant lines comprising three or more transgenic traits. Back-crossing to a parental plant and out-crossing with a non-transgenic plant are also contemplated, as is vegetative propagation. Descriptions of breeding methods that are commonly used for different traits and crops are well known to those of skill in the art. To confirm the presence of the transgene(s) in a particular plant or seed, a variety of assays may be performed. Such assays include, for example, molecular biology assays, such as Southern and northern blotting, PCR, and DNA sequencing; biochemical assays, such as detecting the presence of a protein product, for example, by immunological means (ELISAs and Western blots) or by enzymatic function; plant part assays, such as leaf or root assays; and also, by analyzing the phenotype of the whole plant. To analyze CTP processing in a particular transgenic plant or seed, assays such as Edman degradation sequencing or mass spectrometry analysis may be performed on the recombinant DMO or PPO protein obtained from the transgenic cell, plant, or seed and the resulting sequence data compared to that of the DMO or PPO protein, respectively.

Introgression of a transgenic trait into a plant genotype is achieved as the result of the process of backcross conversion. A plant genotype into which a transgenic trait has been introgressed may be referred to as a backcross converted genotype, line, inbred, or hybrid. Similarly a plant genotype lacking the desired transgenic trait may be referred to as an unconverted genotype, line, inbred, or hybrid.

As used herein, the term "comprising" means "including but not limited to".

EXAMPLES

The following examples are included to demonstrate embodiments of the invention. It should be appreciated by those of skill in the art that, in light of the present disclosure, many changes can be made in the specific embodiments that are provided and still obtain a like or similar result without departing from the scope and concept scope of the invention. More specifically, it will be apparent that certain agents that are chemically or physiologically related may be substituted for the agents described herein with the same or similar result achieved. All such similar substitutes and modifications apparent to those skilled in the art are deemed to be within the scope and concept of the invention.

Example 1: CTP-DMO Expression and Localization in Soybean Protoplasts

A soybean protoplast assay was used to assess the relative chloroplast targeting efficiency of recombinant protein comprising one of five CTPs operably linked to a DMO sequence (SEQ ID NO:27). To monitor cytosol and chloroplast distribution of the recombinant protein, a sequence encoding a green fluorescent protein was added to the cassette encoding the recombinant CTP and DMO combination (referred to herein as CTP-DMO) such that the green fluorescent protein was fused to the carboxy-terminal end of the DMO.

Protoplasts were prepared from bean cotyledon (germplasm A3244). Immature soybean seed pods were harvested and the seeds (4-6 mm long) were removed using sterile technique. The cotyledon from each seed was manually removed, sliced transversely into 1 mm pieces, and incubated in CPW buffer (pH 5.8) with 0.7 M mannitol for 1 hour at 24-26° C. in the dark while shaking at 40 RPM. The buffer was then removed and replaced with enzyme buffer (4% Cellulase 'onozuka' R-10; 2% Hemicellulase; 0.3% Macerozyme R-10; in CPW buffer (pH 5.8; with 0.49 M mannitol). The cotyledon tissue was incubated on a rotary shaker at 50 rpm at 24-26° C. for 2 hours. Soybean protoplasts were released from the cotyledon tissue at the end of this incubation by swirling the plate manually and filtering the suspension through a double layer of 60 um nylon mesh into a 50 mL conical tube. The protoplasts were gently washed once with resuspension and centrifugation. The final pellet was resuspended in buffer (4 mM MES, pH 5.7; 150 mM NaCl; 5 mM CaCl2; 0.5 M Mannitol) and rested for 1 hour on ice. The protoplasts were then centrifuged and the pellet was resuspended in transformation buffer (0.4 M Mannitol; 15 mM MgCl2; 4 mM MES, pH 5.7). The volume was adjusted to allow 1×10,000,000 protoplasts/ml. Transformation was accomplished by mixing 12.5 μg DNA for each construct. The DNA was gently combined with 1.5× 1,000,000 protoplasts, followed by addition of an equal volume of PEG buffer. This was incubated for 5 minutes then slowly diluted with 300 μl of W5 buffer (154 mM NaCl; 125 mM CaCl$_2$; 5 mM KCl; 2 mM MES, pH 5.7). This was incubated 5-10 minutes and then 900 μl of W5 buffer was slowly added. The protoplasts were pelleted and resuspended in WI buffer (0.5 M Mannitol; 4 mM MES (pH 5.7); 20 mM KCl) and incubated at 24-26° C. in the dark. Microscopy analysis was performed using a Zeiss LSM510 META Laser Scanning Microscope (Carl Zeiss MicroImaging, Inc., Thornwood, N.Y.) equipped with a Krypton-Argon Ion (458, 488 nm) laser, a green (543 nm) Helium-Neon laser, and FITC and Texas red filter sets. Image acquisition and analysis was performed using ZEN 2012 v.8.1 (Carl Zeiss MicroImaging, Inc., Thornwood, N.Y.) and a 40× water 1.2 numerical aperture objective. Excitation wavelengths used were 488 nm (GFP) and 543 nm (chloroplast auto-fluorescence), and emission filters were 500-530 nm (GFP) and 630-700 nm (chloroplast auto-fluorescence). For each construct, at least 50 individual cells were scored for localization of the construct: cytosol, plastid, or both cytosol and plastid. Results were recorded as the percentage of cells having protein localized in the cytosol or plastid (or both) of the total number of cells analyzed and are provided in Table 4.

TABLE 4

Soybean protoplast targeting assay

| CTP | Total cells scored | Cytosol | Cytosol and plastid | Plastid |
|---|---|---|---|---|
| APG6 (SEQ ID NO: 1) | 58 | 0 | 0 | 100% |
| At.CR88 (SEQ ID NO: 3) | 53 | 0 | 6% | 94% |
| A | 53 | 0 | 21% | 79% |
| B | 54 | 0 | 91% | 9% |
| C | 56 | 0 | 82% | 18% |
| none | 55 | 100% | 0 | 0 |

Of the five CTP-DMO combinations analyzed, only the APG6 CTP (SEQ ID NO:1) resulted in 100% of the cells showing localization of the protein solely to the plastid. The At.CR88 CTP (SEQ ID NO:3) resulted in 94% of the cells showing localization of the protein solely to the plastid and 6% of the cells showing localization of the protein to cytosol and plastid. The 'A' CTP resulted in 79% of the cells showing localization of the protein solely to plastids and 21% of the cells showing localization to cytosol and plastid. The 'B' CTP resulted in 9% of the cells showing localization of the protein solely to plastid and 91% of the cells showing localization to plastids and cytosol. The 'C' CTP resulted in 18% of the cells showing localization of the protein solely to plastid and 82% of the cells showing localization to plastids and cytosol. Without a CTP, the protein was present only in the cytosol. These results indicate that the APG6

CTP was 100% efficient for targeting the CTP-DMO to plastids and the At.CR88 CTP was 94% efficient for targeting the CTP-DMO to plastids.

Example 2: CTP-DMO Processing in Transgenic Wheat

Transgenic wheat plants transformed with a DNA construct comprising a recombinant DNA molecule encoding one of four separate CTPs operably linked to DMO were used to assess protein expression and to determine CTP processing.

Transgenic wheat plants were produced using four different plant transformation vectors each comprising a DNA construct containing one of four different CTPs operably linked to DMO operably linked to a promoter. Pre-cultured immature embryos from wheat of Samson germplasm (PVP 1994) were transformed using *Agrobacterium tumefaciens* to produce transgenic plantlets using methods known to those of skill in the art. Leaf samples were taken for molecular analysis to confirm the transgene copy number in the genome of each unique event, and R0 plants with one copy of the transgene were selfed and R1 seed collected.

The seed (50 g) was ground to a powder, which was then added to 250 ml extraction buffer (1×TBE (89 mM Tris-borate, 2 mM EDTA, pH 8.4), 200 mM NaCl, 10% glycerin, 1 mM phenylmethylsulfonyl fluoride (PMSF), 5 mM benzamidin, 2 mM dithiothreitol (DTT), cOmplete™ protease inhibitors (Roche Diagnostics Corporation, Indianapolis, Ind.)), and homogenized with a Polytron® (VWR, Radnor, Pa.) for about 20 seconds, then incubated with shaking at 4° C. for 1 to 2 hours. The mixture was centrifuged at 4° C. for 25 min at 9,000 rpm and the supernatant was precipitated sequentially with 10% and 55% saturated ammonium sulfate (AS), with each precipitation step centrifuged at 18,000 rpm for 20 minutes. The pellet from the 10% AS precipitation was discarded.

The pellet from the 10-55% fraction was dissolved in 30 ml of PBS (0.1 M sodium phosphate, 0.15 M NaCl) with 1 tablet of the cOmplete™ protease inhibitors. The dissolved pellet was centrifuged and the supernatant was filtered through a 0.22 um membrane. A goat polyclonal antibody sera against DMO was mixed with a 1:1 suspension of Pierce™ protein A/G agarose resin (ThermoFischer Scientific, Grand Island, N.Y.), after 1.5 hours the anti-DMO Ab loaded protein A/G agarose resin was washed 3 times with PBS and added to about 30 ml of the 10%-55% AS filtered fraction. After incubation, the resin was spun and washed 3 times with PBS, then resuspended in 1 ml PBS and transferred to a microcentrifuge tube and pelleted again.

The final pellet was resuspended in 2× Laemmli buffer, boiled for 5 minutes, and the samples run on a 10% SDS-PAGE gel in Tris-glycine buffer at 185 V (constant). The proteins in the SDS-PAGE gel were transferred to PVDF membrane using CAPS transfer buffer, for 30 min at 4° C. and 100V. The PDVF membrane bound proteins were stained with Coomassie blue for approximately 30 seconds and the band corresponding to each of the DMO proteins in the 10%-55% AS fraction was excised from the PVDF blot and used for amino-terminal protein sequence analysis. Amino-terminal protein sequencing was carried out by automated Edman degradation chemistry, with each analysis performed for 15 cycles using automated Edman degradation chemistry. An Applied Biosystems 494 Procise® Sequencing System with 140C Microgradient pump and Perkin Elmer Series 200 UV/Vis Detector was used for the analysis with controlled with Procise Control (version 2.1) software (ThermoFischer Scientific, Grand Island, N.Y.). Chromatographic data were collected using SequencePro® (version 2.1) protein sequencing analysis software. Identity was established for each protein if at least 8 amino acids consistent with the predicted sequence of the expected protein were observed. The results of the amino-terminal sequencing are presented in Table 5.

TABLE 5

Amino-terminal sequencing of recombinant protein

| Events tested | CTP | DMO | CTP-DMO processing |
|---|---|---|---|
| 2 | APG6 (SEQ ID NO: 1) | DMO (SEQ ID NO: 18) | DMO + 1 |
| 3 | At.CR88 (SEQ ID NO: 3) | DMO (SEQ ID NO: 18) | DMO and DMO + 1 |
| 1 | CTP4 (SEQ ID NO: 4) | DMO (SEQ ID NO: 19) | DMO + 12 |
| 2 | Os.Waxy (SEQ ID NO: 6) | DMO (SEQ ID NO: 18) | DMO + 10 and DMO − 1 |

The designations of DMO, DMO+1, DMO+10, and DMO+12 were used to indicate that protein sequencing indicated that there were 0, 1, 10, or 12 amino acids of the CTP remaining on the amino-terminal end of the DMO after processing, respectively. The designation of DMO-1 was used to indicate that the first methionine of the DMO was removed after processing. Two unique events were tested for the APG6 CTP (SEQ ID NO:1) operably linked to DMO (SEQ ID NO:18). Both samples showed one amino acid of the CTP remaining on the amino-terminal end of the DMO after processing (DMO+1). Three unique events were tested for the At.CR88 CTP (SEQ ID NO:3) operably linked to DMO (SEQ ID NO:18). All three samples showed either zero or one amino acid of the CTP remaining on the amino-terminal end of the DMO after processing (DMO and DMO+1). The event tested from CTP4 (SEQ ID NO:4) operably linked to DMO (SEQ ID NO:19) showed twelve amino acids of the CTP remaining on the amino-terminal end of the DMO after processing (DMO+12). Two unique events were tested for the Os.Waxy CTP (SEQ ID NO:6) operably linked to DMO (SEQ ID NO:18). One sample showed ten amino acids of the CTP remaining on the amino-terminal end of the DMO after processing (DMO+10) and one showed the first methionine of the DMO was removed after processing (DMO-1). These results indicate that the APG6 CTP and the At.CR88 CTP are efficiently processed from the DMO when expressed in transgenic plants.

Example 3: CTP-DMO Expression in Transgenic *Brassica napus*

The ability of DNA constructs comprising a recombinant DNA molecule encoding one of three separate CTPs operably linked to DMO to provide dicamba tolerance was assessed with transgenic *Brassica napus* plants.

Transgenic *Brassica napus* plants were produced using three different plant transformation vectors each comprising a DNA construct containing one of three different CTPs operably linked to DMO operably linked to a promoter. *Brassica napus* variety 65037 Restorer line was used for *Agrobacterium*-mediated transformation and R0 plants were grown in the greenhouse. Unique events were screened for the copy number of the transgene. R0 plants with one copy of the transgene were selfed and R1 seed collected.

Dicamba tolerance was assessed using R0 plants with one copy of transgene with vector backbone or two copies of transgene. Dicamba tolerance was designated as dicamba injury of 20% or less under greenhouse conditions. R0 events in pots were divided into three groups and dicamba (Clarity®) was applied at one of three rates: (1) no dicamba, (2) 1 lb ae/acre dicamba (2× rate), or (3) 2 lb ae/acre dicamba (4× rate). Transgenic plants were sprayed and injury ratings were recorded 21 days later. Plants containing the "A" CTP operably linked to DMO (SEQ ID NO:21) showed no events tolerant to dicamba. Plants containing the RbcS CTP (SEQ ID NO:5) operably linked to DMO (SEQ ID NO:21) showed 8 of 9 events having tolerance to the 2× rate of dicamba and 7 of 7 events having tolerance to the 4× rate of dicamba. Plants containing the APG6 CTP (SEQ ID NO:1) operably linked to DMO (SEQ ID NO:20) showed 7 of 14 events having tolerance to the 2× rate of dicamba and 6 of 18 events having tolerance to the 4× rate of dicamba. Results are provided in Table 6.

TABLE 6

Dicamba tolerance in R0 *Brassica napus*

| CTP | DMO | 2X Tolerant events | 4X Tolerant events |
| --- | --- | --- | --- |
| APG6 (SEQ ID NO: 1) | SEQ ID NO: 20 | 7/14 | 6/18 |
| RbcS (SEQ ID NO: 5) | SEQ ID NO: 21 | 8/9 | 7/7 |
| A (Construct 7) | SEQ ID NO: 21 | 0 | 0 |

Dicamba tolerance was assessed on R0 plants with a one copy of the transgene. Plants were sprayed in the greenhouse with dicamba (Clarity) at 1 lb ae/acre (2× rate), and dicamba tolerance was determined 14 to 21 days later. Plants containing the APG6 CTP operably linked to DMO (SEQ ID NO:20) showed 13 events of 31 having tolerance to dicamba. Plants containing the RbcS CTP operably linked to DMO (SEQ ID NO:21) showed 13 events of 17 having tolerance to dicamba. Plants containing the "A" CTP operably linked to DMO (SEQ ID NO:21) showed 7 events of 18 having tolerance to dicamba. Results are provided in Table 7.

TABLE 7

Dicamba tolerance in R0 *Brassica napus*

| CTP | DMO | 2X Tolerant events |
| --- | --- | --- |
| APG6 (SEQ ID NO: 1) | SEQ ID NO: 20 | 13/31 |
| RbcS (SEQ ID NO: 5) | SEQ ID NO: 21 | 13/17 |
| A (Construct 7) | SEQ ID NO: 21 | 7/18 |

Ten seeds from each of 28 R1 plants containing the APG6 CTP operably linked to DMO (SEQ ID NO:20) (APG6+DMO) and ten seeds from each of 17 R1 plants containing RbcS CTP operably linked to DMO (SEQ ID NO:21) (RbcS+DMO) were grown in a greenhouse. Plants were sprayed with 2 lb ae/acre dicamba (4×) on the day of planting, followed by 1 lb ae/acre dicamba (2×) dicamba at V3 stage, and 1 lb ae/acre dicamba (2×) dicamba at first flower (defined as >90% of plants having bolted and about 25% having at least one open flower). Injury ratings were taken seven days after each spray and expressed as percent injury compared to sprayed controls. For plants containing APG6+DMO, there were 9 progeny total from 2 events with dicamba injury ratings of ≤20% at each of the three rating periods. For plants containing RbcS+DMO, there were 77 plants across 16 events with dicamba tolerance of less than 20% at each of the three rating periods.

Protein characterization was done using leaves harvested from the R0 events. Leaf tissue was ground in liquid nitrogen and extracted with two volumes of 2× Laemmli buffer (BioRad, Hercules, Calif.) containing 10% 2-mercaptoethanol and 5 mM DTT. The samples were boiled and 10 µl loaded onto a 4-20% Criterion™ pre-cast gel (BioRad, Hercules, Calif.) and run in Tris/glycine/SDS buffer at 250V for 45 minutes. The protein in the gel was transferred to PVDF membrane at 400 mA for 30 minutes in Tris/glycine buffer containing 20% methanol. The DMO protein was detected using polyclonal rabbit anti-DMO antisera and an HRP-conjugated anti-rabbit secondary antibody. Signal was detected using the SuperSignal™ West Pico Chemiluminescent kit (ThermoFischer Scientific, Grand Island, N.Y.). There was a single band of approximately 38 kDa, which is the expected size for a completely processed DMO protein, for each of three events containing APG6-DMO. There were two bands of approximately 38 kDa and approximately 41 kDa for each of six events containing RbcS-DMO. The 41 kDa band is consistent with DMO+27 and has been reported in soybean containing RbcS-DMO previously (U.S. Pat. No. 7,838,729). There was a very low expression of the DMO protein in all events containing the "A" CTP-DMO, and signal detected after a long exposure were a band of approximately 50 kDa and a band of approximately 39 kDa. The 50 kDa band is approximates the expected size of a non-processed "A" CTP-DMO. These results indicate that APG6-DMO produced a single band of the expected size consistent with a fully processed DMO.

Recombinant protein was purified from leaf tissue of R0 plants containing APG6-DMO or RbcS-DMO. Amino-terminal sequence analysis was performed using Edman degradation chemistry as described. Amino-terminal sequence analysis confirmed the presence DMO amino-terminal sequences of DMO+27 and DMO-1 present in plants containing RbcS-DMO, consistent with the size of the DMO bands seen on the Western blot. Amino-terminal sequence analysis confirmed the presence of only DMO amino-terminal sequence DMO+1 in plants containing APG6-DMO, consistent with the size of the DMO bands seen on the Western blot. This result confirms that the use of the APG6 CTP results in complete processing of an operably linked DMO in plants.

Example 4: CTP-DMO Expression in Transgenic Maize

The expression of DNA constructs comprising a recombinant DNA molecule encoding one of two separate CTPs operably linked to DMO was analyzed in transgenic maize cells and plants.

Maize mesophyll protoplast transient transformation was used to assess relative DMO expression of two CTP-DMO combinations. The DNA constructs were identical except that the CTP operably linked to the DMO (SEQ ID NO:18) was either APG6 (SEQ ID NO:1) or CTP4 (SEQ ID NO:4). Protoplasts were prepared essentially as described in Example 1. After transformation the cells were harvested and DMO protein levels were determined with an enzyme-linked immunosorbent assay (ELISA). Protein from four transformed protoplast samples were measured for each CTP-DMO combination as nanogram (ng) DMO per milligram (mg) total protein. Protoplasts transformed with APG6-DMO had approximately 4-fold higher levels of DMO compared to the protoplasts transformed with CTP4-DMO. Data are provided in Table 8.

Transgenic maize plants were generated using the DNA constructs, and R0 plants were grown. Leaf samples were collected from R0 plants representing eight unique single-copy events and use for quantitative ELISA to measure DMO levels. The DMO expression in R0 leaf tissue was approximately 4-fold higher for events containing APG6-DMO compared to events containing CTP4-DMO. Data are provided in Table 8.

Amino-terminal sequencing was performed for DMO expressed in transgenic maize plants. Protein was purified from transgenic maize plants expressing CTP4-DMO or APG6-DMO and prepared for Edman degradation sequencing essentially as described in Example 2. Amino-terminal sequence analysis confirmed DMO amino-terminal sequences of DMO+6, DMO+7, and DMO+12 present in plants containing CTP4-DMO. Amino-terminal sequence analysis confirmed DMO amino-terminal sequences of DMO and DMO+1 in plants containing APG6-DMO. These results indicate that the processing of the CTP is more complete with APG6 compared to CTP4, as evidenced by fewer CTP amino acids remaining at the amino-terminal end of the DMO. Data are provided in Table 8.

TABLE 8

DMO protein expression in maize

| CTP | Protoplast DMO levels (ng/mg) (SD) | R0 plant DMO levels (ng/mg) (SD) | CTP-DMO Processing |
|---|---|---|---|
| APG6 (SEQ ID NO: 1) | 12.44 (1.91) | 5.44 (0.82) | DMO and DMO + 1 |
| CTP4 (SEQ ID NO: 4) | 3.10 (0.64) | 1.19 (0.55) | DMO + 12, DMO + 7, and DMO + 6 |

Transgenic maize was generated by *Agrobacterium* mediated transformation using methods known to those of skill in the art with a DNA construct containing a recombinant DNA molecule encoding either APG6-DMO or CTP4-DMO. Dicamba tolerance was evaluated in a field trial for the transgenic F1 hybrid plants. The field trial included four treatments at two locations with two replications each. The four treatments were: (1) dicamba (Clarity®) applied at 2 lbs ae/acre (4×) at V2 followed by V4 followed by V8; (2) dicamba applied at 4 lbs at/acre (8×) at V2 followed by V4 followed by V8; (3) dicamba applied at 8 lbs at/acre (16×) at V2 followed by V4 followed by V8; and (4) dicamba applied at 16 lbs at/acre (32×) at V2 followed by V4 followed by V8. Crop injury was rated ten days after treatment and measured as crop injury percent per V-stage (CIPV2, CIPV4, or CIPV8). At the end of the season, grain was harvested and yield measured as bushels/acre. For both CIPV ratings and yield the least significant difference (LSD) at probability of 5% (p=0.05) was calculated. The highest dicamba rates (16× and 32×) applied to F1 hybrid plants containing APG6-DMO showed slightly less vegetative injury and higher grain yield than plants containing CTP4-DMO. Data are provided in Table 9.

TABLE 9

F1 hybrid field trial testing of dicamba injury and yield

| Dicamba | CTP-DMO | CIPV2 (LSD = 0.05) | CIPV4 (LSD = 0.05) | CIPV8 (LSD = 0.05) | Yield bu/ac (LSD = 0.05) |
|---|---|---|---|---|---|
| 2 lbs | CTP4-DMO | 0.75 (4.7) | 0.75 (7.1) | 4.25 (4.6) | 239.13 (21.17) |
|  | APG6-DMO | 0.75 (4.7) | 2 (7.1) | 3 (4.6) | 231.99 (21.17) |
|  | Negative Control | 40.63 (4.7) | 45 (7.1) | 49.38 (4.6) | 58.25 (21.17) |
| 4 lbs | CTP4-DMO | 2 (5.4) | 1.25 (6.6) | 7.5 (5.3) | 232.87 (17.11) |
|  | APG6-DMO | 1.5 (5.4) | 2 (6.6) | 7.5 (5.3) | 230.44 (17.11) |
|  | Negative Control | 46.875 (5.4) | 65 (6.6) | 80 (5.3) | 5.69 (17.11) |
| 8 lbs | CTP4-DMO | 2.5 (8.4) | 4 (5.3) | 15 (6.7) | 206.63 (28.15) |
|  | APG6-DMO | 1.5 (8.4) | 4 (5.3) | 11.25 (6.7) | 242.37 (28.15) |
|  | Negative Control | 73.125 (8.4) | 81.25 (5.3) | 87.375 (6.7) | 3.51 (28.15) |
| 16 lbs | CTP4-DMO | 6.25 (4.8) | 8.75 (3.1) | 16.25 (0) | 199.8 (18.35) |
|  | APG6-DMO | 2 (4.8) | 5.75 (3.1) | 17.5 (0) | 212.34 (18.35) |
|  | Negative Control | 82.5 (4.8) | 90.625 (3.1) | 99.5 (0) | 5.03 (18.35) |

Example 5: CTP-DMO Expression in Transgenic Cotton and Soybean

The APG6 CTP was optimized to enhance protein translation efficacy (protein synthesis) and increase protein accumulation. Optimized APG6 CTP (SEQ ID NO:2) has an amino acid change from threonine (T) to serine (S) at positions 3 and 4 of the APG6 CTP (SEQ ID NO:1). DNA constructs were made to compare the two CTPs, each operably linked to DMO in soybean.

Transgenic soybean plants were generated with two DNA constructs that were identical except for the APG6 CTP. The first DNA construct had APG6 (SEQ ID NO:1) operably linked to DMO (SEQ ID NO:18). The second DNA construct had the optimized APG6 (SEQ ID NO:2) operably linked to DMO (SEQ ID NO:18). Each DNA construct was used to transform A3555 soybean by *Agrobacterium* mediated transformation methods. Following transformation, R0 transgenic plants containing a single copy of the transgene were identified by PCR assay. Single-copy R0 plants were grown in greenhouse, and R1 seed was harvested. Ten R1 seeds per event for 4 events generated using each of the two DNA constructs and AG3555 seed was planted for evaluation of crop tolerance to post-emergence dicamba treatment under standard greenhouse growth conditions. Dicamba (Clarity) was applied at the V4 stage at 1120 g ai/ha. Crop injury ratings were taken 10 days after the treatment. Leaf samples from dicamba tolerant soybean plants were taken for recombinant protein level measurements and amino-terminal sequence analysis. The DMO protein level was detected by ELISA to be 13.35±2.7 ng/mg for the single-copy dicamba tolerant R1 transgenic soybean plants with the APG6 CTP (SEQ ID NO:1) operably linked to DMO (SEQ ID NO:18). The DMO protein level was detected by ELISA to be 18.55±3.1 ng/mg for the single-copy dicamba tolerant R1 transgenic soybean plants with the optimized APG6 CTP (SEQ ID NO:2). No DMO protein was detected in the negative control A3555 soybean leaf tissue. The dicamba injury rating for the single-copy R1 transgenic soybean plants with the APG6 CTP (SEQ ID NO:1) operably linked to DMO (SEQ ID NO:18) was 3.6%. The dicamba injury rating for the single-copy R1 transgenic soybean plants with the optimized APG6 CTP (SEQ ID NO:2) operably linked to DMO (SEQ ID NO:18) was 2.7%. The negative control A3555 soybean had a dicamba injury rating of 99.8%. The leaf samples from the single-copy dicamba tolerant R1 transgenic soybean plants was used for amino-terminal sequencing (as described in Examples 2 and 4). Amino-terminal sequence analysis confirmed that the processing of APG6-DMO and optimized APG6-DMO resulted in full processing of the CTP from the amino-terminus of the DMO protein. The DMO levels, dicamba injury, and APG6-DMO processing indicated that both the APG6 and optimized APG6 when operably linked to DMO provide tolerance to dicamba and both CTPs are processed fully in plants. Data are provided in Table 10.

TABLE 10

R1 Soybean greenhouse testing

| CTP | Leaf DMO levels (ng/mg) | Dicamba Injury, V4 stage | APG6-DMO processing |
|---|---|---|---|
| APG6 SEQ ID NO: 1 | 13.35 ± 2.7 | 3.6% | DMO |
| Optimized APG6 SEQ ID NO: 2 | 18.55 ± 3.1 | 2.7% | DMO |
| Negative Control A3555 | Not detected | 99.8% | not applicable |

Transgenic cotton plants were generated with two DNA constructs that were identical except for the APG6 CTP. The first DNA construct had APG6 (SEQ ID NO:1) operably linked to DMO (SEQ ID NO:18). The second DNA construct had the optimized APG6 CTP (SEQ ID NO:2) operably linked to DMO (SEQ ID NO:18). Each DNA construct was transformed to cotton by Agrobacterium mediated transformation using methods known to those of skill in the art. Following transformation, R0 cotton transgenic plants containing a single copy of the transgene were identified by PCR assay, grown in greenhouse, and R1 seed was harvested. Ten R1 seeds per event from 10 events for each construct and seed from DP393 cotton was planted to evaluate crop tolerance to post-emergence application of dicamba. Dicamba (Clarity) was applied at the V4 stage at 1120 g ai/ha. Crop injury percent ratings were taken 9 days after the treatment. Leaf samples from tolerant cotton plants were used for protein level measurement and APG6-DMO or optimized APG6-DMO amino-terminal sequence analysis. The DMO protein level detected by ELISA was 176.2±103 ng/mg for the single-copy dicamba tolerant R1 transgenic cotton plants with the APG6 CTP (SEQ ID NO:1) operably linked to DMO (SEQ ID NO:18). The DMO protein level detected by ELISA was 136.5±58.6 ng/mg for the single-copy dicamba tolerant R1 transgenic cotton plants with the optimized APG6 CTP (SEQ ID NO:2). No DMO protein was detected in the negative control DP393 cotton leaf tissue. The dicamba injury for the single-copy R1 transgenic cotton plants with the APG6 CTP (SEQ ID NO:1) operably linked to DMO (SEQ ID NO:18) was 2.6%. The dicamba injury for the single-copy R1 transgenic plants with the optimized APG6 CTP (SEQ ID NO:2) operably linked to DMO (SEQ ID NO:18) was 2.2%. The negative control DP393 cotton injury was 85%. Leaf samples from the single-copy dicamba tolerant R1 plants were used for amino-terminal sequencing (as described in Examples 2 and 4). Amino-terminal sequence analysis confirmed that the processing of APG6-DMO and optimized APG6-DMO resulted in full processing of the CTP from the amino-terminus of the DMO protein. The DMO protein expression level, dicamba injury, and APG6-DMO and optimized APG6-DMO amino-terminal processing indicated that both the APG6 and optimized APG6 when operably linked to DMO provide tolerance to dicamba and both CTPs are processed fully in plants. Data are provided in Table 11.

TABLE 11

R1 Cotton greenhouse testing

| CTP | Leaf DMO levels (ng/mg) | dicamba % Injury, V4 stage | APG6-DMO Processing |
|---|---|---|---|
| APG6 (SEQ ID NO: 1) | 176.2 ± 103 | 2.6% | DMO |
| Optimized APG6 (SEQ ID NO: 2) | 136.5 ± 58.6 | 2.2% | DMO |
| Negative Control DP393 | Not detected | 85% | not applicable |

Example 6: CTP-PPO Expression in Transgenic Maize

Novel PPOs that are tolerant to PPO herbicides were identified using an herbicide bacterial screening system. This screening system used a growth assay of the knockout E. coli strain in LB liquid medium with a PPO herbicide to identify PPOs that were not sensitive to the PPO herbicide.

The knockout E. coli strain was transformed with a bacterial expression vector containing the confirmed PPO activity and cultured in LB liquid medium. Purified crystalline form of one of five different PPO herbicides (acifluorfen (1 mM), flumioxazin (0.5 mM), lactofen (0.5 mM), fomesafen (1 mM), and S-3100 (100 µM), representing three different PPO chemistry subclasses, was added to the medium. Recombinant proteins were expressed and the E. coli growth rates were measured. Growth curves (OD600) were measured for the different variants in the presence and absence of the PPO herbicides at selected time-points from time zero to twenty-four hours. The growth of a transformed knockout E. coli strain in LB medium in the presence of a PPO herbicide indicated that the gene used to transform the E. coli encoded an herbicide-insensitive protoporphyrinogen oxidase (iPPO).

Ten PPOs provided as SEQ ID NOs:40-49 were all found to confer normal growth rates on the knockout E. coli strain in LB medium in the presence of a PPO herbicide, indicating that these proteins are herbicide-insensitive protoporphyrinogen oxidases (iPPO). The knockout E. coli strain expressing the WH_PPO (SEQ ID NO:60) was sensitive to all five PPO herbicides, confirming that the assay was able to distinguish between sensitive and insensitive PPOs for each of the herbicides.

Four plant transformation vectors were created for expressing the PPO H_N10 (SEQ ID NO:43) in planta. Transformation constructs 1 and 11 had the same promoter plus leader plus intron combination, the same 3'UTR sequence, the same PPO H_N10 (SEQ ID NO:43), but differed in the CTP sequences, and were used in transformation of soybean. Transformation constructs 6 and 16 had the same promoter plus leader plus intron combination, the same 3'UTR sequence, the same PPO H_N10 (SEQ ID NO:43), but differed in the CTP sequences, and were used in transformation of maize. Table 12 provides configuration of the PPO H_N10 plant transformation constructs.

TABLE 12

Construct configuration with PPO H_N10

| Transformation crop | Construct | CTP | CTP SEQ ID NO |
|---|---|---|---|
| Soybean and Cotton | 1 | APG6 | SEQ ID NO: 1 |
| Soybean | 11 | 12G088600TP | SEQ ID NO: 38 |
| Maize | 6 | APG6 | SEQ ID NO: 1 |
|  | 16 | 12G088600TP | SEQ ID NO: 38 |

The PPO enzymes were expressed in transgenic maize plants, and the transgenic plants were analyzed for PPO herbicide tolerance. Plant transformation vectors were constructed comprising a recombinant DNA molecule encoding one of the PPO enzymes provided as SEQ ID NOs:40-59. The DNA sequence encoding a PPO enzyme can include at the 5' end a codon for a methionine, commonly known as a start codon, or this codon can be eliminated to facilitate operable linkage of a chloroplast transit peptide sequence to the 5' end of the coding sequence. Examples of PPO enzyme protein sequences containing a methionine at the amino-terminus are provided as SEQ ID NOs:40-49. Examples of PPO enzyme protein sequences without a methionine at the amino-terminus are provided as SEQ ID NOs:50-59. For plant transformation, the nucleotide sequences encoding the putative PPO enzymes were codon optimized for either dicot or monocot expression. Table 2 provides the SEQ ID NOs corresponding to the protein and nucleotide sequences of the PPO enzymes in the transformation vectors.

For maize in planta testing, maize (LH244) was transformed using *Agrobacterium tumefaciens* and standard methods known in the art. Transgenic F1 plants produced from outcrossing the single-copy R0 plants expressing H_N10 (SEQ ID NO:43) in one of two construct configurations were tested in the greenhouse for herbicide tolerance. The plants were treated with 40 grams/ha S-3100 at the V3 growth stage and injury ratings were taken seven days after treatment. Transgenic maize plants expressing H_N10 (SEQ ID NO:43) in the construct 6 configuration (APG6 (SEQ ID NO:1) operably linked to PPO H_N10 (SEQ ID NO:43)) resulted in 13 out of 18 events producing highly tolerant plants (10% or less injury) but the construct 16 configuration (12G088600TP (SEQ ID NO:38) operably linked to PPO H_N10 (SEQ ID NO:43)) resulted in no events producing highly tolerant plants.

Transgenic F1 plants produced from outcrossing the single-copy R0 plants expressing H_N10 (SEQ ID NO:43) in one of two construct configurations (constructs 6 and 16) were tested in the field for herbicide tolerance. This F1 population was segregating (50% hemizygous and 50% null) and selection for transgenic plants was not conducted prior to injury ratings. The overall average injury ratings for such a population are expected to be higher than a homogenous transgenic population since it is difficult to discern non-transgenic plants from transgenic plants. The trials were conducted at two locations with two replicates and 3 treatments per construct. Non-transgenic maize plants were used as a negative control. The herbicide application treatments were as follows: Treatment 1 was 0.036 lb ai/acre S-3100 applied at V2 followed by (fb) V4 fb V8; Treatment 2: was 0.072 lb ai/acre S-3100 applied at V2 fb V4 fb V8; Treatment 3: was 0.144 lb ai/acre S-3100 applied at V2 fb V4 fb V8. Crop Injury Percent ratings were assessed at the V2 growth stage (CIPV2) and at the V4 growth stage (CIPV4) at 5 to 7 days after treatment (the error V2 and error V4 are half of the least significant difference (LSD)). The crop injury ratings were combined for both locations. All non-transgenic plants and plants with events generated using construct 16 (12G088600TP (SEQ ID NO:38) operably linked to PPO H_N10 (SEQ ID NO:43)) showed between 94.6-99.5% injury following both the V2 and V4 herbicide application for each of the three treatments. Plants with events generated using construct 6 (APG6 (SEQ ID NO:1) operably linked to PPO H_N10 (SEQ ID NO:43)) showed only 30% to 50% injury following the V2 herbicide application and no injury following the V4 herbicide application. Data are provided in Table 13.

TABLE 13

Efficacy field trial of F1 maize containing PPO H_N10 (SEQ ID NO: 43)

| Treatment | Construct | CTP | CTP SEQ ID NO | CIPV2 | CIPV4 | Error V2 | Error V4 |
|---|---|---|---|---|---|---|---|
| Trt 1 | Negative control | n/a | n/a | 94.6 | 99 | 8.6 | 1.2 |
|  | 6 | APG6 | 1 | 37.5 | 0 | 8.6 | 1.2 |
|  | 16 | 12G088600TP | 38 | 96.3 | 98.5 | 8.6 | 1.2 |
| Trt 2 | Negative control | n/a | n/a | 99.5 | 99.5 | 5.4 | 0 |
|  | 6 | APG6 | 1 | 37.5 | 0 | 5.4 | 0 |
|  | 16 | 12G088600TP | 38 | 99.5 | 99.5 | 5.4 | 0 |
| Trt 3 | Negative control | n/a | n/a | 99.5 | 99.5 | 0 | 0 |
|  | 6 | APG6 | 1 | 50 | 0 | 0 | 0 |
|  | 16 | 12G088600TP | 38 | 99.5 | 99.5 | 0 | 0 |

The F1 transgenic maize greenhouse and field data demonstrated that APG6 (SEQ ID NO:1) operably linked to PPO H_N10 (SEQ ID NO:43) produced reduced injury rates when expressed in transgenic plants as compared to the injury rates when 12G088600TP (SEQ ID NO:38) operably linked to PPO H_N10 (SEQ ID NO:43) was expressed in transgenic plants. See, FIG. 1.

Plant transformation vectors were created for expressing in planta either PPO H_N40 (SEQ ID NO:54) or PPO H_N90 (SEQ ID NO:50) operably linked to APG6 (SEQ ID NO:1), CTP D, or CTP E. Maize (01DKD2) was transformed using *Agrobacterium tumefaciens* and standard methods known in the art. Leaf samples taken from the resulting R0 plants were analyzed by PCR to determine the copy number of the transgene insert. R0 plants each containing a unique transformation event were sprayed with 40 g ai/ha or 80 g ai/ha of S-3100 at approximately the V5 growth stage and injury ratings were taken 4-7 days after treatment. The number of plants with ≤10% injury (highly tolerant) or ≤20% injury (tolerant) of the total number of sprayed plants was recorded. Plants that were determined to be single-copy events and that passed spray at ≤20% injury were advanced to selfing and outcrossing. Data are presented in Table 14.

TABLE 14

CTP-PPO herbicide tolerance evaluation in transgenic maize

| Construct configuration | CTP | PPO | S-3100 rate (g ai/ha) | ≤10% injury | ≤20% injury |
|---|---|---|---|---|---|
| 17 | APG6 | H_N40 | 80 | 42/112 (37.5%) | 65/112 (58%) |
| 17 | D | H_N40 | 80 | 0/46 (0%) | 1/46 (2.2%) |
| 17 | E | H_N40 | 40 | 0/101 (0%) | 13/101 (12.9%) |
| 17 | APG6 | H_N90 | 40 | 55/112 (49.1%) | 63/112 (56.3%) |
| 18 | APG6 | H_N40 | 80 | 45/112 (40.2%) | 66/112 (58.9%) |
| 18 | E | H_N40 | 40 | 9/112 (8%) | 36/112 (32.1%) |
| 19 | APG6 | H_N40 | 80 | 12/56 (21.4%) | 23/56 (41.1%) |
| 19 | E | H_N40 | 40 | 3/112 (2.7%) | 9/112 (8.0%) |

The results show that APG6 (SEQ ID NO:1) consistently produced higher herbicide tolerance compared to plants transformed with the CTP D or CTP E when operably linked to H_N40 (SEQ ID NO:54) or H_N90 (SEQ ID NO:50). APG6 when operably linked to H_N40 resulted in 21.4% to 40.2% of transgenic plants being highly tolerant and 41.1% to 58.9% of transgenic plants being tolerant to S-3100 at 80 g ai/ha. APG6 when operably linked to H_N90 resulted in 49.1% of transgenic plants being highly tolerant and 56.3% of transgenic plants being tolerant to S-3100 at 40 g ai/ha. CTP D when operably linked to H_N40 resulted in 0% of transgenic plants being highly tolerant and 2.2% being tolerant to S-3100 at 80 g ai/ha. CTP E when operably linked to H_N40 resulted in 0% to 8% of transgenic plants being highly tolerant and 12.9% to 32.1% being tolerant to S-3100 at the lower herbicide rate of 40 g ai/ha.

Transgenic F1 hybrid maize expressing APG6 operably linked to PPO H_N10 was assessed for tolerance to different seven different PPO herbicides: S-3100, Fomesafen, Acifluorfen, Lactofen, Flumioxazin, Sulfentrazone, and Saflufenacil. Pooled seed representing 5 unique events was planted in pots in a greenhouse along with hybrid maize seed as a negative control.

To test for pre-emergence herbicide tolerance, PPO herbicides were applied individually at one of two rates with six reps per treatment as follows: S-3100 (80 or 160 g ai/ha), fomesafen (Reflex®, 840 or 1680 g ai/ha), flumioxazin (Valor® SX, 210 or 420 g ai/ha), sulfentrazone (Spartan® 4L, 840 or 1680 g ai/ha), and saflufenacil (Sharpen®, 200 or 400 g ai/ha). Plants were rated for percentage of crop injury at 20 days after treatment, and maize seed was included as a negative control. Transgenic plants with APG6 operably linked to PPO H_N10 had injury ratings for the different PPO herbicides applied pre-emergence ranging from 0% to 5.8%, indicating that APG6 operably linked to PPO H_N10 provided excellent pre-emergence tolerance to the maize at both herbicide rates for all of the five PPO herbicides. Negative control maize plants had injury ratings ranging from 17.5% to 94.2%, with the exception of Saflufenacil, which is expected since this herbicide is marketed for used in conventional maize plants. Data are presented in Table 15 with standard error indicated as +/−.

TABLE 15

PPO herbicide pre-emergence injury ratings in maize

| TRT # | Chemistry | Rate (g ai/ha) | % Injury negative control | % Injury PPO H_N10 |
|---|---|---|---|---|
| 1 | S-3100 | 80 | 19.2% +/− 2.39 | 3.3% +/− 1.67 |
| 2 | | 160 | 20.8% +/− 8.31 | 4.2% +/− 1.54 |
| 3 | Fomesafen | 840 | 75.8% +/− 5.83 | 4.2% +/− 1.54 |
| 4 | | 1680 | 94.2% +/− 1.54 | 5.8% +/− 0.83 |
| 5 | Flumioxazin | 210 | 30% +/− 6.32 | 1.7% +/− 1.05 |
| 6 | | 420 | 60.8% +/− 6.38 | 2.5% +/− 1.71 |
| 7 | Sulfentrazone | 840 | 17.5% +/− 11.6 | 0% +/− 0 |
| 8 | | 1680 | 20% +/− 11.11 | 0% +/− 0 |
| 9 | Saflufenacil | 200 | 0% +/− 0 | 0% +/− 0 |
| 10 | | 400 | 0.8% +/− 0.83 | 0.8% +/− 0.83 |

To test for post-emergence (V3 to V4) herbicide tolerance, PPO herbicides were applied individually at one of three rates with six reps per treatment as follows: S-3100 (40, 80, or 160 g ai/ha), fomesafen (Reflex®, 420, 840, or 1680 g ai/ha), acifluorfen (Ultra Blazer®, 420, 840, or 1680 g ai/ha), lactofen (Cobra®, 220, 440, or 880 g ai/ha), flumioxazin (Valor® SX, 105, 210, or 420 g ai/ha), sulfentrazone (Spartan® 4L, 420, 840, or 1680 g ai/ha), and saflufenacil (Sharpen®, 100, 200, or 400 g ai/ha). Plants were rated for percentage of crop injury at 14 days after treatment, and conventional hybrid maize seed was included as a negative control. Transgenic plants with APG6 operably linked to PPO H_N10 had injury ratings for the different PPO herbicides applied post-emergence ranging from 0.5% to 5.8%, with the exception of fomesafen at 1680 g ai/ha where the injury rating was 13.8%, indicating that APG6 operably linked to PPO H_N10 provided excellent post-emergence tolerance to the maize at all herbicide rates for all of the seven PPO herbicides. Negative control maize plants had injury ratings ranging from 36.7% to 100%. Data are presented in Table 16 with standard error indicated as +/−.

TABLE 16

PPO herbicide post-emergence injury ratings in maize

| PPO Herbicide | Rate (g ai/ha) | % Injury Negative control | % Injury PPO H_N10 |
|---|---|---|---|
| S-3100 | 40 | 100% =/− 0 | 1.80% =/− 0.87 |
| | 80 | 100% =/− 0 | 3.80% =/− 0.83 |
| | 160 | 100% =/− 0 | 3.80% =/− 0.98 |
| Fomesafen | 420 | 98.50% =/− 0.81 | 2.30% =/− 0.8 |
| | 840 | 100% =/− 0 | 4.70% =/− 0.8 |
| | 1680 | 100% =/− 0 | 13.80% =/− 1.54 |
| Acifluorfen | 420 | 84.20% =/− 5.69 | 1.80% =/− 0.87 |
| | 840 | 87.50% =/− 2.14 | 4.70% =/− 0.8 |
| | 1680 | 95.50% =/− 1.38 | 5.30% =/− 0.61 |
| Lactofen | 220 | 58.30% =/− 3.07 | 1% =/− 0.63 |
| | 440 | 59.20% =/− 2.71 | 2.20% =/− 1.01 |
| | 880 | 61.70% =/− 6.54 | 5.80% =/− 0.98 |
| Flumioxazin | 105 | 51.70% =/− 3.07 | 1% =/− 0.63 |
| | 210 | 69.20% =/− 6.38 | 1.30% =/− 0.88 |
| | 420 | 68.30% =/− 2.79 | 1.80% =/− 0.87 |
| Sulfentrazone | 420 | 61.70% =/− 5.43 | 0.50% =/− 0.5 |
| | 840 | 79.20% =/− 5.97 | 1% =/− 0.63 |
| | 1680 | 84.20% =/− 3.27 | 2.70% =/− 0.92 |
| Saflufenacil | 100 | 43.30% =/− 2.11 | 0.80% =/− 0.83 |
| | 200 | 36.70% =/− 2.11 | 1.30% =/− 0.88 |
| | 400 | 53.30% =/− 2.11 | 1.80% =/− 0.87 |

Example 7: CTP-PPO Expression in Transgenic Soybean

PPO enzymes operably linked to different CTPs were expressed in transgenic soybean plants, and the transgenic plants were analyzed for PPO herbicide tolerance.

Plant transformation vectors were created for expressing in planta 12G088600TP (SEQ ID NO:38) operably linked to PPO H_N10 (SEQ ID NO:43) or APG6 (SEQ ID NO:1) operably linked to PPO H_N10 (SEQ ID NO:43). Soybean A3555 was transformed using these plant transformation vectors and *Agrobacterium tumefaciens* using standard methods known in the art. Regenerated R0 transgenic plantlets were grown in the greenhouse, selfed, and R1 seed was collected. Transgenic R1 plants were sprayed in the greenhouse with one of three herbicide treatments applied at V4 and R1: (1) 5 grams ai/ha S-3100, (2) 10 grams ai/ha S-3100, or (3) 30 grams ai/ha S-3100. Crop injury ratings were assessed at ten days after treatment. Transgenic plants expressing APG6 (SEQ ID NO:1) operably linked to PPO H_N10 (SEQ ID NO:43) had injury ratings ranging from 4.2%, 7.8%, and 9.4% at the V4 stage and 3%, 6.5%, to 15.7% at the R1 stage, at the 5, 10, and 30 g ai/ha rates, respectively. Transgenic plants expressing 12G088600TP (SEQ ID NO:38) operably linked to PPO H_N10 (SEQ ID NO:43) had average injury ratings of 82.7%, 92.7%, to 98.2%% at the 5, 10, and 30 g ai/ha rates, respectively, and did not survive for rating at the R1 stage. Negative control plants had similar average injury ratings of 89%, 98%, and 100% at the 5, 10, and 30 g ai/ha rates, respectively, and did not survive for rating at the R1 stage. Data are provided in Table 17.

TABLE 17

PPO Herbicide testing of R1 soybean

| Construct | S-3100 Rate | Injury V4 stage | Injury R1 stage |
|---|---|---|---|
| APG6 + H_N10 | 5 g/ha | 4.2% | 3% |
| APG6 + H_N10 | 10 g/ha | 7.8% | 6.5% |
| APG6 + H_N10 | 30 g/ha | 9.4% | 15.7% |
| 12G088600TP + H_N10 | 5 g/ha | 82.7% | not available |
| 12G088600TP + H_N10 | 10 g/ha | 92.7% | not available |
| 12G088600TP + H_N10 | 30 g/ha | 98.2% | not available |
| Negative Control | 5 g/ha | 89% | not available |
| Negative Control | 10 g/ha | 98% | not available |
| Negative Control | 30 g/ha | 100% | not available |

Plant transformation vectors were created for expressing in planta PPO H_N90 (SEQ ID NO:47) operably linked to one of three different CTPs, APG6 (SEQ ID NO:1) CTP F, and CTP H. Soybean A3555 was transformed using these plant transformation vectors and *Agrobacterium tumefaciens* using standard methods known in the art. Regenerated R0 transgenic plantlets were grown in the greenhouse, and leaf samples taken from the resulting R0 plants were analyzed by PCR to identify plants containing a single copy of an event. Transgenic single-copy R0 plants, each representing a unique event, were sprayed in the greenhouse with the herbicide treatment 20 g ai/ha S-3100 applied at approximately the V3 stage. Injury ratings were taken 14 days after treatment as the number that were deemed highly tolerant (≤10% injury) or tolerant (≤20% injury). Transgenic plants expressing APG6 (SEQ ID NO:1) operably linked to PPO H_N90 (SEQ ID NO:47) resulted in 21.4% of unique events being highly tolerant and 57.1% being tolerant. Transgenic plants expressing CTP F operably linked to PPO H_N90 (SEQ ID NO:47) resulted in 11.7% of unique events being highly tolerant and 41.1% being tolerant. Transgenic plants expressing CTP H operably linked to PPO H_N90 PPO H_N90 (SEQ ID NO:47) resulted in no unique events being highly tolerant or tolerant. Data are presented in Table 18.

TABLE 18

S-3100 efficacy evaluation in R0 soybean

| CTP | PPO | ≤10% injury | ≤20% injury |
|---|---|---|---|
| APG6 | H_N90 | 3/14 (21.4%) | 8/14 (57.1%) |
| F | H_N90 | 2/17 (11.7%) | 7/17 (41.1%) |
| H | H_N90 | 0/22 (0%) | 0/22 (0%) |

This data demonstrated that the specific CTP that is operably linked to a PPO enzyme is critical for achieving herbicide tolerance, thus showing the importance of the choice of CTP and the unexpected superiority of the APG6 CTP compared to other CTPs for use in producing herbicide tolerant transgenic plants.

Example 8: CTP-PPO Expression in Transgenic Cotton

Plant transformation vectors were created for expressing APG6 (SEQ ID NO:1) operably linked to PPO H_N10 (SEQ ID NO:43) in transgenic cotton plants, and the transgenic plants were analyzed for PPO herbicide tolerance. Cotton DP393 was transformed using the plant transformation vectors and *Agrobacterium tumefaciens* with standard methods known in the art. Regenerated R0 transgenic plantlets were grown in the greenhouse, and leaf samples taken from the resulting R0 plants were analyzed by PCR to identify plants containing a single copy of an event. Transgenic single-copy R0 plants, each representing a unique event, were sprayed in the greenhouse with the herbicide treatment 20 g ai/ha of S-3100 applied at V2 stage. Additionally, transgenic multi-copy (≥2 copies/plant) were sprayed in the greenhouse with the herbicide treatment 20 g ai/ha of S-3100 applied at V2 stage. Injury ratings were taken at three days after treatment.

The negative control, cotton DP393, had 100% injury three days after herbicide treatment with 20 g ai/ha of S-3100. In contrast, 21 single-copy R0 plants had an average injury of 26.7%. The distribution of injury for the 21 single-copy R0 plants was: 3 plants with no injury; 3 plants with 10% injury; 3 plants with 15% injury; 2 plants with 20% injury; 7 plants with 30% injury; and 3 plants with 40% injury. For the multi-copy R0 plants, 14 plants received herbicide treatment and the average injury was 10.4%. The distribution of injury for the 14 multi-copy plants was: 5 plants with no injury; 3 plants with 5% injury; 1 plant with 10% injury; 2 plants with 15% injury; 1 plant with 20% injury; 1 plant with 30% injury; and 1 plant with 40% injury. This data demonstrates that R0 transgenic cotton expressing the APG6 (SEQ ID NO:1) operably linked to PPO H_N10 (SEQ ID NO:43) had tolerance to application of the herbicide S-3100 at 20 g ai/ha applied at V2 stage.

What is claimed is:

1. A recombinant DNA molecule comprising a DNA sequence encoding a chloroplast transit peptide (CTP) operably linked to a DNA sequence encoding dicamba monooxygenase (DMO) or protoporphyrinogen oxidase (PPO), wherein the CTP comprises a sequence selected from the group consisting of SEQ ID NOs:1-3, and wherein said DNA sequence encoding a CTP is operably linked to a heterologous promoter functional in a plant cell.

2. The recombinant DNA molecule of claim 1, wherein the DNA sequence encoding the CTP comprises a sequence selected from the group consisting of SEQ ID NOs:7-14.

3. The recombinant DNA molecule of claim 1, wherein the DMO or PPO comprises a polypeptide sequence selected from the group consisting of SEQ ID NOs:18-27 and 40-59.

4. The recombinant DNA molecule of claim 3, wherein the DNA sequence encoding a DMO or PPO comprises a sequence selected from the group consisting of SEQ ID NOs:28-37 and 61-102.

5. The recombinant DNA molecule of claim 1, wherein the CTP is operably linked to a DMO protein, and the CTP comprises a sequence selected from the group consisting of SEQ ID NOs:1-3.

6. The recombinant DNA molecule of claim 1, wherein the CTP is operably linked to a PPO protein, and the CTP comprises a sequence selected from the group consisting of SEQ ID NOs:1 and 2.

7. A transgenic plant, plant cell, plant part, or seed comprising the DNA molecule of claim 1.

8. The transgenic plant, plant cell, plant part, or seed of claim 7, wherein the plant is a monocot plant.

9. The transgenic plant, plant cell, plant part, or seed of claim 8, wherein the plant is a maize or wheat plant.

10. The transgenic plant, plant cell, plant part, or seed of claim 7, wherein the plant is a dicot plant.

11. The transgenic plant, plant cell, plant part, or seed of claim 10, wherein the plant is a soybean, cotton, or *Brassica* plant.

12. A method for producing an herbicide tolerant plant comprising the steps of:
   a) transforming a plant cell with the recombinant DNA molecule of claim 1 and;
   b) regenerating a plant from the transformed plant cell that comprises the DNA construct.

13. The method of claim 12, wherein the regenerated plant is tolerant to an herbicide selected from the group consisting of dicamba and a PPO inhibitor.

14. A method of producing an herbicide tolerant plant comprising the steps of:
   a) crossing a parent plant comprising the DNA molecule of claim 1 with itself or with a second plant to produce one or more progeny plants; and
   b) selecting a progeny plant comprising said DNA molecule.

15. The method of claim 14, wherein the progeny plant is tolerant to an herbicide selected from the group consisting of dicamba and a PPO inhibitor.

16. The method of claim 15, wherein the progeny plant is tolerant to a PPO inhibitor herbicide selected from the group consisting of S-3100, fomesafen, acifluorfen, lactofen, flumioxazin, sulfentrazone, and saflufenacil.

17. A method of expressing dicamba monooxygenase (DMO) or protoporphyrinogen oxidase (PPO) comprising introducing the DNA molecule of claim 1 into a plant cell.

18. The method of claim 17, wherein introducing comprises transforming the plant cell.

19. A method for controlling weed growth in a crop growing environment comprising the steps of:
   a) planting the plant or seed of claim 7 in a crop growing environment; and
   b) applying to the crop growing environment an amount of dicamba or a PPO inhibitor herbicide effective to control weed growth.

20. The method of claim 19, wherein the herbicide does not damage the plant or seed.

21. The method of claim 19, wherein the plant or seed is a monocot plant or seed.

22. The method of claim 21, wherein the plant is a maize or wheat plant.

23. The method of claim 19, wherein the plant or seed is a dicot plant or seed.

24. The method of claim 23, wherein the plant is a soybean, cotton, or *Brassica* plant.

25. The method of claim 19, wherein the herbicide is dicamba.

26. The method of claim 19, wherein the herbicide is a PPO inhibitor.

* * * * *